(12) United States Patent
Martin

(10) Patent No.: US 9,783,571 B2
(45) Date of Patent: Oct. 10, 2017

(54) ISOLATION OF CYSTEINE CONTAINING PEPTIDES

(76) Inventor: Warham Lance Martin, Durham, NC (US)

(*) Notice: Subject to any disclaimer, the term of this patent is extended or adjusted under 35 U.S.C. 154(b) by 646 days.

(21) Appl. No.: 14/110,336

(22) PCT Filed: Apr. 5, 2012

(86) PCT No.: PCT/US2012/032416
§ 371 (c)(1),
(2), (4) Date: Mar. 2, 2015

(87) PCT Pub. No.: WO2012/138920
PCT Pub. Date: Oct. 11, 2012

(65) Prior Publication Data
US 2015/0158905 A1    Jun. 11, 2015

Related U.S. Application Data

(60) Provisional application No. 61/472,060, filed on Apr. 5, 2011.

(51) Int. Cl.
| | |
|---|---|
| C07K 1/22 | (2006.01) |
| C08G 63/91 | (2006.01) |
| C07C 237/22 | (2006.01) |
| C07C 259/06 | (2006.01) |
| C07C 271/16 | (2006.01) |
| B01J 20/32 | (2006.01) |

(52) U.S. Cl.
CPC ............ *C07K 1/22* (2013.01); *B01J 20/3208* (2013.01); *B01J 20/3219* (2013.01); *B01J 20/3248* (2013.01); *B01J 20/3251* (2013.01); *B01J 20/3253* (2013.01); *C07C 237/22* (2013.01); *C07C 259/06* (2013.01); *C07C 271/16* (2013.01); *C08G 63/914* (2013.01)

(58) Field of Classification Search
None
See application file for complete search history.

(56) References Cited

U.S. PATENT DOCUMENTS

| | | |
|---|---|---|
| 2007/0148721 A1 | 6/2007 | Nicol et al. |
| 2010/0305311 A1 | 12/2010 | Lee et al. |

FOREIGN PATENT DOCUMENTS

| | | |
|---|---|---|
| WO | 02/48717 | 6/2002 |
| WO | 2004/063250 | 7/2004 |
| WO | 2009/085106 | 7/2009 |

OTHER PUBLICATIONS

Giron et al. (Rapid Communications in Mass Spectrometry (2009) 23(21), 3377-3386).*
Giron et al., Rapid Commun. Mass Spectrom. (2009) 23, 3377-3386.*
Villain et al., Chemistry & Biology (2001) 8, 673-679.*
http://link.springer.com/referenceworkentry/10.1007%2F978-3-642-11274-4_21.*
Boja et al., "Overalkylation of a Protein Digest with Iodoacetamide," Anal. Chem. 73(15):3576-3582 (2001).
Brandtzaeg et al., "Proteomics tools reveal startlingly high amounts of oxytocin in plasma and serum," Sci Rep 6:31693 (2016).
Dawson et al., "Convenient total synthesis of a 4-helix template-assembled synthetic protein (TASP) molecule by chemoselective ligation," J. Am. Chem. Soc. 115(16): 7263-7266 (1993).
Goodacre et al., "Antibacterial halogenoacetyl derivatives of amino acids and simple peptides," J. Med. Chem., 20(11)1445-1448 (1977).
Leclerc et al., "On the selectivity of acylation of unprotected diamino acids," Canadian Journal of Chemistry 46(7): 1047-105 (1968).

(Continued)

*Primary Examiner* — Marcela M Cordero Garcia
*Assistant Examiner* — Catherine Mader
(74) *Attorney, Agent, or Firm* — McDonnell Boehnen Hulbert & Berghoff LLP

(57) ABSTRACT

The disclosure provides a capture system and methods for isolating cysteine-containing peptides from biological fluid and proteolytic mixtures. The disclosure also provides compounds of formulae (II), (III), and (IV), useful in methods of the invention.

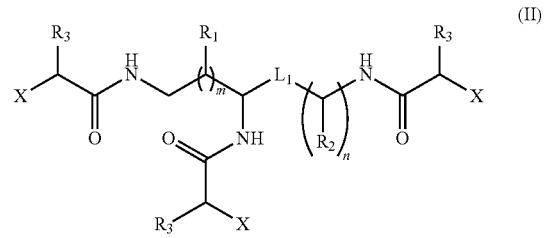

(II)

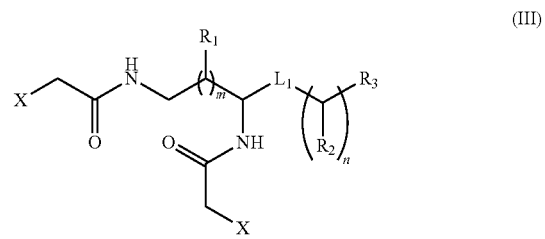

(III)

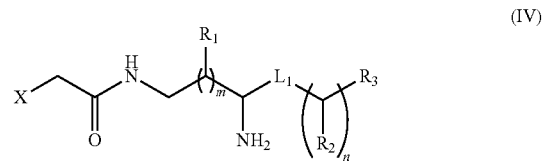

(IV)

4 Claims, 5 Drawing Sheets

(56) References Cited

OTHER PUBLICATIONS

Mabrouk et al., "Simultaneous oxytocin and arg-vasopressin measurements in microdialysates using capillary liquid chromatography—mass spectrometry," J Neurosci Methods. 209(1):127-33 (2012).

Robinson et al., "Validation of an enzyme-linked immunoassay (ELISA) for plasma oxytocin in a novel mammal species reveals potential errors induced by sampling procedure," J Neurosci Methods 226:73-9 (2014).

Sako et al., "Ribosomal synthesis of bicyclic peptides via two orthogonal inter-side-chain reactions," J. Am. Chem. Soc. 130 (23):7232-7234 (2008).

Szeto et al., "Evaluation of enzyme immunoassay and radioimmunoassay methods for the measurement of plasma oxytocin," Psychosom Med. 73(5):393-400 (2011).

Thoma et al. "Nanomolar E-selectin inhibitors: 700-fold potentiation of affinity by multivalent ligand presentation,"J. Am. Chem. Soc. 123(41):10113-10114 (2001).

Turkman et al., "Radiosynthesis of N5-[18F]fluoroacetylomithine (N5-[18F]FAO) for PET imaging of ornithine decarboxylase (ODC) in malignant tumors," J. Label Compd. Radiopharm 53:33-37 (2011).

Villain et al., "Covalent capture: A new tool for the purification of synthetic and recombinant polypeptides," Chem Biol. 8(7):673-9 (2001).

Zhang et al., "Ultra sensitive quantitation of endogenous oxytocin in rat and human plasma using a two-dimensional liquid chromatography—tandem mass spectrometry assay," Anal Biochem. 416(1):45-52 (2011).

European Patent Office Action for Application No. 12716869.8; dated Jul. 26, 2016, pp. 1-5.

International Search Report of the International Search Authority corresponding to Application No. PCT/US2012/032416; mailed Jun. 27, 2012 pp. 1-4.

Written Opinion of the International Search Authority corresponding to Application No. PCT/US2012/032416; mailed Jun. 27, 2012 pp. 1-9.

International Preliminary Report on Patentability corresponding to Application No. PCT/US2012/032416; mailed Oct. 8, 2013 pp. 1-10.

Mclaughlin, et al. "Quantitative analysis of oxytocin and vasopressin by LC-MS / MS." 56th ASMS Conference on Mass Spectrometry (p. 8). Denver: Stanford University Mass Spectrometry Facility (2008).

Waters. "Peptide and Protein Bioanalysis Application Notebook," available on-line Feb. 2015.

\* cited by examiner

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Cleaved peptide
<220> FEATURE:
<221> NAME/KEY: MISC_FEATURE
<222> LOCATION: (6)..(6)
<223> OTHER INFORMATION: carboxymethyl

<400> SEQUENCE: 1

Thr Val Thr Leu Asp Cys Val Asn Glu Arg
1               5                   10
```

ISOLATION OF CYSTEINE CONTAINING PEPTIDES

FIELD OF THE INVENTION

The disclosure provides a capture system and methods from isolating cysteine-containing peptides from biological fluid (e.g. whole blood, plasma, serum, buffy coat, saliva, sweat and urine) and proteolytic mixtures.

BACKGROUND OF THE INVENTION

The blood plasma proteome provides a wide window into the dynamics of the protein and peptide components of human health over a lifespan. Quantitative analysis of peptide features in this window by mass spectrometry in concert with clinical diagnoses forms the basis of disease biomarker identification. Acquiring plasma biomarkers for specific cancers enables relatively cheap and noninvasive cancer screening. Inexpensive, noninvasive cancer screens are broadly applied and diagnose cancer earlier in disease progression. Earlier diagnosis is highly correlated with better treatment outcome.

The plasma proteome presents a significant challenge for fractionation technologies. The concentration of highly abundant plasma proteins and peptides exceeds the lowest abundance species by ten orders of magnitude. Detecting low abundant species in plasma in a systematic way requires a technology that enriches efficiently, has high recovery and capacity, can accommodate high loading levels, is high-throughput and can isolate multiple species from a single sample without specific protocols developed for each desired peptide.

Fractionating the plasma proteome in an unbiased way may be performed by 2D gel electrophoresis or mixed-mode (ion-exchange solid phase in-line with hydrophobic (i.e., C-18) solid phase) ultra-performance liquid chromatography (UPLC): both have reasonable enrichment but tolerate only low loading volumes. The electrophoresis method and may be pursued in parallel but has appreciable sample loss, the opposite is true for the UPLC approach. If the target if interest is known, the plasma proteome may be assayed in a directed way by solid phase extraction or counter-current chromatography. The first approach is limited by low specificity and loading volume, the second is slow, low throughput and also limited by low-loading volumes.

SUMMARY OF THE INVENTION

Plasma fractionation by immunoaffinity chromatography achieves dramatic enrichment from samples loaded at high levels and is readily adapted to high-throughput approaches. The principal drawbacks are the requirement for advance knowledge of the target and low capacity and low target recovery. The enrichment stems from the specificity of protein structure recognition possible with high affinity monoclonal antibodies. These antibodies are coupled to a solid support and added to plasma in batch, easily accommodating high loading levels. Low recovery arises from low penetration of solid support by target peptide, inefficient presentation of antibody to target, from the extensive washing necessary for sufficient enrichment and incomplete elution as a result of particularly stable protein interactions or anomalous coupling of target to solid support. This loss is tolerated at preparative scales and when acquisition of an unmodified peptide is necessary.

The enrichment achieved by the recognizing target peptide structure is accessible in another way. Protein structure perturbs the intrinsic reactivity of amino acid functional groups, i.e., it is very difficult to modify every carboxylic acid functional group in a protein without denaturant. From the point of view of fractionation this reactivity heterogeneity is a feature. It is possible to modify some amino acids on some proteins in a mixture while identical functional groups in structurally distinct environments remain unmodified. If the target functional group is sufficiently low in abundance reactivity homologues will be rare enough that their isolation will lead to considerable enrichment. Enrichment that is achievable without any foreknowledge of target structure or even identity.

Cysteine is the second least abundant amino acid. The thiol nucleophile of cysteine is the most readily alkylated functional group at plasma pH, contained in the genetically encoded amino acids. Cysteine also frequently occurs in oxidized disulfide pairs. Cysteinyl thiols in disulfides are chemically protected from alkylation and possible to deprotect under mild reducing conditions. Reducing disulfide thiols is a powerful additional axis of control for fractionation. Both the free thiol and the protected disulfides may have their intrinsic reactivity further modulated by the addition of denaturant or detergent. Fractionation is possible by contacting a thiol reactive solid phase with peptides under reaction conditions that support native protein structure, removing the solid phase, and replacing it with fresh solid phase in the presence of denaturant or detergent that perturb the intrinsic reactivities of structured thiols.

Covalent capture of target peptides affords other advantages in addition to achieving considerable enrichment. It may be irreversible under wash conditions, decoupling recovery and wash stringency. Furthermore, unlike preparative work, where chemical modification of target is unwanted, in analytical work it is irrelevant. This is especially true in mass spectrometry experiments where trace amounts of target are not recovered and the covalent modification is usually trivial to account for in the mass analysis. However, covalent capture of target, peptides on conventional solid support matrices is subject to the same drawbacks that beset immunoaffinity resins. The reactive functionalities must be well presented to the target not occluded. Efficient presentation of reactivity to target is achieved with polyethylene glycol succinate linear polyester linker segments presenting the thiol reactive groups.

Covalent capture approaches would further exceed current approaches if anomalous binding and coupling to solid phase may be minimized. To ensure complete elution of covalently captured material it would be ideal to be able to dissolve the solid phase of the capture resin into material that would be transparent to subsequent analysis. We achieve this by generating a polyester solid phase comprised of hydrophilic polyacids and poly alcohols that may be base hydrolyzed (along with the polyester linker) to highly water soluble monomers. After neutralization, these resin hydrosylates may be injected directly unto reverse phase matrices where the targets will adsorb but the resin monomers will be washed away under target trapping conditions.

Another method for the chemical fractionation and isolation of cysteinyl peptides of interest from complex samples like serum, saliva, milk and cerebral spinal fluid is described. The method of the disclosure may be used to systematically fractionate the all the cysteinyl peptides an entire sample and specific enough to isolate species of low abundance. The method of the disclosure exploits the nucleophilic reactivity of cysteinyl thiols and the diverse modes naturally employed to protect cysteinyl thiols from chemical modification. Cysteinyl thiols are sufficiently nucleophilic under chemically reducing and protein structure denaturing conditions that cysteinyl thiols may be alkylated to completion with an excess of an alpha-halo acetamido group. Natural peptides and proteins protect cysteinyl thiols from modification sterically, burying them in the three-dimensional structure, chemically, oxidizing them into disulfides, and by using both strategies at once.

As complex biological samples contain different cysteinyl proteins and peptides exploiting these thiol protection strategies in different ways we will isolate specific thiols in a cap with excess, quench, modify to completion with molar excess, clear excess reagent and orthogonal capture strategy reminiscent of solid phase peptide synthesis. First to limit the effect of other nucleophilic species we will acetylate the mixture with acetic anhydride. Under relatively non-reducing, non-denaturing conditions we will alkylate accessible cysteinyl thiols with an alkylating reagent in sufficient excess to drive the reaction to completion. The excess alkylating reagent quenches by reacting intramolecularly in a rate that is slower than thiol alkylation. After the quench reaction has proceeded to completion we increase the concentration of the denaturant and reducing agent and subject the sample to either or two thiol capture reagents.

If a peptide containing a single thiol is desired, then a reagent containing two thiol reactive electrophiles of different reactivity, like the iodoacetamido and chloroacetamido groups together is added to the sample. Single thiols are alkylated by the iodoacetamido group and present the chloroacetamido group for capture. Thiols in exposed and reduced disulfides are alkylated by both groups and are transparent to capture. Excess alkylation reagent is cleared with the judicious addition of propylamine at a concentration and pH sufficient for alkylation of the propyl amine primary amine by iodoacetamido but not the chloroacetamido group. The chloroacetamido group on the excess reagent that alkylated propylamine alkylates the secondary amine product of the first propylamine alkylation as secondary amine reaction is faster generally and here intramolecular. Only the chloroacetamido groups whose iodoacetamido groups are consumed alkylating desired, exposed thiols remain presenting a chemically orthogonal group (chloroacetamido groups are rare in biological systems). We capture the chloroacetamido groups with a thiol covalently attached to solid support through a cleavable linkage. As the naturally occurring thiols in the mixture exposed under the current conditions have been alkylated a resin bound thiol is the logical functional group to use to capture peptides. The competing thiols have been capped.

If peptide containing a disulfide is desired, then a reagent containing three thiol reactive electrophiles with at least one of slower reactivity than the other two, like the iodoacetamido and chloroacetamido groups together is added to the sample. Single thiols are alkylated by the iodoacetamido group and present another iodoacetamido and the chloroacetamido group. Reduced disulfide thiols are alkylated usually by the iodoacetamido groups on the same alkylating agent and present the chloroacetamido group for capture. Excess alkylation reagent as well as alkylating agent attached single thiols will be cleared with the judicious addition of ammonium hydroxide at a concentration and pH sufficient for alkylation of the ammonium hydroxide amine by iodoacetamido but not the chloroacetamido group. The alkylating reagent coupled to a single thiol will clear in a manner similar to the two alpha-halo group excess alkylating reagent cleared above. The second iodoacetamido group on excess reagent alkylates the newly formed glycinamide structure intramolecularly and the chloroacetamido group alkylates the secondary amine product of the ammonia dialkylation as that reaction is faster generally and here intramolecular.

Thus, in one aspect, the disclosure provides a method for isolating a protein, the method comprising reacting a cysteine moiety of a protein. Another aspect, the disclosure provides a method for isolating a protein, the method comprising reacting a cysteine moiety of a protein with a capture system.

In another aspect, the disclosure provides a capture system of formula (I):

wherein

R' is hydrogen or a solid support;

X' is absent or a polymer linker; and

Z' is a capture group, wherein the capture group is capable of reacting with a disulfide or a thiol group.

In another aspect, the disclosure provides a capture system of formula (I-A):

wherein

R is hydrogen or a solid support;

X is a polymer linker;

Y is a cleavable linker; and

Z is a capture group, wherein the capture group comprises a disulfide or a thiol group.

In another aspect, the disclosure provides a compound of formula (II):

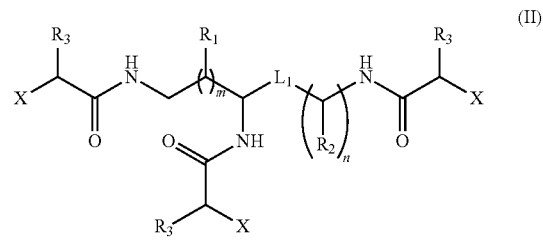

or a pharmaceutically acceptable salt thereof.

Yet in another aspect, the disclosure provides a compound of formula (III):

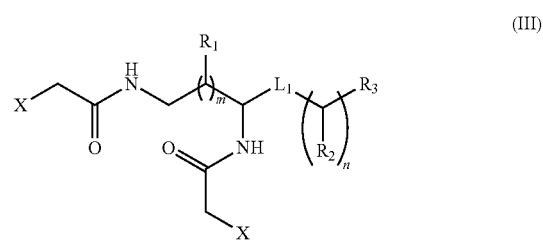

or a pharmaceutically acceptable salt thereof.

In another aspect, the disclosure provides a compound of formula (IV):

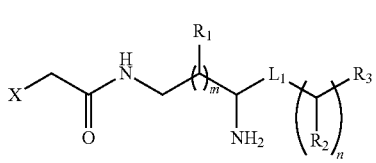

or a pharmaceutically acceptable salt thereof.

In one aspect of the invention, the disclosure provides a method for isolating proteins.

One such method comprises:
1) contacting capture system of formula (I) with a biological fluid to obtain captured proteins; and
2) cleaving the captured proteins.

Another such method comprises:
1) contacting a biological fluid with a compound of formula (II) to obtain cross-linked proteins;
2) activating a capture system of formula (I-A);
3) contacting activated capture system with the cross-linked protein to obtain captured proteins; and
4) cleaving the captured proteins.

DESCRIPTION OF DRAWINGS

The results set forth herein, and the properties and characteristics of the methods provided by the disclosure, can be advantageously understood with regard to the drawings.

FIG. 1A shows elutions from unfunctionalized resin (no capture group). 1 is elute of plasma loaded in buffer; 2 is elute of plasma loaded in Triton X-100; 3 is elute of plasma loaded in SDS; 4 is Triton X-100 was of plasma load; 5 is SDS wash of plasma load; 6 is buffer flow-through; 7 is Triton X-100 flow-through, and 8 is SDS flow-through.

DETAILED DESCRIPTION OF THE INVENTION

Figure 1A:
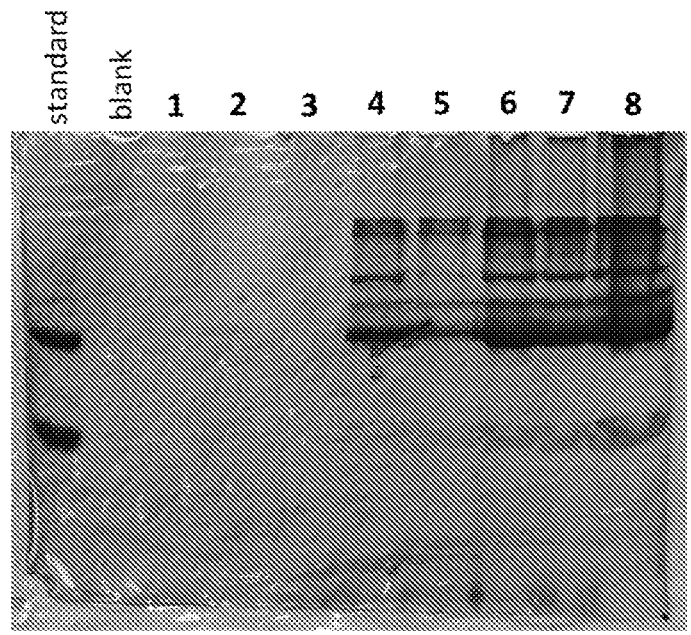
Figure 1B:
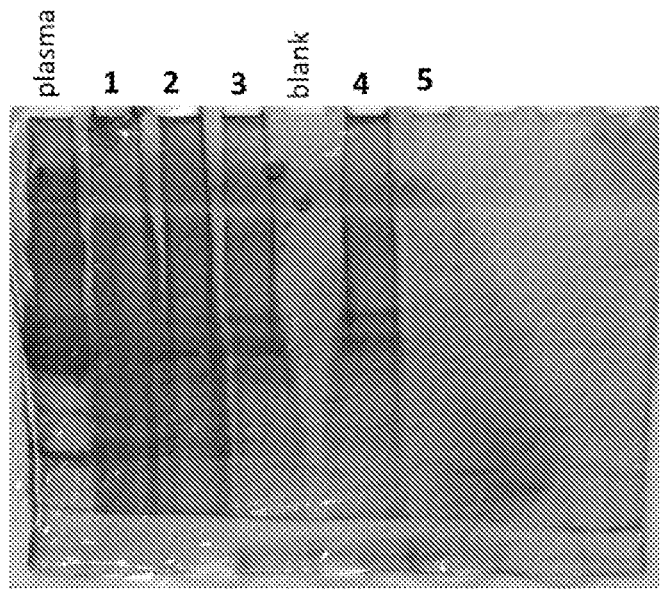
FIG. 1B shows elutions from alpha-iodoaceto (i.e., —C(O)CH$_2$I) functionalized resin fractionated plasma. Plasma is the plasma load; 1 is elute of plasma loaded in buffer; 2 is elute of 1 flow through loaded on resin with 5 mM ascorbic acid; 3 is elute of 2 flow through loaded in buffer with 1 mM TCEP; 4 is elute of 3 flow through loaded in buffer with 0.01% of SDS; and 5 is elute of 3 flow through loaded in buffer with 0.1% of SDS.

Thus, in one aspect, the disclosure provides a method for isolating a protein, the method comprising reacting a cysteine moiety of a protein. Another aspect, the disclosure provides a method for isolating a protein, the method comprising reacting a cysteine moiety of a protein with a capture system. In both aspects, the protein may be structured (i.e., folded or in native state) or in tunable unstructured states. In one embodiment, the reacting of the cysteine moiety comprises alkylation. In another embodiment, the alkylation of the cysteine moiety is differential alkylation. In one embodiment, the method further comprises eluting the protein by hydrolyzing the capture system. In another embodiment, hydrolyzing the capture system is under basic conditions. In yet another embodiment, hydrolyzing the capture system is under acidic conditions.

In one aspect, the disclosure provides a capture system of formula (I-A):

$$R—X—Y—Z \quad (I-A)$$

wherein
R is hydrogen or a solid support;
X is a polymer linker;
Y is a cleavable linker; and
Z is a capture group, wherein the capture group comprises a disulfide or a thiol group.

In one embodiment, the disclosure provides the capture system, wherein R is hydrogen.

In another embodiment, the disclosure provides the capture system, wherein R is a solid support. In one embodiment, the solid support is a polymer resin. In another embodiment, the solid support is glass.

In one embodiment, the disclosure provides the capture system of formula (I-A), wherein the solid support comprises a copolymer of polyalcohol and polycarboxylic acid monomers. In one embodiment, the copolymer may be capped or uncapped.

Representative polyalcohols include, but are not limited to, glycol, glycerol, erythritol, threitol, arabitol, xylitol, ribitol, mannitol, sorbitol, dulcitol, fucitol, iditol, inositol, isomalt, maltitol, lactitol, polyglycitol, 1,2-propanediol, 1,2-butanediol, 2,3-butanediol, 1,3-butanediol, 1,2-pentanediol, etohexadiol, p-menthane-3,8-diol, and 2-methyl-2,4-pentanediol.

Representative polycarboxylic acids include, but are not limited to, citric acid, isocitric acid, aconitic acid, tricarballylic acid, trimesic acid, mellitic acid, oxalic acid, malonic acid, succinic acid, glutaric acid, adipic acid, pimelic acid, suberic acid, azelaic acid, sebacic acid, undecanedioic acid, dodecanedioic acid, phthalic acid, isophthalic acid, terephthalic acid, maleic acid, fumaric acid, glutaconic acid, traumatic acid, and muconic acid.

In another embodiment, the disclosure provides the capture system of formula (I-A), wherein the solid support comprises a copolymer of sorbitol and citric acid.

In another embodiment, the disclosure provides the capture system of formula (I-A), wherein the solid support comprises a copolymer of sorbitol and citric acid, further comprising triethyleneglycol. In another embodiment, triethylene glycol is a cap for the unreacted carboxylic acid groups.

In another embodiment, the disclosure provides the capture system of formula (I-A), wherein the solid support comprises a copolymer of glycerol and citric acid. In another embodiment, the solid support comprises a copolymer of glycerol, citric acid and triethylene citrate as a plasticizer.

In one embodiment, the disclosure provides the capture system of formula (I-A), wherein the solid support comprises a copolymer of polyalcohol and carboxylic acid monomers, and further includes polyether. Representative polyethers are described below with reference to the polymer linker. In one embodiment, polyether is a cap for the unreacted carboxylic acid groups.

In one embodiment, the disclosure provides the capture system of formula (I-A), wherein the solid support comprises a copolymer comprised of polyalcohol and polyacid.

Representative polyalcohols are described above. Representative polyacids include, but are not limited to, polyacrylic acid, polyacrylic acid sodium salt, poly(acrylic acid-co-maleic acid), poly(methyl vinyl ether-alt-maleic acid), poly (acrylamide-co-acrylic acid), poly(lactic acid), poly(glycolic acid).

In one embodiment, the disclosure provides the capture system as described above, wherein the polymer linker is a polyether. In one embodiment, the polyether is triethylene glycol, tetraethylene glycol, polyethylene glycol, polypropylene glycol, polytetramethylene glycol, polyoxymethylene, or a combination thereof. In another embodiment, the polyether is polyethylene glycol, polypropylene glycol, or a combination thereof. In one embodiment, the polyether is polyethylene glycol. In another embodiment, the polyether is polypropylene glycol.

In one embodiment, the disclosure provides the capture system of formula (I-A) as described above, wherein the polymer linker is a linear copolymer comprising polyether. In one embodiment, the polyether is triethyleneglycol, polyethylene glycol, polypropylene glycol, polytetramethylene glycol, polyoxymethylene, or a combination thereof. In another embodiment, the polyether is polyethylene glycol, polypropylene glycol, or a combination thereof. In one embodiment, the polyether is polyethylene glycol. In another embodiment, the polyether is polypropylene glycol.

In one embodiment, the disclosure provides the capture system of formula (I-A) as described above, wherein the polymer linker is a linear copolymer comprising polyether and polycarboxylic acid monomers. Representative examples of polyethers and polycarboxylic acids are discussed above. In another embodiment, the copolymer is a linear copolymer.

In one embodiment, the disclosure provides the capture system as described above, wherein the polymer linker has a molecular weight of no more than 20,000. In one embodiment, the polymer linker has a molecular weight of no more than 10,000. In another embodiment, the polymer linker has a molecular weight between about 500 and 5,000. In yet another embodiment, the polymer linker has a molecular weight between about 1,000 and 3,000. In yet another embodiment, the polymer linker has a molecular weight between about 500 and 1,500.

In one embodiment, the disclosure provides the capture system as described above, wherein the cleavable linker is connected to the capture group through an ester.

In another embodiment, the disclosure provides the capture system as described above, wherein the cleavable linker is of formula:

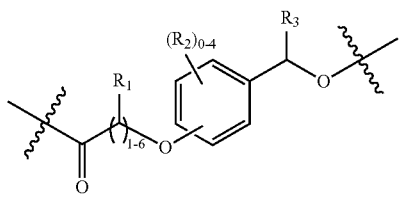

wherein
$R_1$ is independently H or $C_1$-$C_6$ alkyl;
$R_2$ is independently halogen, $NO_2$, $C_1$-$C_6$ alkyl, hydroxy, $C_1$-$C_6$ alkoxy, amino, ($C_1$-$C_6$ alkyl)amino, or di($C_1$-$C_6$ alkyl)amino; and
$R_3$ is H or $C_1$-$C_6$ alkyl.

In one embodiment, the disclosure provides the capture system as described above, wherein each $R_1$ and $R_3$ in the cleavable linker is H.

In one embodiment, the disclosure provides the capture system as described above, wherein the cleavable linker is of formula:

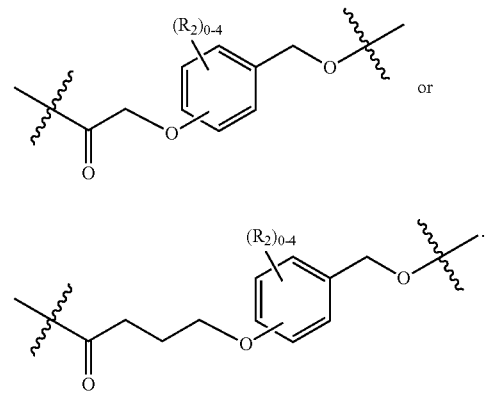

In one embodiment, $R_2$ is independently halogen, $NO_2$, $C_1$-$C_6$ alkyl, hydroxy, $C_1$-$C_6$ alkoxy, amino, ($C_1$-$C_6$ alkyl) amino, or di($C_1$-$C_6$ alkyl)amino.

In one embodiment, the disclosure provides the capture system as described above, wherein the cleavable linker is of formula:

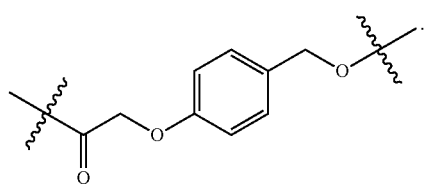 [SMILES: *OCc1ccc(OCC(*)=O)cc1]

In another embodiment, the disclosure provides the capture system as described above, wherein the cleavable linker is of formula:

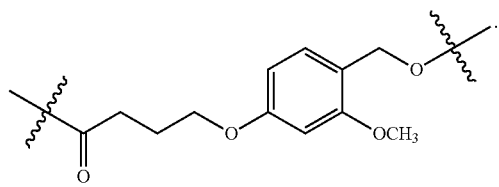 [SMILES: *OCc1ccc(OCCCC(*)=O)cc1OC]

In one embodiment, the disclosure provides the capture system as described above, wherein the capture group comprises disulfide or a thiol group, a hydrophobic moiety, and a reporter moiety. The reporter moiety, when cleaved, can optionally absorbs lights in the visible wavelength range.

In another embodiment, the disclosure provides the capture system as described above, wherein the capture group is of formula:

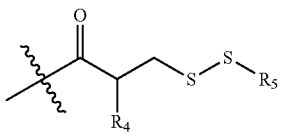

wherein

R$_4$ is C$_1$-C$_6$ alkyl, aryl, heteroaryl, aryl(C$_1$-C$_6$ alkyl), heteroaryl(C$_1$-C$_6$ alkyl), —OR$_6$, —NHR$_6$, —N(R$_6$)$_2$, —NHC(O)R$_6$, —NHC(O)OR$_6$, —C(O)R$_6$, —C(O)OR$_6$, or —OC(O)R$_6$, R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino; and R$_5$ is hydrogen, aryl or heteroaryl, wherein each is optionally substituted with halogen, NO$_2$, C$_1$-C$_6$ alkyl, hydroxy, C$_1$-C$_6$ alkoxy, amino, (C$_1$-C$_6$ alkyl)amino, or di(C$_1$-C$_6$ alkyl)amino.

In another embodiment, R$_5$ is aryl optionally substituted with halogen, NO$_2$, C$_1$-C$_6$ alkyl, hydroxy, C$_1$-C$_6$ alkoxy, amino, (C$_1$-C$_6$ alkyl)amino, or di(C$_1$-C$_6$ alkyl)amino. In yet another embodiment, R$_5$ is heteroaryl optionally substituted with halogen, NO$_2$, C$_1$-C$_6$ alkyl, hydroxy, C$_1$-C$_6$ alkoxy, amino, (C$_1$-C$_6$ alkyl)amino, or di(C$_1$-C$_6$ alkyl)amino. In one embodiment, R$_5$ is hydrogen.

In one embodiment, the disclosure provides the capture system as described above, wherein R$_4$ of the capture group is:

C$_1$-C$_6$ alkyl, aryl, heteroaryl, aryl(C$_1$-C$_6$ alkyl), heteroaryl(C$_1$-C$_6$ alkyl), —OR$_6$, —NHR$_6$, —N(R$_6$)$_2$, —NHC(O)R$_6$, —NHC(O)OR$_6$, —C(O)R$_6$, —C(O)OR$_6$, or —OC(O)R$_6$; and R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino.

In another embodiment, R$_4$ is —OR$_6$, —NHR$_6$, —N(R$_6$)$_2$, —NHC(O)R$_6$, —NHC(O)OR$_6$, —C(O)R$_6$, —C(O)OR$_6$, or —OC(O)R$_6$; and R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino.

In one embodiment, R$_4$ is —NHR$_6$, —N(R$_6$)$_2$, —NHC(O)R$_6$, or —NHC(O)OR$_6$; and R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino.

In another embodiment, R$_4$ is —NHC(O)R$_6$ or —NHC(O)OR$_6$; and

R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino.

In one embodiment, the disclosure provides the capture system as described above, wherein R$_4$ is —NHC(O)R$_6$ or —NHC(O)OR$_6$;

R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino; and R$_5$ is heteroaryl optionally substituted with halogen, NO$_2$, C$_1$-C$_6$ alkyl, hydroxy, C$_1$-C$_6$ alkoxy, amino, (C$_1$-C$_6$ alkyl) amino, or di(C$_1$-C$_6$ alkyl)amino.

In one embodiment, the disclosure provides the capture system as described above, wherein the cleavable linker and the capture group are of formula:

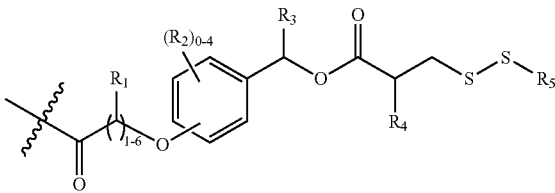

wherein

R$_1$ is H or C$_1$-C$_6$ alkyl;

R$_2$ is halogen, NO$_2$, C$_1$-C$_6$ alkyl, hydroxy, C$_1$-C$_6$ alkoxy, amino, (C$_1$-C$_6$ alkyl)amino, or di(C$_1$-C$_6$ alkyl)amino;

R$_3$ is H or C$_1$-C$_6$ alkyl;

R$_4$ is C$_1$-C$_6$ alkyl, aryl, heteroaryl, aryl(C$_1$-C$_6$ alkyl), heteroaryl(C$_1$-C$_6$ alkyl), —OR$_6$, —NHR$_6$, —N(R$_6$)$_2$, —NHC(O)R$_6$, —NHC(O)OR$_6$, —C(O)R$_6$, —C(O)OR$_6$, or —OC(O)R$_6$, R$_6$ is C$_1$-C$_6$ alkyl, aryl, or aryl(C$_1$-C$_6$ alkyl), wherein each is optionally substituted with halogen, NO$_2$, C$_1$-C$_6$ alkyl, hydroxy, C$_1$-C$_6$ alkoxy, —OC(O)C$_1$-C$_6$ alkyl, amino, (C$_1$-C$_6$ alkyl)amino, or di(C$_1$-C$_6$ alkyl)amino; and R$_5$ is hydrogen, aryl or heteroaryl, wherein each is optionally substituted with halogen, NO$_2$, C$_1$-C$_6$ alkyl, hydroxy, C$_1$-C$_6$ alkoxy, amino, (C$_1$-C$_6$ alkyl)amino, or di(C$_1$-C$_6$ alkyl)amino.

In another embodiment, the disclosure provides the capture system as described above, wherein the cleavable linker and the capture group are of formula:

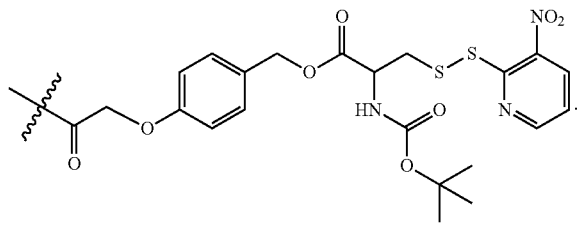 [SMILES: *C(=O)COc1ccc(COC(=O)C(CSSc2ncccc2[N+](=O)[O-])NC(=O)OC(C)(C)C)cc1]

In one embodiment, the disclosure provides the capture system as described above, which is of formula:

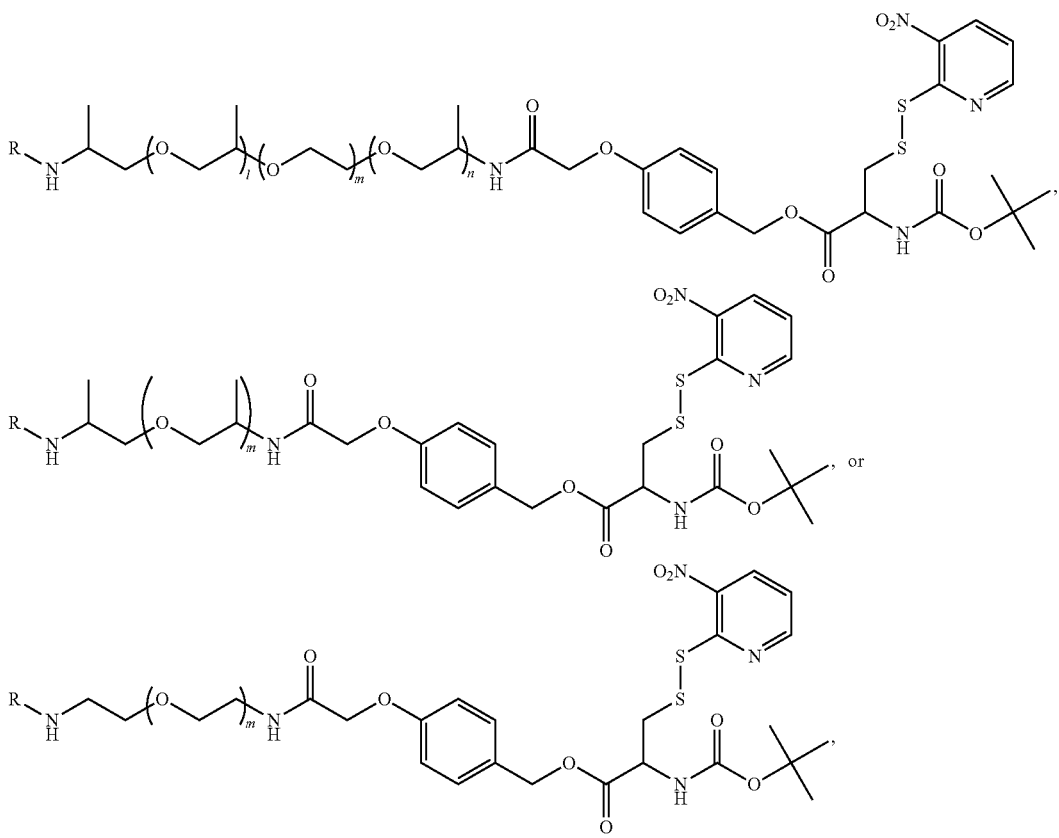

wherein
R is hydrogen or a solid support;
m is an integer between 2 and 50; and 1 and n are integers between 1 and 6.

In one aspect, the disclosure provides compounds of formula (II):

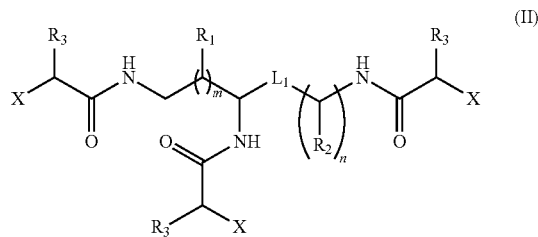

or a pharmaceutically acceptable salt thereof, wherein:
m is 1, 2, 3, 4, or 5;
n is 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_3$ is independently H, $C_1$-$C_6$ alkyl, $C_2$-$C_6$ alkenyl, or $C_2$-$C_6$ alkynyl; and each X is independently —F, —Cl, —Br, or —I, provided at least one X is different that remaining two X atoms, which can be the same or different.

In one embodiment, the disclosure provides compounds of formula (II), wherein m is 1, 2, 3, or 4. In another embodiment, m is 1, 2, or 3. In one embodiment, m is 1. In another embodiment, m is 2. In additional embodiment, m is 3.

In one embodiment, the disclosure provides compounds as described above with reference to formula (II), wherein n is 2 or 3. In one embodiment, n is 2.

In one embodiment, the disclosure provides compounds as described above with reference to formula (II), wherein $L_1$ is —C(O)NH—, —C(O)O—, —S(O)$_{0-2}$NH—, or —S(O)$_{0-2}$—. In one embodiment, $L_1$ is —C(O)NH—, —C(O)O—, or —S(O)$_{0-2}$NH—. In another embodiment, $L_1$ is —C(O)NH— or —C(O)O—. In another embodiment, wherein $L_1$ is —C(O)NH—.

In one embodiment, the disclosure provides compounds as described above with reference to formula (II), wherein each $R_1$ is independently H, $C_1$-$C_6$ alkyl, $C_2$-$C_6$ alkenyl, $C_2$-$C_6$ alkynyl, or $C_1$-$C_6$ alkoxy. In one embodiment, $R_1$ is independently H, $C_1$-$C_6$ alkyl, $C_2$-$C_6$ alkenyl, or $C_2$-$C_6$ alkynyl. In another embodiment, each $R_1$ is independently H or $C_1$-$C_6$ alkyl. In one embodiment, each $R_1$ is independently H. In additional embodiment, each $R_1$ is independently $C_1$-$C_6$ alkyl.

In one embodiment, the disclosure provides compounds as described above with reference to formula (II), wherein each $R_2$ is independently H, $C_1$-$C_6$ alkyl, $C_2$-$C_6$ alkenyl, $C_2$-$C_6$ alkynyl, or $C_1$-$C_6$ alkoxy. In one embodiment, each $R_2$ is independently H, $C_1$-$C_6$ alkyl, $C_2$-$C_6$ alkenyl, or $C_2$-$C_6$ alkynyl. In another embodiment, each $R_2$ is independently H or $C_1$-$C_6$ alkyl. Additionally, each $R_2$ is independently H. Also, each $R_2$ is independently $C_1$-$C_6$ alkyl.

In one embodiment, the disclosure provides compounds as described above with reference to formula (II), wherein each $R_3$ is independently H or $C_1$-$C_6$ alkyl. In one embodiment, each $R_3$ is hydrogen. In another embodiment, one of $R_3$ is $C_1$-$C_6$ alkyl, and other $R_3$ is H.

In one embodiment, the disclosure provides compounds as described above with reference to formula (II), wherein one X is —Cl, and two X are independently —I.

In another embodiment, the disclosure provides compounds as described above with reference to formula (II), wherein one X is —Cl, and two X are independently —Br.

In additional embodiment, the disclosure provides compounds as described above with reference to formula (II), wherein one X is —Cl, the other X is —Br, and the third X is —I.

In one embodiment, the disclosure provides compounds as described above with reference to formula (II), which is of formula (II-A), (II-B), or (II-C):

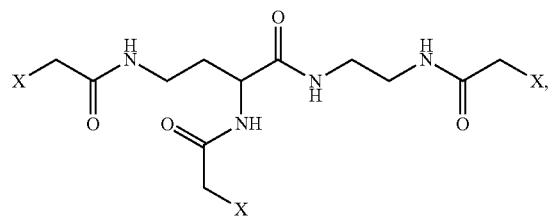
(II-A)

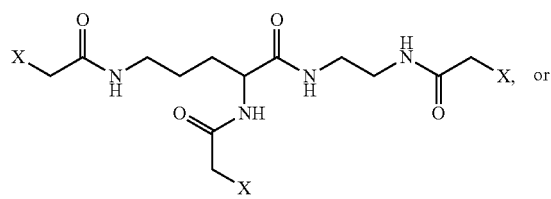
(II-B)

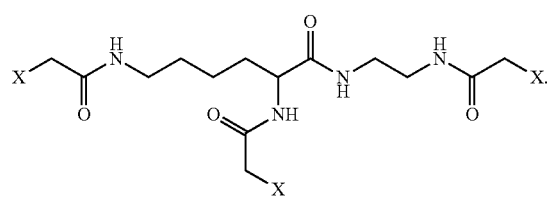
(II-C)

In one embodiment, the disclosure provides compounds as described above with reference to formulae (II-A), (II-B) or (II-C), wherein one X is —Cl, and two X are independently —I.

In another embodiment, the disclosure provides compounds as described above with reference to formulae (II-A), (II-B), or (II-C), wherein one X is —Cl, and two X are independently —Br.

In additional embodiment, the disclosure provides compounds as described above with reference to formulae (II-A), (II-B), or (II-C), wherein one X is —Cl, the other X is —Br, and the third X is —I.

In one embodiment, the disclosure provides a compound of formula (II), which is:

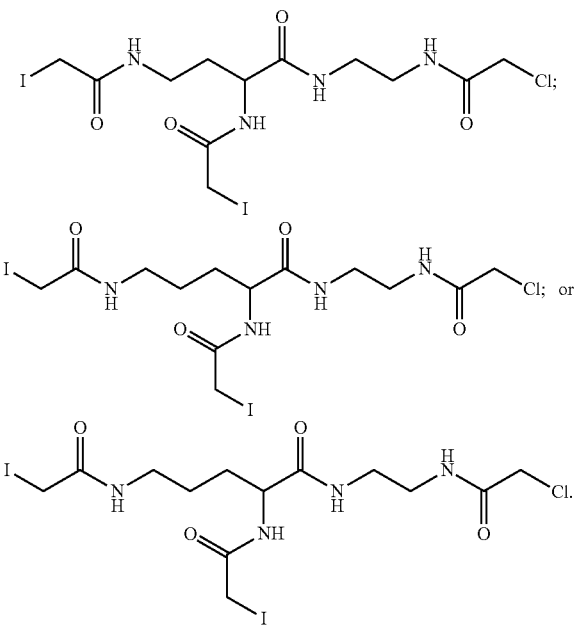

In one aspect, the disclosure provides compounds of formula (III):

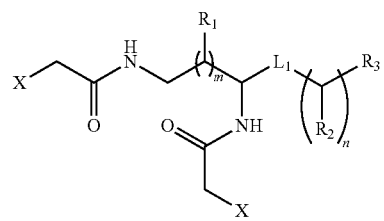
(III)

or a pharmaceutically acceptable salt thereof, wherein:
m is 1, 2, 3, 4, or 5;
n is 0, 1, 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
$R_3$ is H, $C_1$-$C_6$ alkyl, $C_2$-$C_6$ alkenyl, $C_2$-$C_6$ alkynyl, hydroxy, $C_1$-$C_6$ alkoxy, amino, ($C_1$-$C_6$ alkyl)amino, di($C_1$-$C_6$ alkyl)amino, or a fluorescent group, and wherein $R_3$ group can be isotopically labeled at available atoms; and
each X is independently —F, —Cl, —Br, or —I.

In one embodiment, the disclosure provides compounds of formula (III), wherein m is 1, 2, 3, or 4. In another embodiment, m is 1, 2, or 3. In one embodiment, m is 1. In another embodiment, m is 2. In additional embodiment, m is 3.

In one embodiment, the disclosure provides compounds as described above with reference to formula (III), wherein n is 1, 2 or 3. In one embodiment, n is 1. In another embodiment, n is 2.

In one embodiment, the disclosure provides compounds as described above with reference to formula (III), wherein $L_1$ is —C(O)NH—, —C(O)O—, —S(O)$_{0-2}$NH—, or —S(O)$_{0-2}$—. In one embodiment, $L_1$ is —C(O)NH—, —C(O)O—, or —S(O)$_{0-2}$NH—. In another embodiment, $L_1$ is —C(O)NH— or —C(O) O—. In another embodiment, wherein $L_1$ is —C(O)NH—.

In one embodiment, the disclosure provides compounds as described above with reference to formula (III), wherein each $R_1$ is independently H, $C_1$-$C_6$ alkyl, $C_2$-$C_6$ alkenyl, $C_2$-$C_6$ alkynyl, or $C_1$-$C_6$ alkoxy. In one embodiment, $R_1$ is independently H, $C_1$-$C_6$ alkyl, $C_2$-$C_6$ alkenyl, or $C_2$-$C_6$ alkynyl. In another embodiment, each $R_1$ is independently H or $C_1$-$C_6$ alkyl. In one embodiment, each $R_1$ is independently H. In additional embodiment, each $R_1$ is independently $C_1$-$C_6$ alkyl.

In one embodiment, the disclosure provides compounds as described above with reference to formula (II), wherein each $R_2$ is independently H or $C_1$-$C_6$ alkyl. In one embodiment, each $R_2$ is independently H. In another embodiment, each $R_2$ is independently $C_1$-$C_6$ alkyl.

In one embodiment, the disclosure provides compounds as described above with reference to formula (III), wherein $R_3$ is H, $C_1$-$C_6$ alkyl, hydroxy, $C_1$-$C_6$ alkoxy, amino, ($C_1$-$C_6$ alkyl)amino, di($C_1$-$C_6$ alkyl)amino, or a fluorescent group, and wherein $R_3$ group can be isotopically labeled at available atoms. In one embodiment, $R_3$ is H, $C_1$-$C_6$ alkyl, hydroxy, $C_1$-$C_6$ alkoxy, amino, ($C_1$-$C_6$ alkyl)amino, or di($C_1$-$C_6$ alkyl)amino.

In one embodiment, the disclosure provides compounds as described above with reference to formula (III), wherein $R_3$ is H or $C_1$-$C_6$ alkyl.

In one embodiment, the disclosure provides compounds as described above with reference to formula (III), wherein $R_3$ is hydroxy, $C_1$-$C_6$ alkoxy, amino, ($C_1$-$C_6$ alkyl)amino, or di($C_1$-$C_6$ alkyl)amino. In one embodiment, $R_3$ is hydroxy or $C_1$-$C_6$ alkoxy.

In one embodiment, the disclosure provides compounds as described above with reference to formula (III), wherein $R_3$ is amino, ($C_1$-$C_6$ alkyl)amino, or di($C_1$-$C_6$ alkyl)amino. In another embodiment, $R_3$ is amino.

In one embodiment, the disclosure provides compounds as described above with reference to formula (III), wherein $R_3$ is a fluorescent group. Fluorescent groups include, but are not limited to, fluorescein, rhodamine, Oregon green, eosin, Texas red, Cal Fluor dyes, cyanine, indocarbocyanine, oxacarbocyanine, thiacarbocyanine, merocyanine, Quasar dyes, dansyl and prodan derivatives, coumarin and its derivatives, pyridyloxazole, nitrobenzoxadiazole, benzoxadiazole, cascade, Nile red, Nile blue, cresyl violet, oxazine 170, proflavin, acridine orange, acridine yellow, auramine, crystal violet, malachite green, porphin, phtalocyanine, bilirubin, CF Dye®, BODIPY®, Alexa Fluor®, DyLight Fluor®, Atto®, Tracy®, FluoProbes®, MegaStokes Dyes® and derivatives thereof.

In one embodiment, the disclosure provides compounds as described above with reference to formula (III), wherein $R_3$ group can be isotopically labeled at available atoms. In one embodiment, $R_3$ is isotopically labeled lysine or ornithine derivative. For example, but not limited to L-Lysine-$^{13}C_6$, $^{15}N_2$, L-Lysine-$^{13}C_6$, and the like.

In one embodiment, the disclosure provides compounds as described above with reference to formula (III), wherein one X is —Cl, and other X is —I.

In one embodiment, the disclosure provides compounds as described above with reference to formula (III), wherein one X is —Cl, and other X is —Br.

In one embodiment, the disclosure provides compounds as described above with reference to formula (III), wherein both X are —I.

In one embodiment, the disclosure provides compounds as described above with reference to formula (III), wherein both X are —Br.

In one embodiment, the disclosure provides compounds as described above with reference to formula (III), which is of formula:

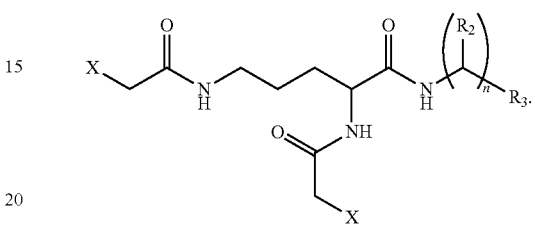

In one embodiment, the disclosure provides compounds as described above with reference to formula (III), which is of formula:

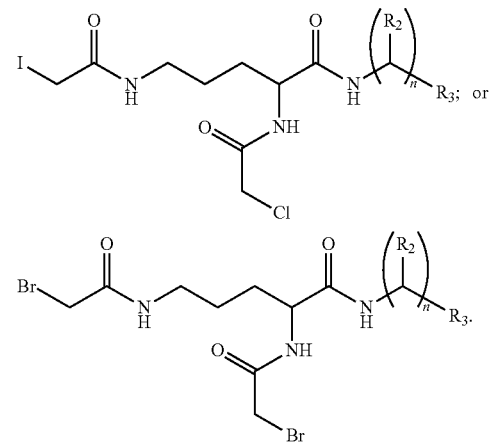

In one embodiment, the disclosure provides compounds of formula (III), which is:

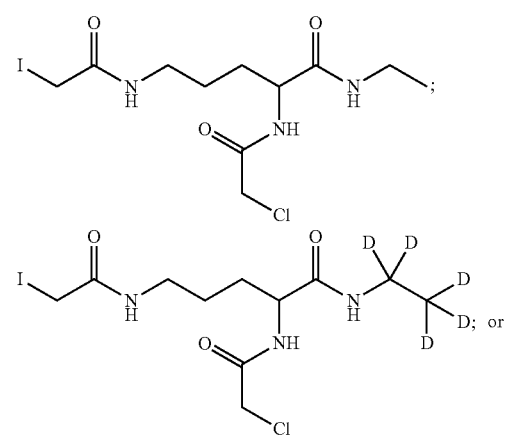

-continued

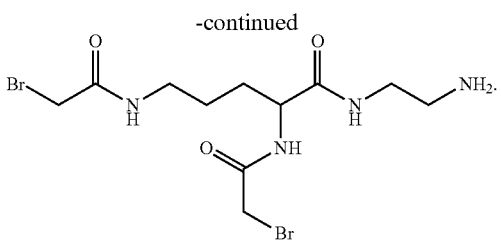

In one aspect, the disclosure provides compounds of formula (IV):

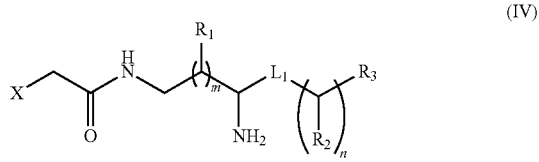

(IV)

or a pharmaceutically acceptable salt thereof, wherein:
m is 1, 2, 3, 4, or 5;
n is 1, 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
$R_3$ is H, $C_1$-$C_6$ alkyl, $C_2$-$C_6$ alkenyl, $C_2$-$C_6$ alkynyl, hydroxy, $C_1$-$C_6$ alkoxy, amino, ($C_1$-$C_6$ alkyl)amino, di($C_1$-$C_6$ alkyl) amino, or a fluorescent group, and wherein $R_3$ group can be isotopically labeled at available atoms; and
X is —F, —Cl, —Br, or —I.

In one embodiment, the disclosure provides compounds of formula (IV), wherein m is 1 or 2.

In one embodiment, the disclosure provides compounds as described above with reference to formula (IV), wherein n is 1 or 2.

In one embodiment, the disclosure provides compounds as described above with reference to formula (IV), wherein $L_1$ is —C(O)NH—.

In one embodiment, the disclosure provides compounds as described above with reference to formula (IV), wherein each $R_1$ is independently H or $C_1$-$C_6$ alkyl. In one embodiment, each $R_1$ is independently H. In another embodiment, each $R_1$ is independently $C_1$-$C_6$ alkyl.

In one embodiment, the disclosure provides compounds as described above with reference to formula (IV), wherein each $R_2$ is independently H or $C_1$-$C_6$ alkyl. In one embodiment, each $R_2$ is independently H. In another embodiment, each $R_2$ is independently $C_1$-$C_6$ alkyl.

In one embodiment, the disclosure provides compounds as described above with reference to formula (IV), wherein $R_3$ is H, $C_1$-$C_6$ alkyl, hydroxy, $C_1$-$C_6$ alkoxy, amino, ($C_1$-$C_6$ alkyl)amino, or di($C_1$-$C_6$ alkyl)amino. Also, $R_3$ is H or $C_1$-$C_6$ alkyl. In one embodiment, $R_3$ is H. In another embodiment, $R_3$ is $C_1$-$C_6$ alkyl.

In one embodiment, the disclosure provides compounds as described above with reference to formula (IV), wherein X is —Br.

In one embodiment, the disclosure provides a compound of formula (IV), which is:

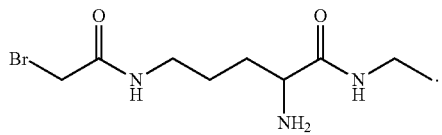

In one aspect, the disclosure provides a method for isolating proteins, the method comprising:
1) contacting the capture system of formula (I) with a biological fluid to obtain captured proteins; and
2) cleaving the captured proteins.

Biological fluid includes, but is not limited to whole blood, plasma, serum, buffy coat, saliva, sweat and urine.

In one embodiment, the disclosure provides a method wherein contacting results in reacting cysteine groups on the biological fluid with Z' group of formula (I) to obtain the captured proteins.

In one embodiment, the disclosure provides a method wherein cleaving the captured proteins comprises cleaving by an acid or a base. In another embodiment, the disclosure provides a method wherein cleaving the captured proteins hydrolizes the capture system.

In another aspect, the disclosure provides a method for isolating proteins, the method comprising:
1) contacting a biological fluid or a proteolytic mixture with a compound of formula (II) to obtain cross-linked proteins;
2) activating a capture system of formula (I-A);
3) contacting activated capture system with the cross-linked protein to obtain captured proteins; and
4) cleaving the captured proteins.

Biological fluid includes, but is not limited to whole blood, plasma, serum, buffy coat, saliva, sweat and urine.

In one embodiment, the disclosure provides a method wherein activating the capture system comprises cleaving a disulfide bond.

In one embodiment, the disclosure provides a method wherein cleaving the captured proteins comprises cleaving a cleavable linker.

In one embodiment, the disclosure provides a method further comprising first contacting the biological fluid with a compound of formula (III) or (IV) to block undesired disulfides.

In one embodiment, the disclosure provides a method wherein the compound of formula (II) is:

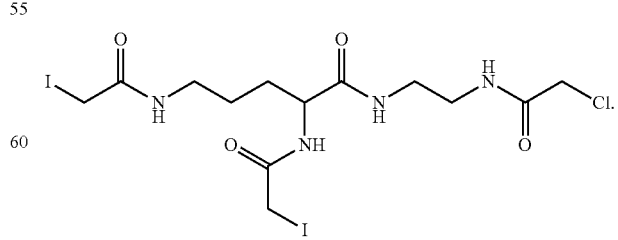

In one embodiment, the disclosure provides a method wherein the compound of formula (I-A) is:

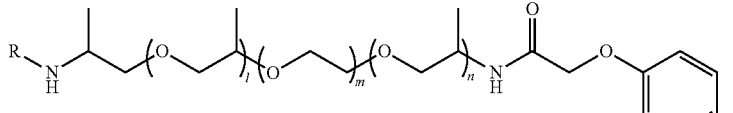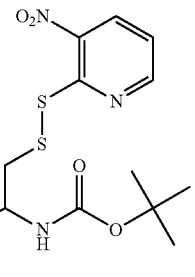

wherein
R is hydrogen or a solid support;
m is an integer between 2 and 50; and 1 and n are integers between 1 and 6.

In one aspect of the invention, the disclosure provides cross-linked molecule of formula (V):

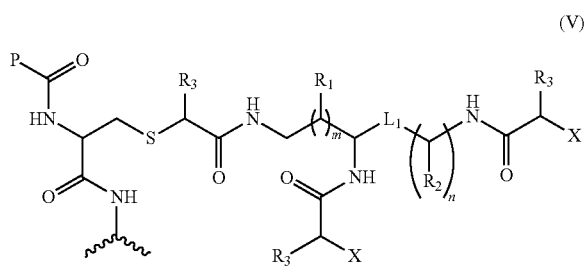

(V)

or a pharmaceutically acceptable salt thereof, wherein:
P is peptide, polypeptide, or protein;
m is 1, 2, 3, 4, or 5;
n is 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_3$ is independently H, $C_1$-$C_6$ alkyl, $C_2$-$C_6$ alkenyl, or $C_2$-$C_6$ alkynyl; and
each X is independently —F, —Cl, —Br, or —.

In one aspect of the invention, the disclosure provides cross-linked molecule of formula (VI):

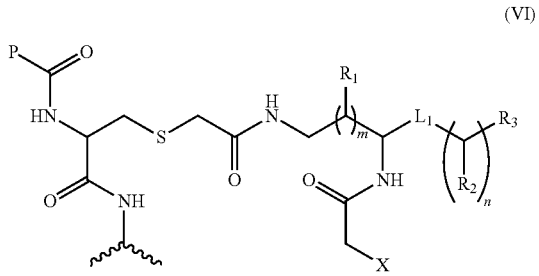

(VI)

or a pharmaceutically acceptable salt thereof, wherein:
P is peptide, polypeptide, or protein;
m is 1, 2, 3, 4, or 5;
n is 0, 1, 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
$R_3$ is H, $C_1$-$C_6$ alkyl, $C_2$-$C_6$ alkenyl, $C_2$-$C_6$ alkynyl, hydroxy, $C_1$-$C_6$ alkoxy, amino, ($C_1$-$C_6$ alkyl)amino, di($C_1$-$C_6$ alkyl)amino, or a fluorescent group, and wherein $R_3$ group can be isotopically labeled at available atoms; and
X is —F, —Cl, —Br, or —I.

In one aspect of the invention, the disclosure provides cross-linked molecule of formula (VII):

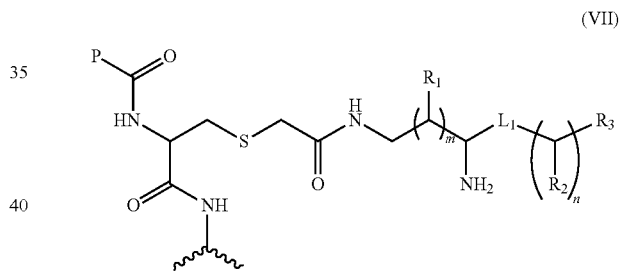

(VII)

or a pharmaceutically acceptable salt thereof, wherein:
P is peptide, polypeptide, or protein;
m is 1, 2, 3, 4, or 5;
n is 1, 2, 3, or 4;
$L_1$ is —C(O)NH—, —C(O)O—, —C(O)—, —S(O)$_{0-2}$NH—, —S(O)$_{0-2}$O—, or —S(O)$_{0-2}$—;
each $R_1$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino;
each $R_2$ is independently H, $C_1$-$C_6$ alkyl, $C_2$-$C_6$ alkenyl, $C_2$-$C_6$ alkynyl, $C_1$-$C_6$ alkoxy, ($C_1$-$C_6$ alkyl)amino, or di($C_1$-$C_6$ alkyl)amino; and
$R_3$ is H, $C_1$-$C_6$ alkyl, $C_2$-$C_6$ alkenyl, $C_2$-$C_6$ alkynyl, hydroxy, $C_1$-$C_6$ alkoxy, amino, ($C_1$-$C_6$ alkyl)amino, di($C_1$-$C_6$ alkyl)amino, or a fluorescent group, and wherein $R_3$ group can be isotopically labeled at available atoms.

In another aspect, the disclosure provides a capture system of formula (I):

R'—X'—Z'     (I)

wherein
R' is a solid support;
X' is absent or a polymer linker; and

Z' is a capture group, wherein the capture group is capable of reacting with a disulfide or a thiol group.

In one embodiment, the disclosure provides the capture system of formula (I), wherein R' is a solid support. In one embodiment, the solid support is a polymer resin. In another embodiment, the solid support is glass. In another embodiment, the solid support is polymer resin on glass.

In one embodiment, the disclosure provides the capture system of formula (I), wherein the solid support comprises a polymer that is water soluble. In another embodiment, the disclosure provides the capture system of formula (I), wherein the solid support comprises a polymer that is degradable under acidic or basic conditions. In yet another embodiment, the polymer is degradable under acidic conditions. In yet another embodiment, the polymer is degradable under basic conditions.

In one embodiment, the disclosure provides the capture system of formula (I) as described above, wherein the solid support comprises a polymer that is crosslinked or non-crosslinked polymer. In one embodiment, the polymer is crosslinked. In yet another embodiment, the polymer is crosslinked in high density.

In one embodiment, the disclosure provides the capture system of formula (I), wherein the solid support comprises a copolymer of polyalcohol and polycarboxylic acid monomers. In one embodiment, the copolymer may be capped or uncapped.

Representative polyalcohols include, but are not limited to, glycol, glycerol, erythritol, threitol, arabitol, xylitol, ribitol, mannitol, sorbitol, dulcitol, fucitol, iditol, inositol, isomalt, maltitol, lactitol, polyglycitol, 1,2-propanediol, 1,2-butanediol, 2,3-butanediol, 1,3-butanediol, 1,2-pentanediol, etohexadiol, p-menthane-3,8-diol, and 2-methyl-2,4-pentanediol.

Representative polycarboxylic acids include, but are not limited to, citric acid, isocitric acid, aconitic acid, tricarballylic acid, trimesic acid, mellitic acid, oxalic acid, malonic acid, succinic acid, glutaric acid, adipic acid, pimelic acid, suberic acid, azelaic acid, sebacic acid, undecanedioic acid, dodecanedioic acid, phthalic acid, isophthalic acid, terephthalic acid, maleic acid, fumaric acid, glutaconic acid, traumatic acid, and muconic acid.

In another embodiment, the disclosure provides the capture system of formula (I), wherein the solid support comprises a copolymer of sorbitol and citric acid.

In another embodiment, the disclosure provides the capture system of formula (I), wherein the solid support comprises a copolymer of sorbitol and citric acid.

In another embodiment, the disclosure provides the capture system of formula (I), wherein the solid support comprises a copolymer of sorbitol and citric acid, further comprising triethyleneglycol. In another embodiment, triethylene glycol is a cap for the unreacted carboxylic acid groups.

In another embodiment, the disclosure provides the capture system of formula (I), wherein the solid support comprises a copolymer of glycerol and citric acid. In another embodiment, the solid support comprises a copolymer of glycerol, citric acid and triethylene citrate as a plasticizer.

In one embodiment, the disclosure provides the capture system of formula (I), wherein the solid support comprises a copolymer of polyalcohol and carboxylic acid monomers, and further includes polyether. Representative polyethers are described below with reference to the polymer linker. In one embodiment, polyether is a cap for the unreacted carboxylic acid groups.

In one embodiment, the disclosure provides the capture system of formula (I), wherein the solid support comprises a copolymer comprised of polyalcohol and polyacid. Representative polyalcohols are described above. Representative polyacids include, but are not limited to, polyacrylic acid, polyacrylic acid sodium salt, poly(acrylic acid-co-maleic acid), poly(methyl vinyl ether-alt-maleic acid), poly(acrylamide-co-acrylic acid), poly(lactic acid), poly(glycolic acid). In one embodiment, the disclosure provides the capture system of formula (I) as described above, wherein X' is absent.

In one embodiment, the disclosure provides the capture system of formula (I) as described above, wherein X' is polymer linker.

In one embodiment, the disclosure provides the capture system as described in any reference to formula (I) above, wherein the polymer linker is a polyether. In one embodiment, the polyether is triethyleneglycol, tetraethylene glycol, polyethylene glycol, polypropylene glycol, polytetramethylene glycol, polyoxymethylene, or a combination thereof. In another embodiment, the polyether is polyethylene glycol, polypropylene glycol, or a combination thereof. In one embodiment, the polyether is polyethylene glycol. In another embodiment, the polyether is polypropylene glycol.

In one embodiment, the disclosure provides the capture system of formula (I) as described above, wherein the polymer linker is a linear copolymer comprising polyether. In one embodiment, the polyether is triethyleneglycol, polyethylene glycol, polypropylene glycol, polytetramethylene glycol, polyoxymethylene, or a combination thereof. In another embodiment, the polyether is polyethylene glycol, polypropylene glycol, or a combination thereof. In one embodiment, the polyether is polyethylene glycol. In another embodiment, the polyether is polypropylene glycol.

In one embodiment, the disclosure provides the capture system of formula (I) as described above, wherein the polymer linker is a linear copolymer comprising polyether and polycarboxylic acid monomers. Representative examples of polyethers and polycarboxylic acids are discussed above. In another embodiment, the copolymer is a linear copolymer.

In one embodiment, the disclosure provides the capture system of formula (I) as described above, wherein the polymer linker as described above has a molecular weight of no more than 20,000. In one embodiment, the polymer linker has a molecular weight of no more than 10,000. In another embodiment, the polymer linker has a molecular weight between about 500 and 5,000. In yet another embodiment, the polymer linker has a molecular weight between about 1,000 and 3,000. In yet another embodiment, the polymer linker has a molecular weight between about 500 and 1,500.

In one embodiment, the disclosure provides the capture system of formula (I) as described above, wherein the polymer linker is connected to the solid support through an ester.

In another embodiment, the disclosure provides the capture system of formula (I) as described above, wherein the polymer linker is of formula:

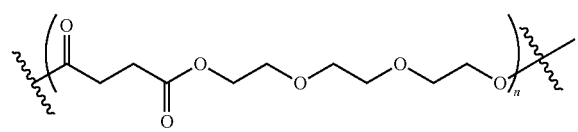

wherein n is 2-100. In one embodiment, n is 2-10. In another embodiment, n is 2-6. In yet another embodiment, n is 4.

In one embodiment, the disclosure provides the capture system of formula (I) as described above, wherein the polymer linker is of formula:

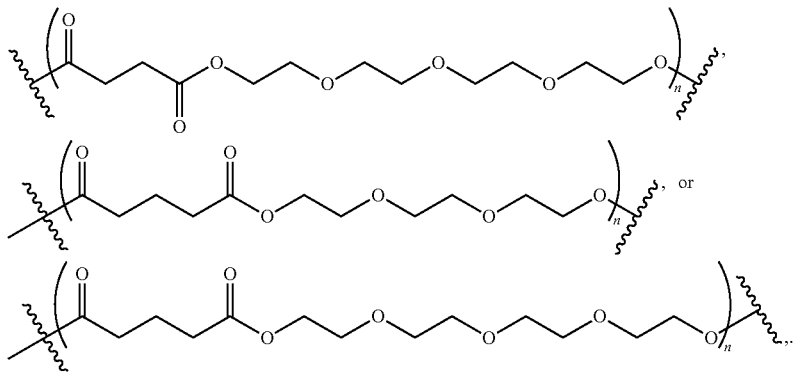

In one embodiment, the disclosure provides the capture system of formula (I) as described above, wherein Z' is a capture group, wherein the capture group is capable of reacts reacting with a disulfide or a thiol group under non-reducing, non-denaturing reaction conditions.

In another embodiment, the disclosure provides the capture system of formula (I) as described above, wherein the capture group is capable of reacts reacting with a disulfide or a thiol group under pH of about 6.0 to about 8.0 conditions.

In another embodiment, the disclosure provides the capture system as described in any reference to formula (I) above, wherein the capture group is of formula (VIII):

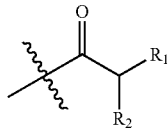

(VIII)

wherein
$R_1$ is halogen, $N_3$, —NHC(O)($C_1$-$C_6$ alkyl), —NHC(O)($C_1$-$C_6$ haloalkyl), —NHC(O)($C_1$-$C_6$ alkoxy), —NHC(O)($C_1$-$C_6$ halo alkoxy), —S(O)$_{0-2}$NH($C_1$-$C_6$ alkyl), —S(O)$_{0-2}$NH($C_1$-$C_6$ haloalkyl), —S(O)$_{0-2}$($C_1$-$C_6$ alkyl), —S(O)$_{0-2}$($C_1$-$C_6$ haloalkyl), —S(O)$_{0-2}$($C_1$-$C_6$ alkoxy), —S(O)$_{0-2}$($C_1$-$C_6$ haloalkoxy), —S(O)$_{0-2}$(aryl), —S(O)$_{0-2}$(arylalkyl), or —O—NHC(O)($C_1$-$C_6$ alkoxy); and
$R_2$ is hydrogen or —$C_1$-$C_6$ alkylene-NHC(O)($C_1$-$C_6$ haloalkyl);
or $R_1$ and $R_2$, together with a carbon atom to which they are attached, form aryl or heteroaryl ring, each substituted with $C_1$-$C_6$ alkyl, wherein such alkyl is optionally substituted with halogen, $N_3$, —NHC(O)($C_1$-$C_6$ alkyl), —NR$_3$C(O)($C_1$-$C_6$ haloalkyl), —NHC(O)($C_1$-$C_6$ alkoxy), —NR$_3$C(O)($C_1$-$C_6$ haloalkoxy), —S(O)$_{0-2}$NH ($C_1$-$C_6$ alkyl), —S(O)$_{0-2}$NH($C_1$-$C_6$ haloalkyl), —S(O)$_{0-2}$ ($C_1$-$C_6$ alkyl), —S(O)$_{0-2}$($C_1$-$C_6$ haloalkyl), —S(O)$_{0-2}$($C_1$-$C_6$ alkoxy), —S(O)$_{0-2}$($C_1$-$C_6$ haloalkoxy), —S(O)$_{0-2}$ (aryl), or —S(O)$_{0-2}$(arylalkyl).

In one embodiment, the disclosure provides the capture group of formula (VIII), wherein $R_1$ is halogen, $N_3$, —NHC (O)($C_1$-$C_6$ haloalkyl), —NHC(O)($C_1$-$C_6$ alkoxy), —NHC (O)($C_1$-$C_6$ haloalkoxy), —S(O)$_{0-2}$NH($C_1$-$C_6$ alkyl), —S(O)$_{0-2}$NH($C_1$-$C_6$ haloalkyl), —S(O)$_{0-2}$($C_1$-$C_6$ alkyl), —S(O)$_{0-2}$($C_1$-$C_6$ haloalkyl), —S(O)$_{0-2}$($C_1$-$C_6$ alkoxy), —S(O)$_{0-2}$($C_1$-$C_6$ haloalkoxy), —S(O)$_{0-2}$(arylalkyl), or —O—NHC(O)($C_1$-$C_6$ alkoxy).

In another embodiment, the disclosure provides the capture group of formula (VIII), wherein $R_1$ is halogen, $N_3$, —NHC(O)($C_1$-$C_6$ haloalkyl), or —O—NHC(O)($C_1$-$C_6$ alkoxy).

In another embodiment, the disclosure provides the capture group of formula (VIII), wherein $R_1$ is —S(O)$_{0-2}$NH ($C_1$-$C_6$ alkyl), —S(O)$_{0-2}$NH($C_1$-$C_6$ haloalkyl), —S(O)$_{0-2}$ ($C_1$-$C_6$ alkyl), —S(O)$_{0-2}$($C_1$-$C_6$ haloalkyl), —S(O)$_{0-2}$($C_1$-$C_6$ alkoxy), —S(O)$_{0-2}$($C_1$-$C_6$ haloalkoxy), or —S(O)$_{0-2}$(arylalkyl).

In one embodiment, the disclosure provides the capture group of formula (VIII), wherein $R_1$ is halogen. In another embodiment, $R_1$ is —Cl, —Br, or —I. In one embodiment, $R_1$ is —Cl or —I. In another embodiment, $R_1$ is —Cl. In additional embodiment, $R_1$ is —Br. In another embodiment, $R_1$ is —I.

In one embodiment, the disclosure provides the capture group of formula (VIII), wherein $R_1$ is $N_3$.

In another embodiment, the disclosure provides the capture group of formula (VIII), wherein $R_1$ is —NHC(O)($C_1$-$C_6$ haloalkyl). In one embodiment, $R_1$ is —NHC(O)CH$_2$X, wherein X is halogen. In another embodiment, $R_1$ is —NHC (O)CH$_2$Cl or —NHC(O)CH$_2$I.

In one embodiment, the disclosure provides the capture group of formula (VIII), wherein $R_1$ is —O—NHC(O)($C_1$-$C_6$ alkoxy). In one embodiment, $R_1$ is —O—NHC(O) (OtBu).

In one embodiment, the disclosure provides the capture group of formula (VIII) as described above, wherein $R_2$ is hydrogen.

In one embodiment, the disclosure provides the capture group of formula (VIII), wherein $R_1$ is halogen, $N_3$, —NHC (O)($C_1$-$C_6$ haloalkyl), —NHC(O)($C_1$-$C_6$ alkoxy), —NHC (O)($C_1$-$C_6$ haloalkoxy), —S(O)$_{0-2}$NH($C_1$-$C_6$ alkyl), —S(O)$_{0-2}$NH($C_1$-$C_6$ haloalkyl), —S(O)$_{0-2}$($C_1$-$C_6$ alkyl), —S(O)$_{0-2}$($C_1$-$C_6$ haloalkyl), —S(O)$_{0-2}$($C_1$-$C_6$ alkoxy), —S(O)$_{0-2}$($C_1$-$C_6$ haloalkoxy), —S(O)$_{0-2}$(arylalkyl), or —O—NHC(O)($C_1$-$C_6$ alkoxy); and $R_2$ is hydrogen.

In another embodiment, the disclosure provides the capture group of formula (VIII), wherein $R_1$ is halogen, $N_3$, —NHC(O)($C_1$-$C_6$ haloalkyl), or —O—NHC(O)($C_1$-$C_6$ alkoxy); and $R_2$ is hydrogen.

In another embodiment, the disclosure provides the capture group of formula (VIII), wherein $R_1$ is —$S(O)_{0-2}$NH ($C_1$-$C_6$ alkyl), —$S(O)_{0-2}$NH($C_1$-$C_6$ haloalkyl), —$S(O)_{0-2}$ ($C_1$-$C_6$ alkyl), —$S(O)_{0-2}$($C_1$-$C_6$ haloalkyl), —$S(O)_{0-2}$($C_1$-$C_6$ alkoxy), —$S(O)_{0-2}$($C_1$-$C_6$ haloalkoxy), or —$S(O)_{0-2}$(arylalkyl); and $R_2$ is hydrogen.

In one embodiment, the disclosure provides the capture group of formula (VIII), wherein $R_1$ is halogen and $R_2$ is hydrogen. In another embodiment, $R_1$ is —Cl, —Br, or —I and $R_2$ is hydrogen. In one embodiment, $R_1$ is —Cl or —I; and $R_2$ is hydrogen. In another embodiment, $R_1$ is —Cl and $R_2$ is hydrogen. In additional embodiment, $R_1$ is —Br and $R_2$ is hydrogen. In another embodiment, $R_1$ is —I and $R_2$ is hydrogen.

In one embodiment, the disclosure provides the capture group of formula (VIII), wherein $R_1$ is $N_3$ and $R_2$ is hydrogen.

In one embodiment, the disclosure provides the capture group of formula (VIII), wherein $R_1$ is —O—NHC(O)($C_1$-$C_6$ alkoxy) and $R_2$ is hydrogen. In one embodiment, $R_1$ is —O—NHC(O)(OtBu) and $R_2$ is hydrogen.

In another embodiment, the disclosure provides the capture group of formula (VIII), wherein $R_1$ is —NHC(O)($C_1$-$C_6$ haloalkyl) and $R_2$ is hydrogen. In one embodiment, $R_1$ is —NHC(O)$CH_2$X, wherein X is halogen; and $R_2$ is hydrogen. In another embodiment, $R_1$ is —NHC(O)$CH_2$Cl or —NHC(O)$CH_2$I, and $R_2$ is hydrogen.

In another embodiment, the disclosure provides the capture group of formula (VIII), wherein $R_1$ is —NHC(O)($C_1$-$C_6$ haloalkyl) and $R_2$ is —$C_1$-$C_6$ alkylene-NHC(O)($C_1$-$C_6$ haloalkyl). In one embodiment, $R_1$ is —NHC(O)$CH_2$X, wherein X is halogen; and $R_2$ is —$C_1$-$C_6$ alkylene-NHC(O) $CH_2$X. In another embodiment, $R_1$ is —NHC(O)$CH_2$Cl or —NHC(O)$CH_2$I, and $R_2$ is —$C_2H_4$—NHC(O)$CH_2$I, —$C_2H_4$—NHC(O)$CH_2$Cl, —$C_3H_6$—NHC(O)$CH_2$I, —$C_3H_6$—NHC(O)$CH_2$Cl, —$C_4H_8$—NHC(O)$CH_2$I, or —$C_4H_8$—NHC(O)$CH_2$Cl.

In one embodiment, the disclosure provides the capture group of formula (VIII), wherein $R_1$ and $R_2$, together with a carbon atom to which they are attached, form aryl or heteroaryl ring, each substituted with $C_1$-$C_6$ alkyl, wherein such alkyl is optionally substituted with halogen, $N_3$, —NHC(O)($C_1$-$C_6$ alkyl), —$NR_3$C(O)($C_1$-$C_6$ haloalkyl), —NHC(O)($C_1$-$C_6$ alkoxy), —$NR_3$C(O)($C_1$-$C_6$ halo alkoxy), —$S(O)_{0-2}$NH($C_1$-$C_6$ alkyl), —$S(O)_{0-2}$NH($C_1$-$C_6$ haloalkyl), —$S(O)_{0-2}$($C_1$-$C_6$ alkyl), —$S(O)_{0-2}$($C_1$-$C_6$ haloalkyl), —$S(O)_{0-2}$($C_1$-$C_6$ alkoxy), —$S(O)_{0-2}$($C_1$-$C_6$ haloalkoxy), —$S(O)_{0-2}$(aryl), or —$S(O)_{0-2}$(arylalkyl).

In another embodiment, the disclosure provides the capture group of formula (VIII), wherein $R_1$ and $R_2$, together with a carbon atom to which they are attached, form aryl or heteroaryl ring, each substituted with $C_1$-$C_6$ alkyl, wherein such alkyl is optionally substituted with halogen, $N_3$, —NHC(O)($C_1$-$C_6$ haloalkyl), or —O—NHC(O)($C_1$-$C_6$ alkoxy).

In yet another embodiment, the disclosure provides the capture group of formula (VIII), wherein $R_1$ and $R_2$, together with a carbon atom to which they are attached, form aryl ring, each substituted with $C_1$-$C_6$ alkyl, wherein such alkyl is optionally substituted with halogen, $N_3$, —NHC(O)($C_1$-$C_6$ haloalkyl), or —O—NHC(O)($C_1$-$C_6$ alkoxy).

In one embodiment, the disclosure provides the capture group of formula (VIII), wherein $R_1$ and $R_2$, together with a carbon atom to which they are attached, form phenyl ring substituted with $C_1$-$C_6$ alkyl, wherein such alkyl is optionally substituted with halogen, $N_3$, —NHC(O)($C_1$-$C_6$ haloalkyl), or —O—NHC(O)($C_1$-$C_6$ alkoxy). In one embodiment, the phenyl is substituted with methyl, wherein such methyl is optionally substituted with halogen, $N_3$, —NHC(O)($C_1$-$C_6$ haloalkyl), or —O—NHC(O)($C_1$-$C_6$ alkoxy).

In one embodiment, the disclosure provides the capture group of formula (VIII), wherein $R_1$ and $R_2$, together with a carbon atom to which they are attached, form phenyl ring substituted with $C_1$-$C_6$ haloalkyl. In another embodiment, $R_1$ and $R_2$, together with a carbon atom to which they are attached, form phenyl substituted with —$CH_2$X, wherein X is halogen. In another embodiment, $R_1$ and $R_2$, together with a carbon atom to which they are attached, form phenyl substituted with —$CH_2$I or —$CH_2$Cl.

In another embodiment, the disclosure provides the capture system as described above with any reference to formula (I), wherein the capture group is:

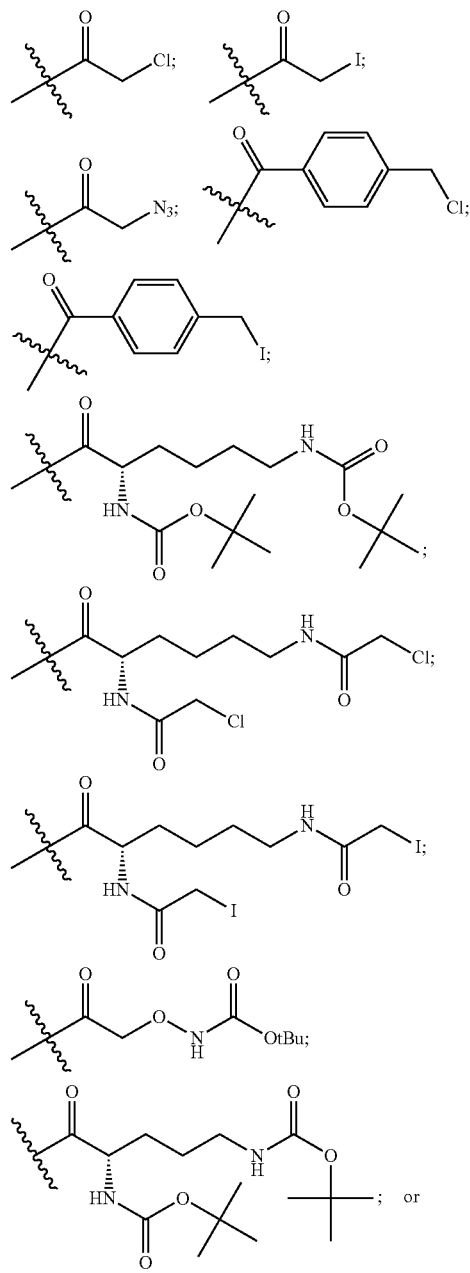

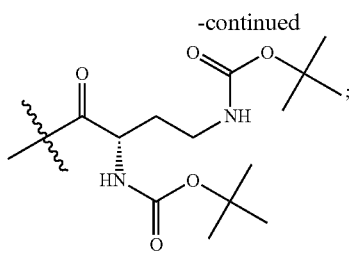

In another embodiment, the disclosure provides the capture system as described above with any reference to formula (I)

wherein n is 2-10, and wherein R' is described above with any reference to formula (I). In another embodiment, n is 2-6. In yet another embodiment, n is 4.

Methods of Isolating Proteins

In one embodiment, the method is used for purifying proteins (Scheme 1). In this embodiment, the method comprises the steps of: 1) contacting biological fluid comprising a protein of interest with a capture system to obtain the captured protein (e.g., resin coupled cross-linked protein conjugate); 2) contacting the captured proteins with acid or base to cleave from the resin, and optionally 3) analyzing the obtained cleaved cross-linked proteins using standard techniques.

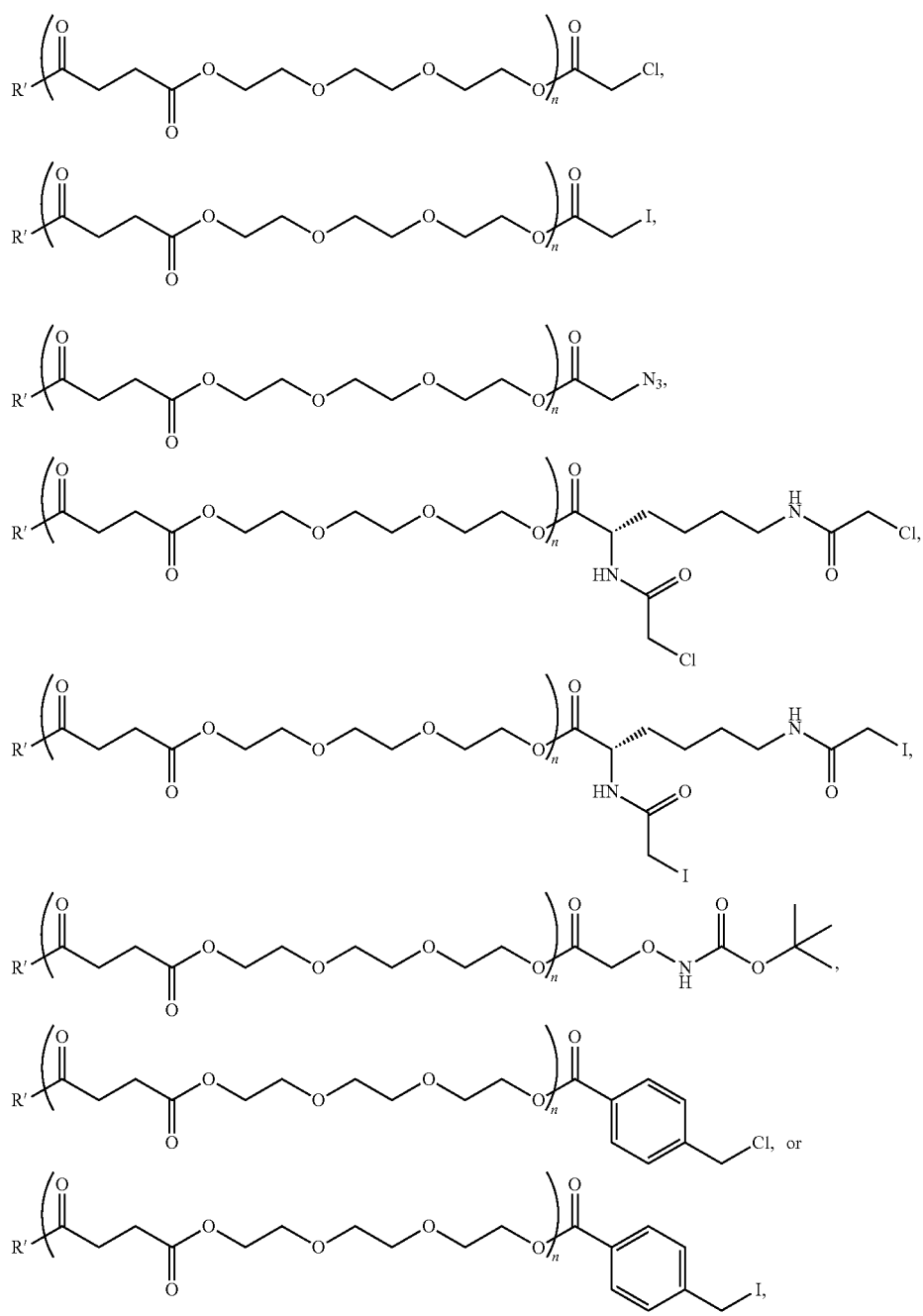

Scheme 1

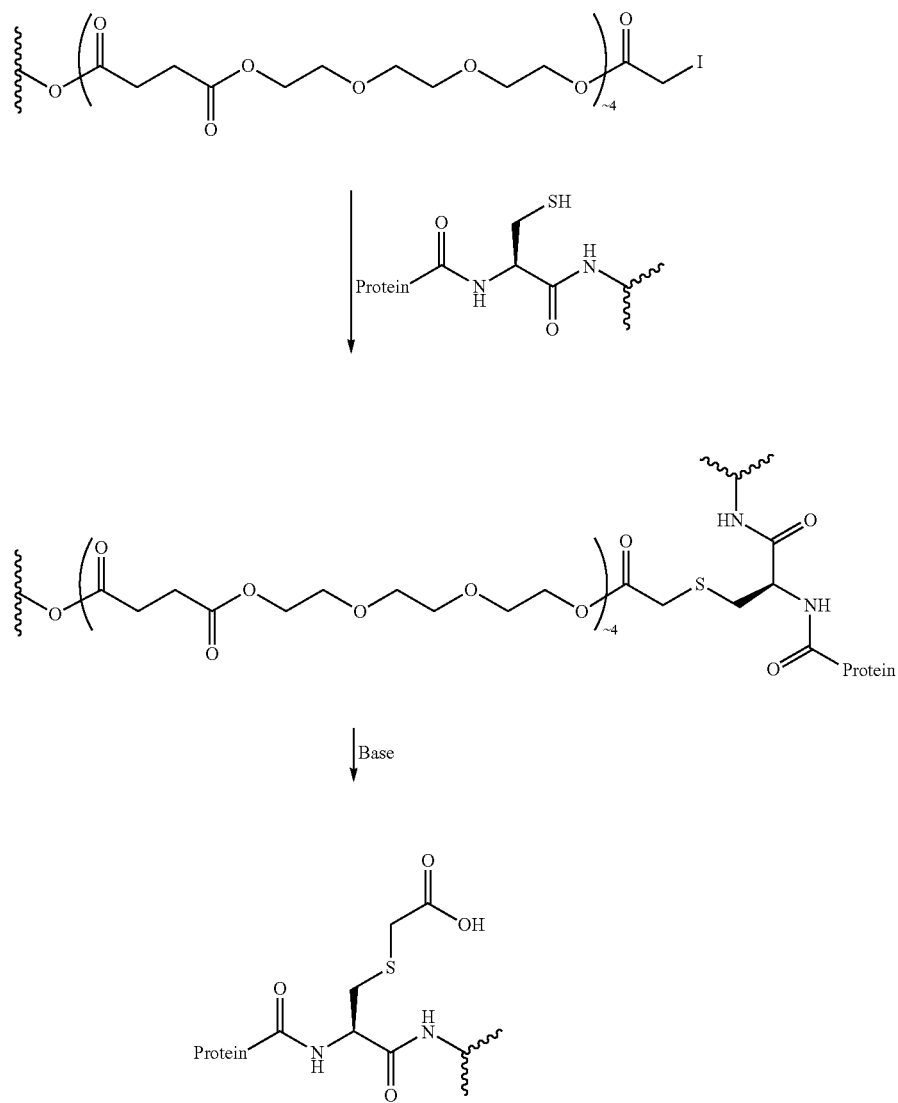

Figure 2:
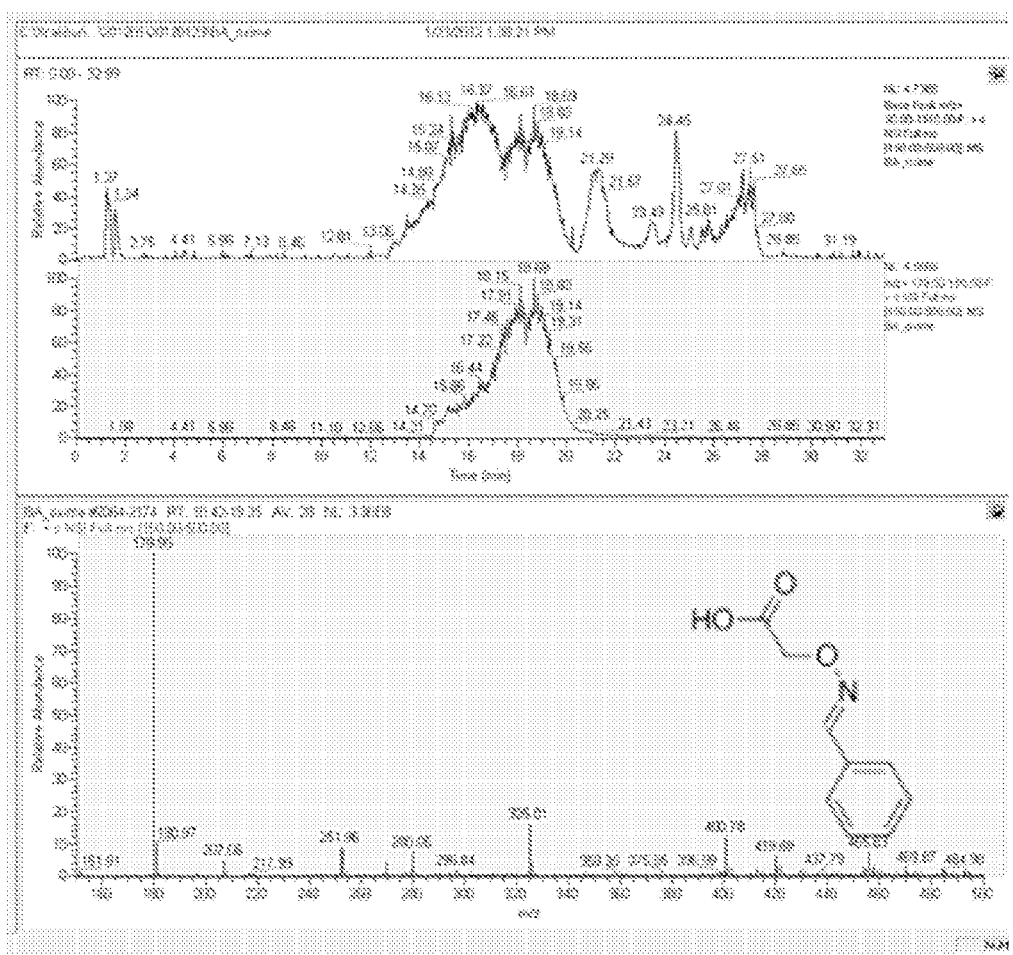
FIG. 2 shows LCMS spectra of the benzaldehyde capture with Aminooxyacetic acid-containing capture system.

Plasma (5 μL) is added to resin (5 μL) followed by 10 μL of alkylation buffer (100 mM $Na_xH_yPO_4$ pH 8.0, 300 mM NaCl, 10% glycerol v:v, 10% sorbitol w:v). The reaction mixture is mixed thoroughly, and allowed contact to continue for 30 min at room temperature. Solution phase is removed from the contacted resin and 5 μL fresh resin is added to the solution and ascorbic acid (5 mM.) The incubation procedure is repeated. The solution is removed and 5 μM of fresh resin is added followed by triscarboxyethyl phosphine (TCEP, 1 mM.) The incubation procedure is repeated. The solution is removed and 5 μM of fresh resin is added followed by 0.01% sodium dodecyl sulfate (SDS). The incubation procedure is repeated. The solution is removed and 5 μM of fresh resin is added followed by 0.1% sodium dodecyl sulfate. The incubation procedure is repeated and the solution is removed. Resin is washed and contacted under the different conditions each with 200 μL 0.01% SDS and 200 μL water. The results of the protein purification are illustrated in FIG. 2.

In one embodiment, the method is used for generating and isolating distance accurate chemical cross-links from purified proteins (Scheme 2). In this embodiment, the method comprises the steps of: 1) contacting biological fluid comprising a protein of interest with a compound of formula (II) to obtain cross-linked proteins; 2) activating the capture system of formula (I-A) by treatment with a reducing agent to obtain activated capture system; 3) contacting the cross-linked protein with the activated capture system to obtain the captured protein (e.g., resin coupled cross-linked protein conjugate); 4) contacting the captured proteins with acid or base to cleave from the resin, and optionally 5) analyzing the obtained cleaved cross-linked proteins using standard techniques.

Scheme 2
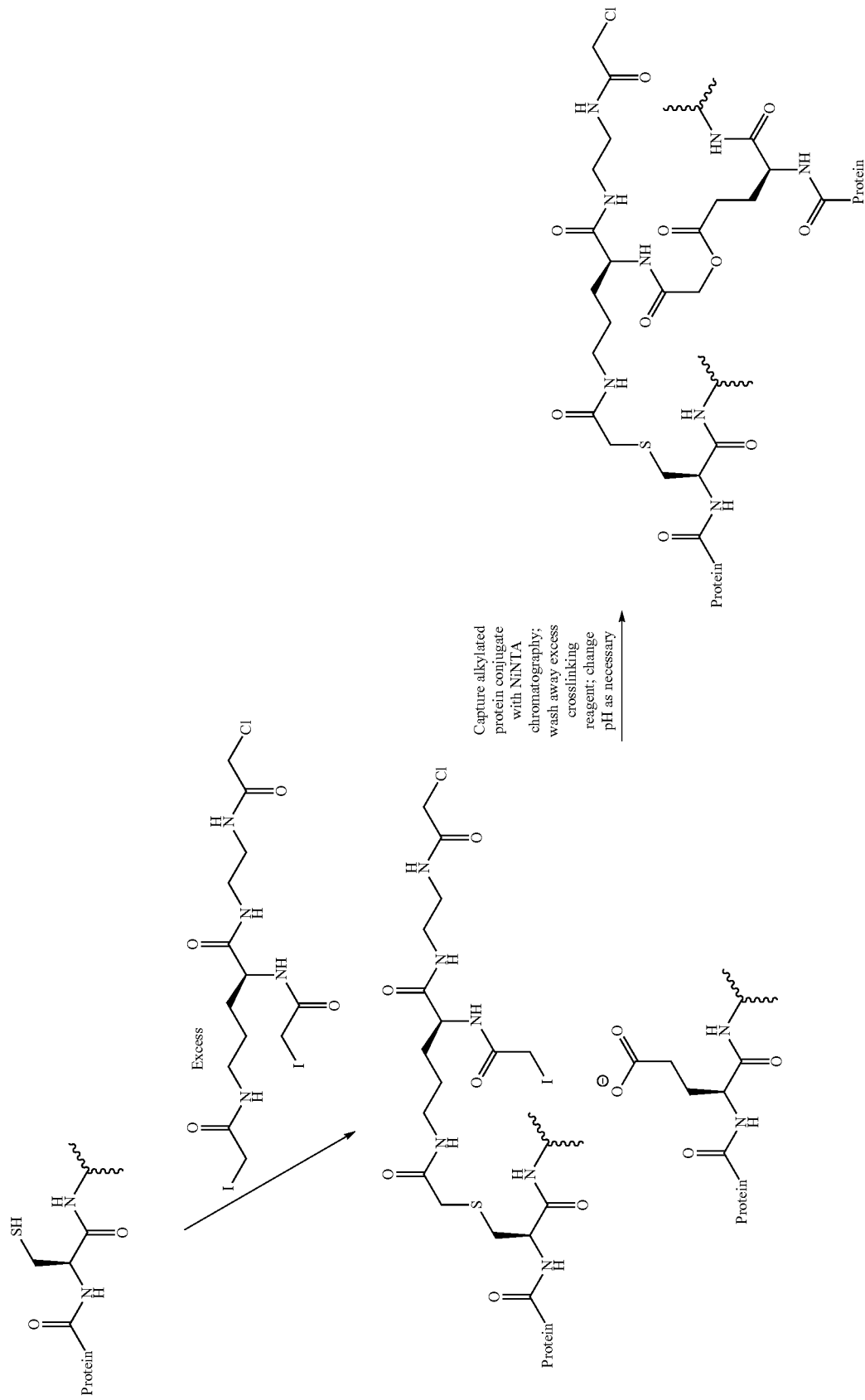

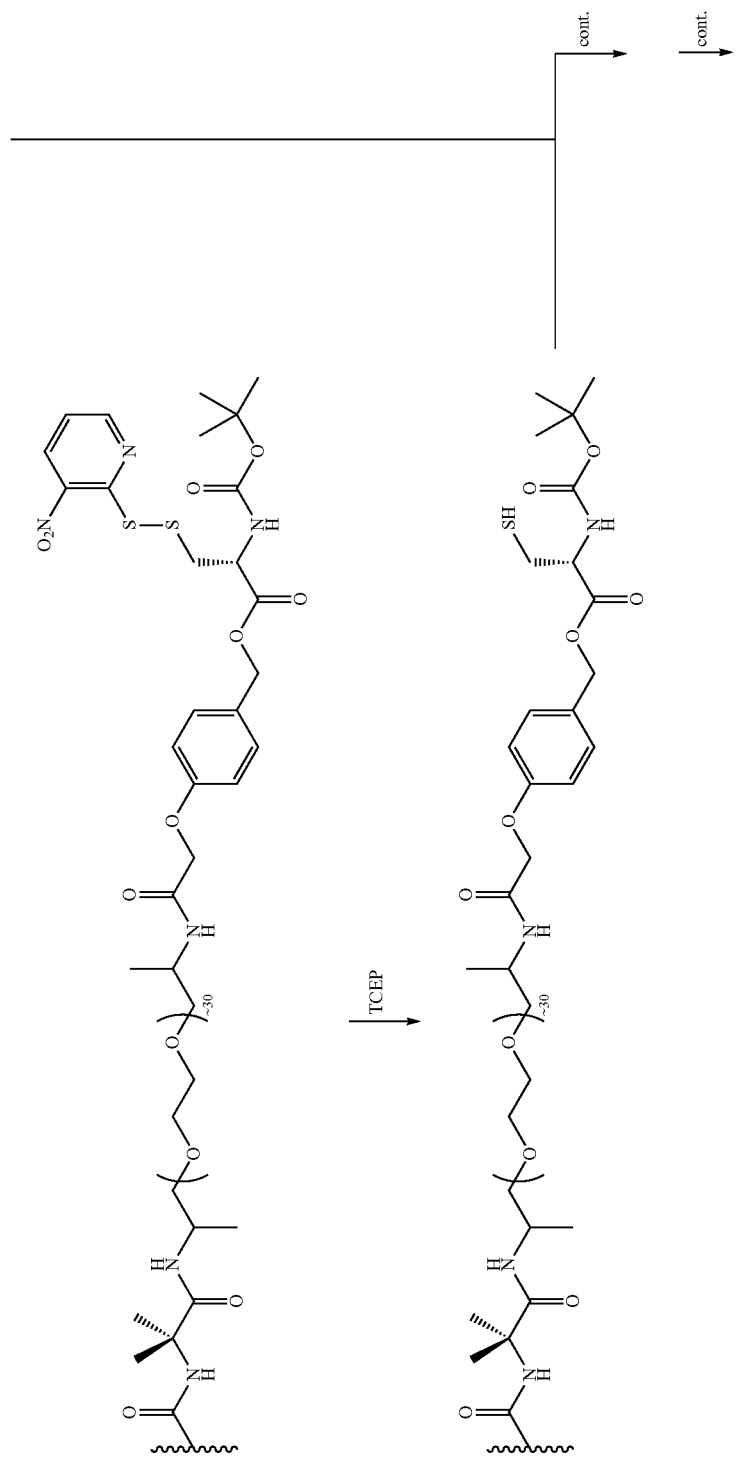

-continued
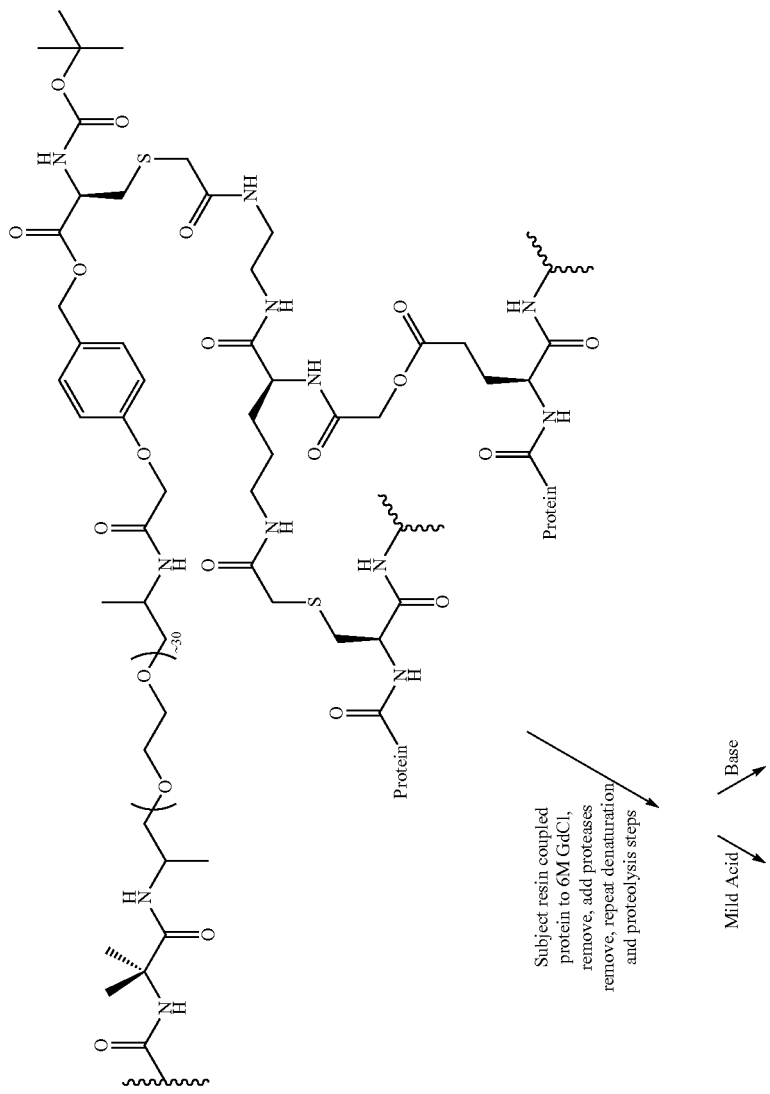

-continued
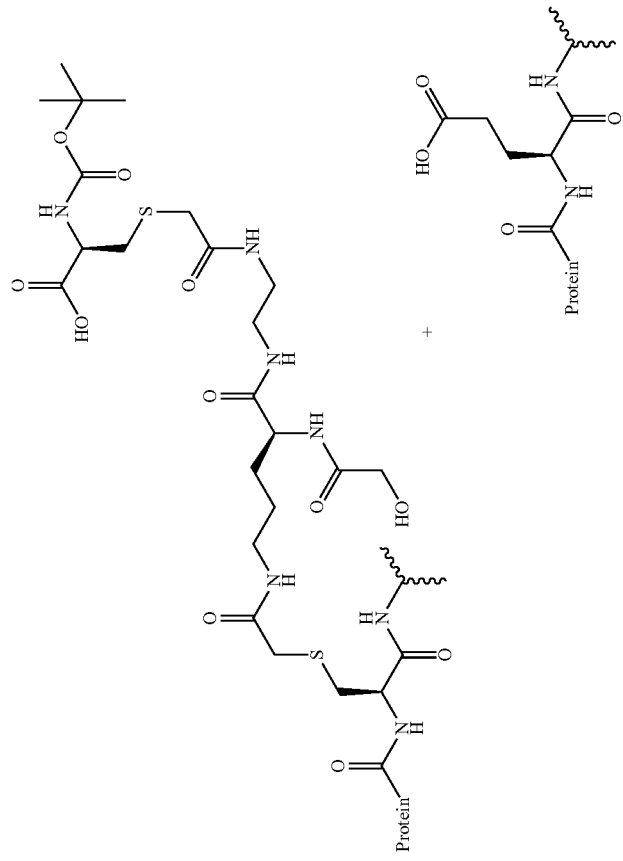
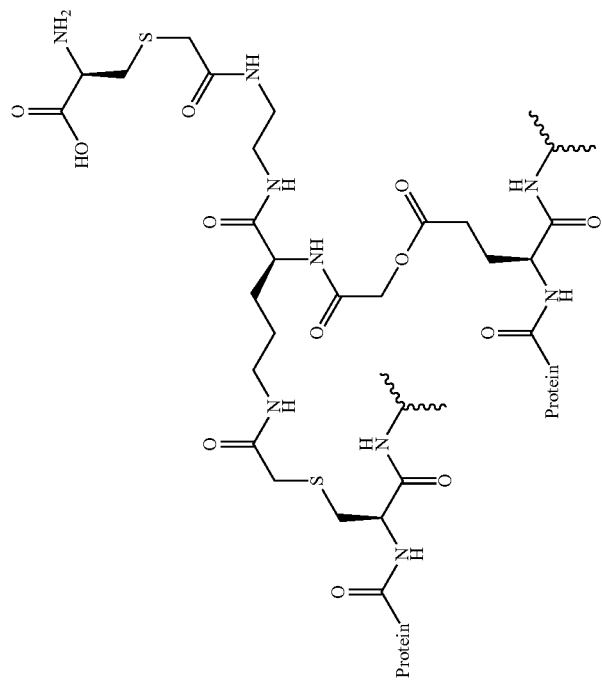

For example, proteins may be exogenously expressed with either an N- or C-terminal polyhistidine tag in any of the standard organisms (e.g., *E. coli*, Chinese Hamster Ovary Cells, insect cells, etc.) If the proteins are secreted by the organism the protein is isolated from the extracellular media by Ni-NTA chromatography (available from QIAGEN GmbH, Hilden, Germany). If the proteins are expressed intracellularly the cells are lysed by detergent and the protein is isolated by Ni-NTA chromatography. Isolation of proteins will be obvious to those of skill in the art.

The protein may be contacted with a compound of formula (II) in vast molar excess (1-25 mM; usually 10 mM) while on the Ni-NTA resin, prior to elution at room temperature for 30 minutes. The unreacted compound of formula (II) is washed away and the cross-linked protein is eluted from Ni-NTA column and immediately desalted (by any of the standard methods).

Incubation to form crosslinks may be performed at 4° C., room temperature, or 37° C. as the protein stability allows, and for times ranging from 30 minutes to multiple days as the protein stability allows. Crosslinks with acidic residues may be enhanced by allowing these reactions to proceed in phosphate buffered media at neutral or slightly acidic pH. Crosslinks with alcohol presenting residues may be enhanced by allowing these reactions to proceed in the presence of cesium and other reagents known to those skilled in the art.

The capture system can be activated by washing 10 µL of resin slurry (estimated 15 nmols of protected thiol) with 50 µL of triscarboxyethyl phosphine (TCEP, 50 mM). This bright yellow liquid is saved to confirm the concentration of deprotected thiol by UV-Vis spectroscopy. The TCEP is washed away with two 800 µL washes of water.

Desalted, eluted cross-linked proteins may be captured by contacting with the activated resin in 50 mM NaHCO$_3$ for 4 hours at room temperature, with or without 1-1000 mM NaI.

Cross-linked proteins covalently attached to the resin may be denatured by removing the carbonate buffer and washing with 6M guanidinium chloride (GcCl). The GdCl buffer is removed and the resin coupled unfolded cross-linked protein conjugate is diluted into 200 µL of Hepes (pH 8.0, 100 mM) containing proteases and relevant stabilizers or co-catalysts (typically: 5 mM CaCl$_2$ with 100 µg/mL Trypsin and 100 µg/mL chymotrypsin). The first round of proteolysis is allowed to proceed for 30 minutes at room temperature. The proteases are washed from the resin with two 800 µL washes of Hepes (pH 8.0, 100 mM). The semi-digested resin coupled cross-linked protein conjugate may be subjected to at least one more round of GdCl induced unfolding and proteolysis as above or with another collection of proteases as needed.

The resin coupled cross-linked proteolytic peptides can be cleaved from the resin by contacting the resin with either aqueous base (typically 40 µL 50 mM tetramethylammonium hydroxide) for 2 minutes at room temperature or weak acid (typically 40 µL 95% TFA (HMPA resins) or 40 µL 1% TFA (HMPB resins)). The base cleavage reactions can be neutralized, typically with 2-2.5 µL 1M acetic acid. 95% TFA cleavages are allowed to evaporate and are diluted with water.

The 1% TFA reactions may be neutralized with 4-5 µL ammonium carbonate (1M). These neutralized peptide mixtures may be subjected to nano-LCMSn by the methods known to those skilled in the art.

In one embodiment, the method is used for isolating a specific disulfide containing peptides from serum or plasma without antibodies (Scheme 3). In one embodiment, the method comprises the steps of: 1) contacting a mixture comprising a protein of interest with a compound of formula (II) to cross-link protein; 2) activating the capture system of formula (I-A) by treatment with a reducing agent to obtain activated capture system; 3) contacting the cross-linked protein with the activated capture system to obtain the captured protein (e.g., resin coupled cross-linked protein conjugate); 4) contacting the captured proteins with acid or base to cleave from the resin, and optionally 5) analyzing the obtained cleaved cross-linked proteins using standard techniques. In another embodiment, the peptide of interest contains a free thiol group. Then, the compound of formula (II) contains two thiol reactive groups of different reactivity, one slower reacting than the other. In another embodiment, the peptide of interest contains disulfide bond. Then, the compound of formula (II) contains one or two thiol reactive groups of identical reactivity and a second or third reactive group, slower reacting than the others.

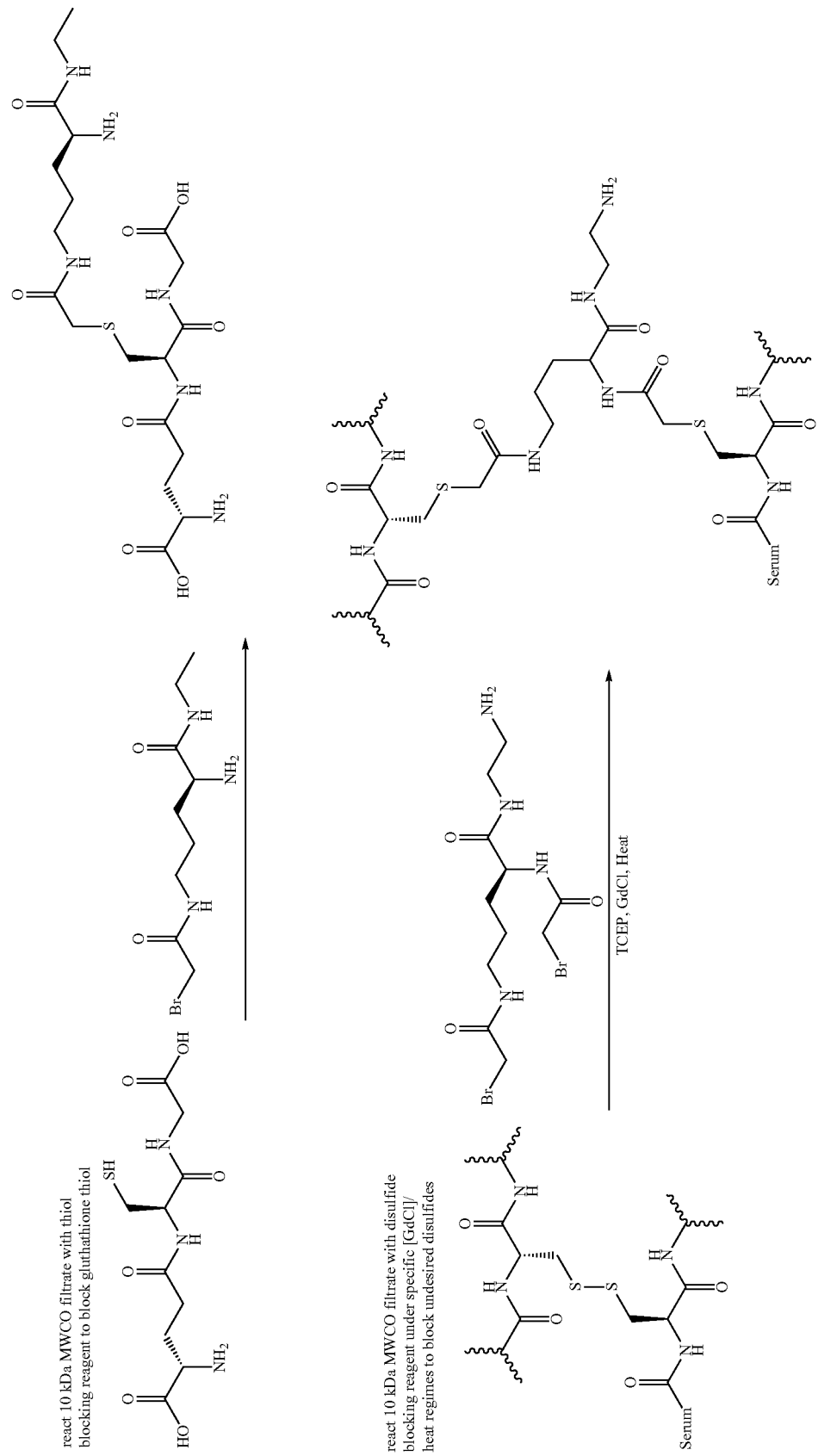

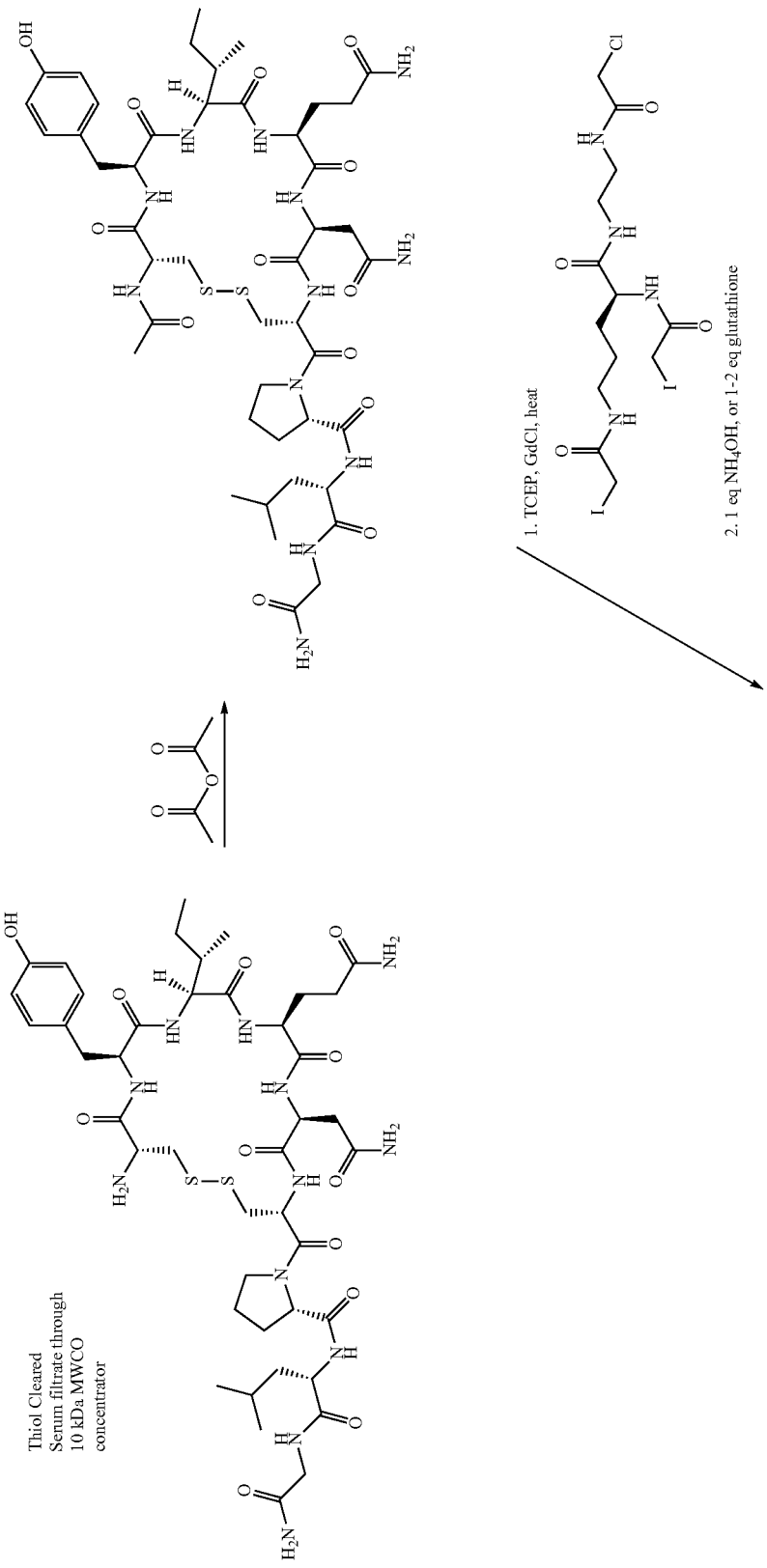

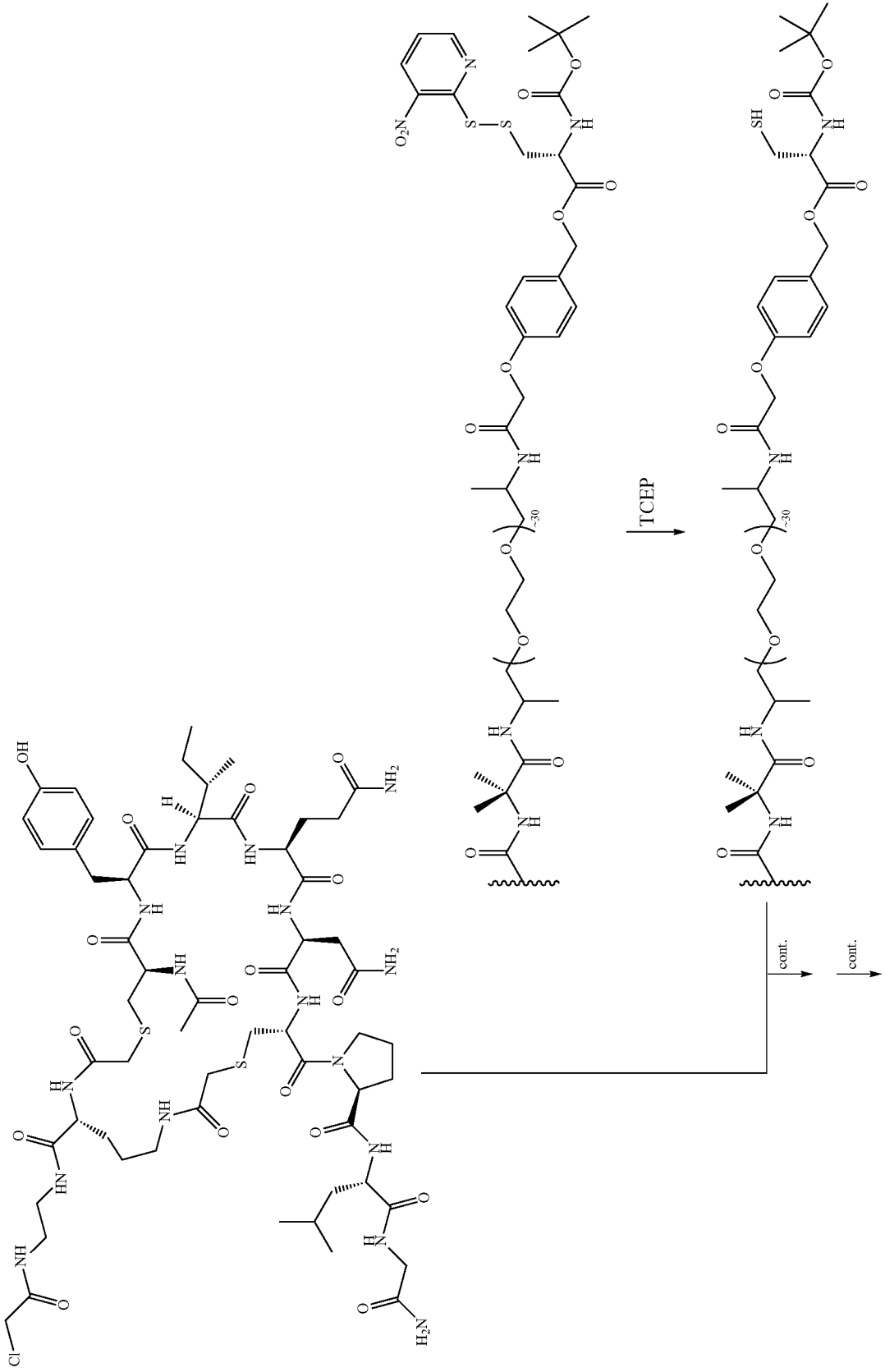

-continued
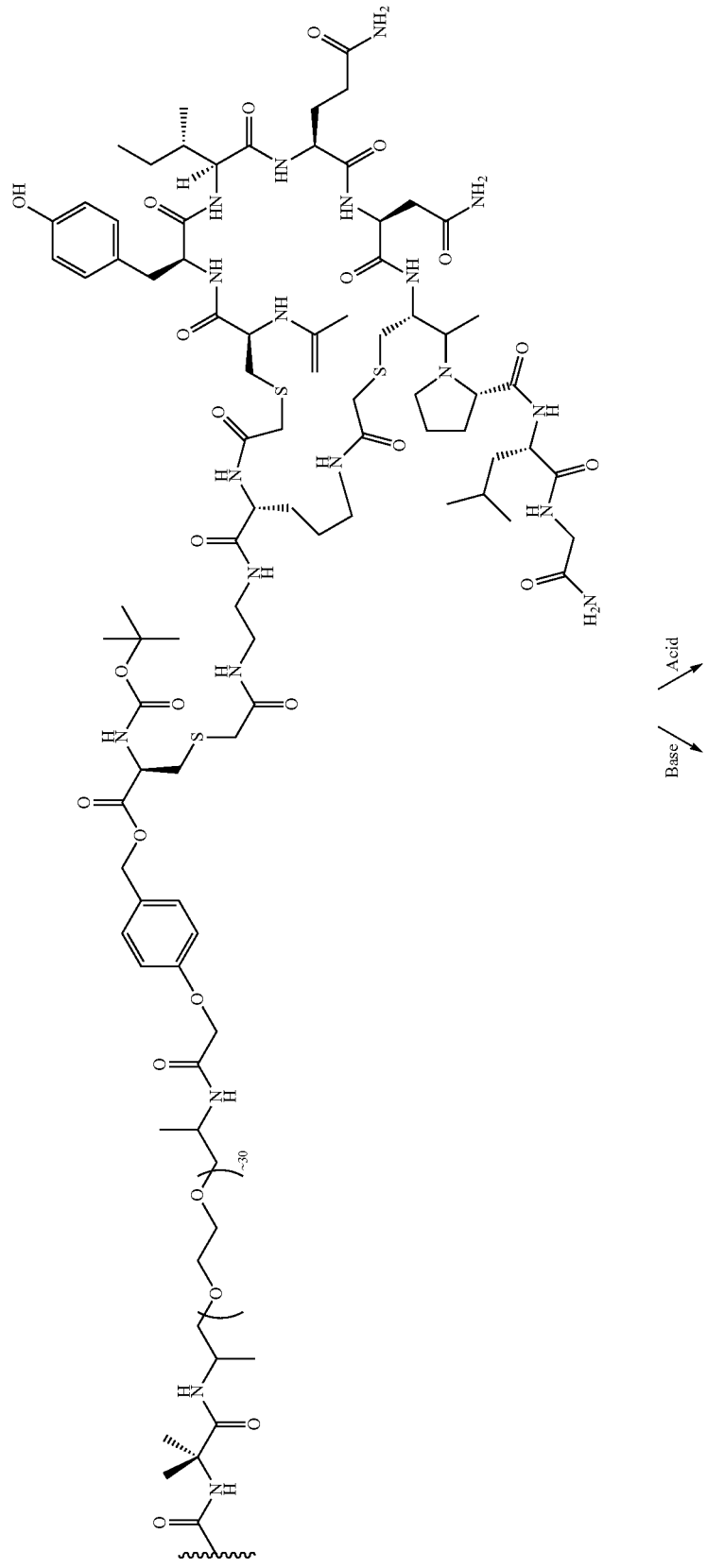

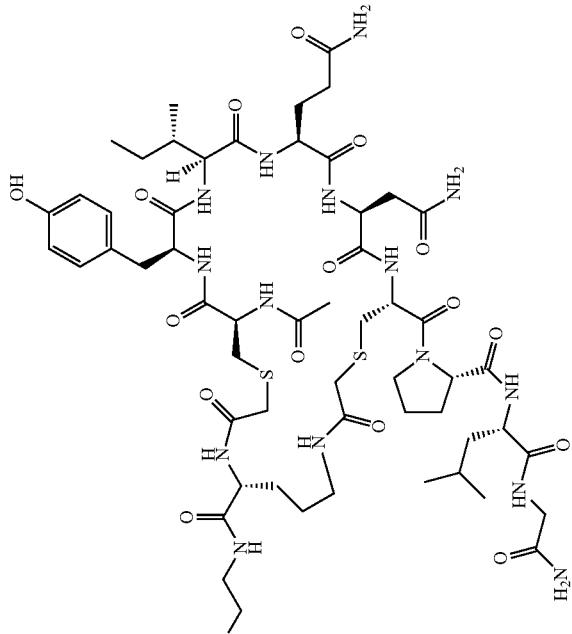
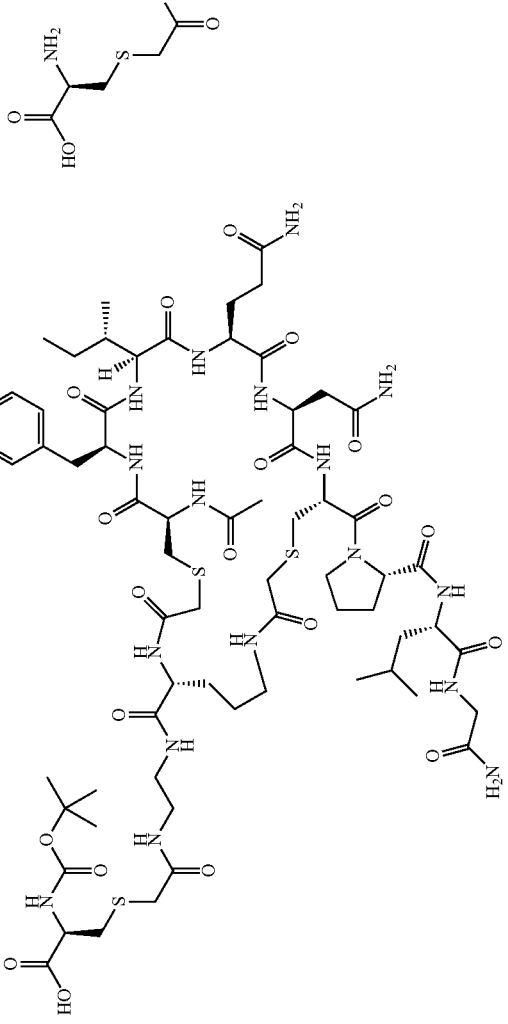

-continued
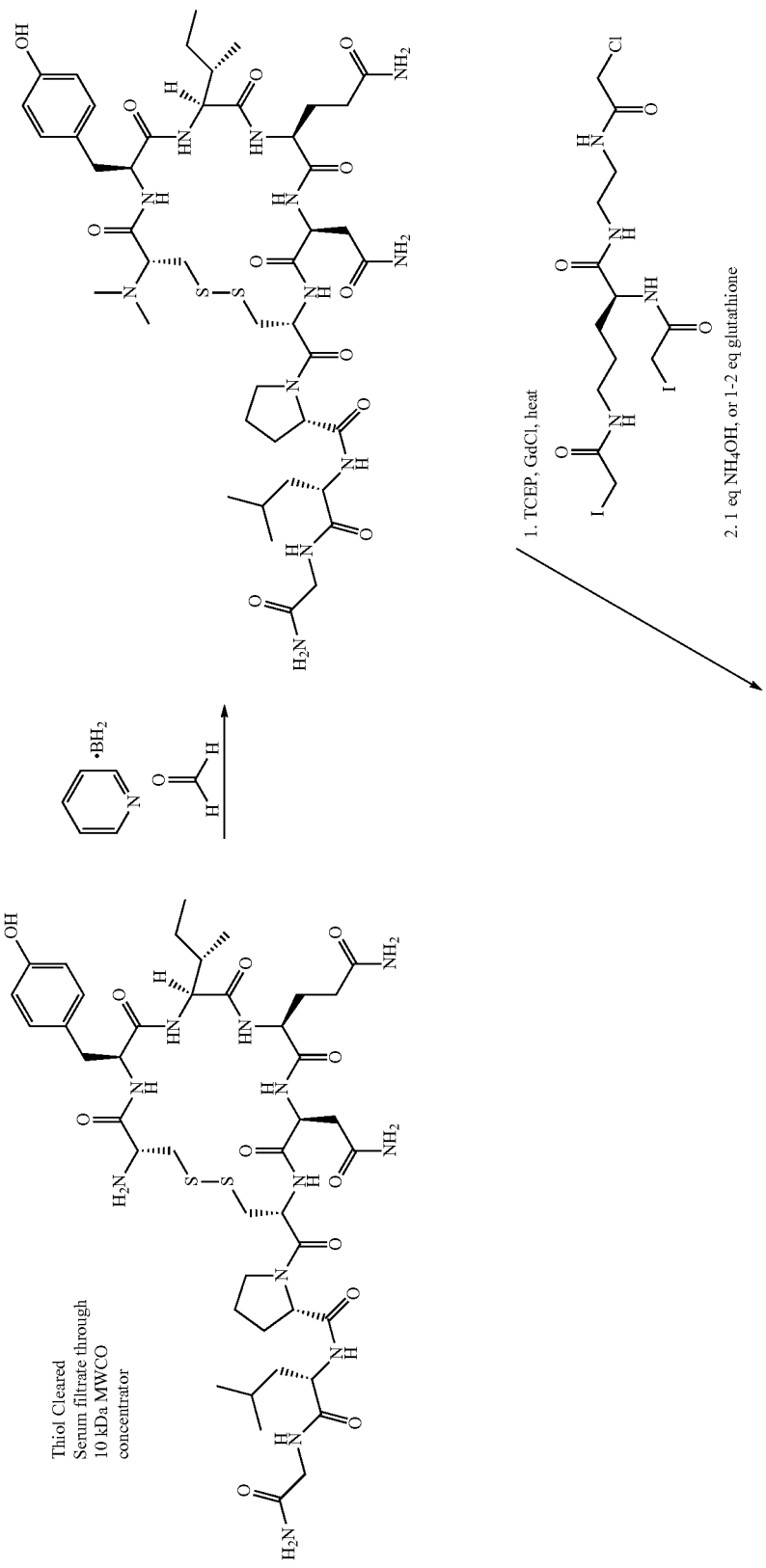

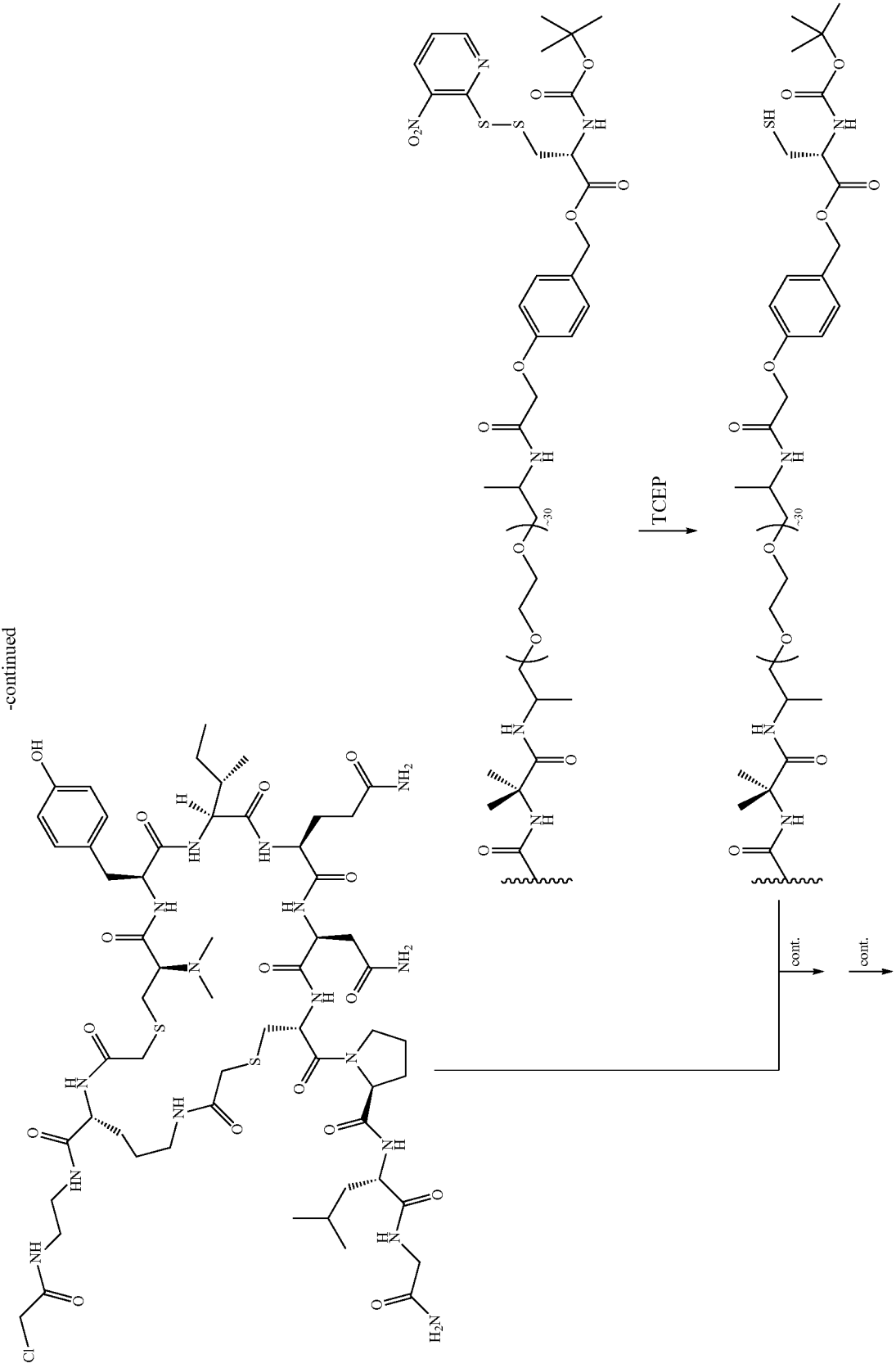

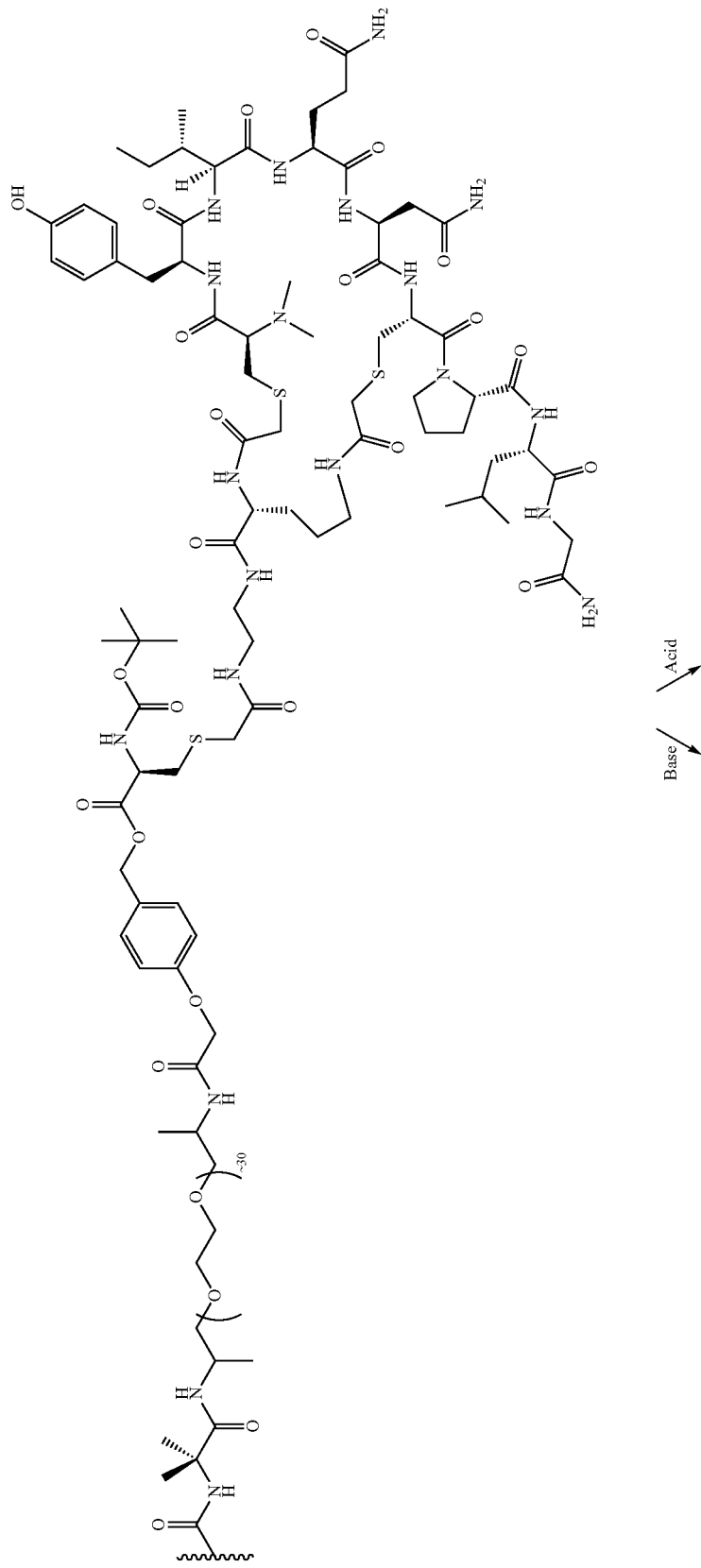

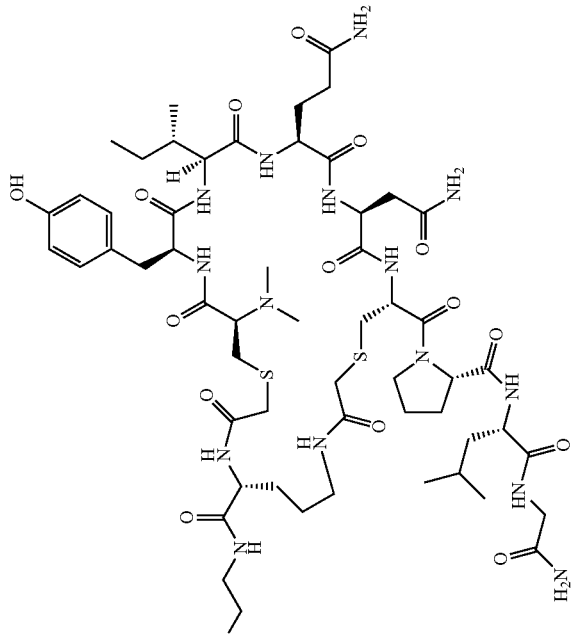
-continued
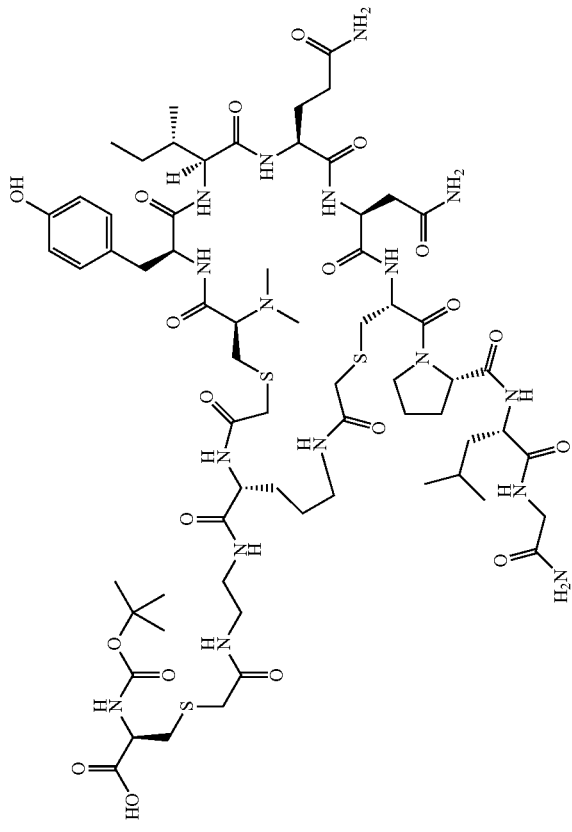

For example, serum may be fractionated by molecular weight cutoff ultrafiltration as is obvious to those skilled in the art. For example, species less than 10 kDa may be collected as flow-through from filtration of serum with a 10 kDa molecular weight cutoff filter. Specific thiol or other nucleophilic functional groups (for example, imidazole nitrogen, alpha amino, indole nitrogen) activated by their proximity to a free thiol or other specifics of their environment in the presenting peptides may be captured from the filtered media by the following procedure:

Immediately before use any of the boc-protected amine containing compounds claimed here may be deprotected. Typically, deprotection is done with 10 µL 95% TFA/mg of compound for 20 minutes at room temperature. The deprotected amines are isolated as TFA salts by trituration into 10 µL ether/TFA (95%). The salt is collected by centrifugation, and the solvent supernatant is poured off. The pellet is dissolved in water to about 100 mM, and blocking reagent and used immediately.

Undesired free thiols and amines in the serum size fractions may be blocked by contacting them with blocking alkylating reagents (e.g., compounds of formula (IV)) in vast molar excess (typically 10 mM) in 100 mM $NaHCO_3$ for 30 minutes at room temperature under relatively non-denaturing conditions. These blocking reagents do not present an additional resin-capture functional group (typically a slower reacting alpha-halo moiety) but do present an alkyl amine. The alpha-halo groups on these thiol-blocking compounds first alkylate exposed free thiols and other activated nucleophilic groups in the serum fraction. Then, the reaction is allowed to self-quench as excess the alpha-halo groups are consumed intramolecularly by the alkyl amine. This typically takes another 30 minutes to an hour.

Undesired thiols naturally protected in disulfides may be blocked by contacting them with reducing agent (typically 1 mM TCEP) and blocking alkylating agents (e.g., compounds of formula (III)) in vast molar excess (typically 10 mM) in 100 mM $NaHCO_3$ for 30 minutes at room temperature. These disulfide blocking reagents may contain one or two identical thiol-alkylating function groups and an alkyl amine but not an additional slower reacting thiol group.

The alpha-halo groups on the disulfide blocking compounds first alkylate exposed reduced thiols and activated nucleophilic groups in the serum fraction. Then the reaction can be allowed to self-quench as excess the alpha-halo groups are consumed intramolecularly by the alkyl amine. This typically takes another 30 minutes to an hour.

The serum size fraction may be then diluted into a slightly higher concentration of denaturant (typically less than about 20 mM GdCl) and contacted with new reagents depending on the desired outcome.

If isolation of a peptide containing a free thiol is desired the sample may be contacted with an alkylating agent (e.g., compounds of formula (II)) in vast molar excess (typically 10 mM) containing two thiol reactive groups of different reactivity, one slower reacting than the other. This is either done initially or subsequent to a free thiol blocking step. If it is done subsequent to a free-thiol blocking step, thiols that were previously protected from alkylation by the steric hindrance provided by the protein/peptide structure are newly exposed by an incremental increase in denaturant.

If isolation of a peptide containing a disulfide is desired the sample may be contacted with an alkylating agent (e.g., compounds of formula (II)) in vast molar excess (typically 10 mM) containing one or two thiol reactive groups of identical reactivity and a second or third reactive group, slower reacting than the others. This is either done initially or subsequent to a disulfide blocking step. If it is done subsequent to a disulfide blocking step, thiols that were previously protected from alkylation by the disulfide and the steric hindrance provided by the protein/peptide structure are newly exposed by an incremental increase in denaturant (typically about 20 mM GdCl) and additional reducing agent (typically 0.1-1.0 mM TCEP).

If isolation of a peptide containing a free thiol is desired the excess unmodified alkylating reagent (e.g., compounds of formula (II)) may be consumed by exposure to a high concentration of primary amine at high pH. This concentration depends on the alkylating agent used but is high enough to alkylate the faster thiol alkylating group but not high enough to alkylate the slower thiol alkylating group intermolecularly. The secondary amine that forms from the alkylation of the faster thiol reacting group with the primary amine will react with the intramolecular slower thiol alkylating group under these conditions as well. The reaction is intramolecular and alkylation of secondary amines is faster than primary amines. The existing peptide alkylating reagent conjugates in the mixture will remain unmodified, retaining their resin alkylating group because they lack the faster thiol reacting group that is alkylated with the primary amine under these conditions. (Typical conditions for the amine alkylation are 1 M propyl amine (pH 10-14), or 1 M hydroxyl amine (pH 8-12). Amine alkylation reactions are quenched by lowering the pH).

If isolation of a peptide containing a disulfide is desired the excess unmodified alkylating reagent may be consumed by exposure to a high concentration of ammonium hydroxide. This concentration depends on the alkylating agent used but is high enough to alkylate the faster thiol alkylating groups but not high enough to alkylate the slower thiol alkylating group intermolecularly. The primary amine that forms from the reaction of the ammonia with one of the fast thiol reactive groups on the excess alkylating reagents will be quickly alkylated intramolecularly by the other fast reacting thiol reactive group. The secondary amine that forms from the alkylation of both faster thiol reacting groups sequentially with the ammonia will react with the intramolecular slower thiol alkylating group under these conditions as well. The reaction is intramolecular and alkylation of secondary amines is faster than primary amines. The existing peptide alkylating reagent conjugates in the mixture will remain unmodified, retaining their resin alkylating group because they lack the faster thiol reacting group that is alkylated with the ammonia under these conditions. (Typical conditions for the amine alkylation are 1M-8M ammonium hydroxide pH 10-14. Amine alkylation reactions are quenched by lowering the pH).

The capture system may be activated by washing 10 µL of resin slurry, (estimated 15 nmols of protected thiol) with 50 µL triscarboxyethyl phosphine (TCEP, 50 mM). This bright yellow liquid is saved to confirm the concentration of deprotected thiol by UV-Vis spectroscopy. The TCEP is washed away with two 800 µL washes of water.

Both free thiol alkylated and the reduced disulfide alkylated proteins and peptides may be captured by contacting the cleared reaction mixture with the activated capture resin for 4 hrs at room temperature in 50 mM $NaHCO_3$ buffered water with or without 1-1000 mM NaI.

Both free thiol alkylated and the reduced disulfide alkylated proteins and peptides covalently attached to the resin may be proteolyzed or eluted intact. If they are proteolyzed they are denatured by removing the carbonate buffer and washing with 6M guanidinium chloride (GcCl). The GdCl buffer is removed and the resin coupled unfolded protein or peptide conjugate is diluted into 200 μL Hepes (100 mM, pH 8.0) containing proteases and relevant stabilizers or co-catalysts (typically: 5 mM CaCl₂, with 100 ng/mL Trypsin and 100 ng/mL chymotrypsin). The first round of proteolysis is allowed to proceed for 30 minutes at room temperature. The proteases are washed from the resin with two 800 μL washes of Hepes (100 mM, pH 8.0). The semi-digested resin coupled protein or peptide conjugate may be subjected to at least one more round of GdCl induced unfolding and proteolysis as above or with another collection of proteases as needed.

Both free thiol alkylated and the reduced disulfide alkylated proteins and peptides covalently attached to the resin that were proteolyzed or left intact may be cleaved from the resin by contacting the resin with either aqueous base (typically 40 μL 50 mM tetramethylammonium hydroxide) for 2 minutes at room temperature or weak acid (typically 40 μL 95% TFA (HMPA resins) or 40 μL 1% TFA (HMPB resins)). The base cleavage reactions are neutralized, typically with 2-2.5 uL 1M acetic acid. 95% TFA cleavages are allowed to evaporate and are diluted with water. The 1% TFA reactions are neutralized with 4-5 μL ammonium carbonate (1M). These neutralized peptide mixtures are subjected to nano-LCMSn by the methods obvious to those skilled in the art.

In one embodiment, the method is used for removing serum albumin from serum (Scheme 4). In this embodiment, the method comprises the steps of: 1) contacting serum comprising serum albumin with a compound of formula (III) to cross-link serum albumin; 2) activating the capture system of formula (I-A) by treatment with a reducing agent to obtain activated capture system; 3) contacting the cross-linked serum albumin with the activated capture system to obtain the captured serum albumin (e.g., resin coupled cross-linked serum albumin conjugate); 4) contacting the captured serum albumin with acid or base to cleave from the resin, and optionally 5) analyzing the obtained cleaved cross-linked proteins using standard techniques.

Scheme 4

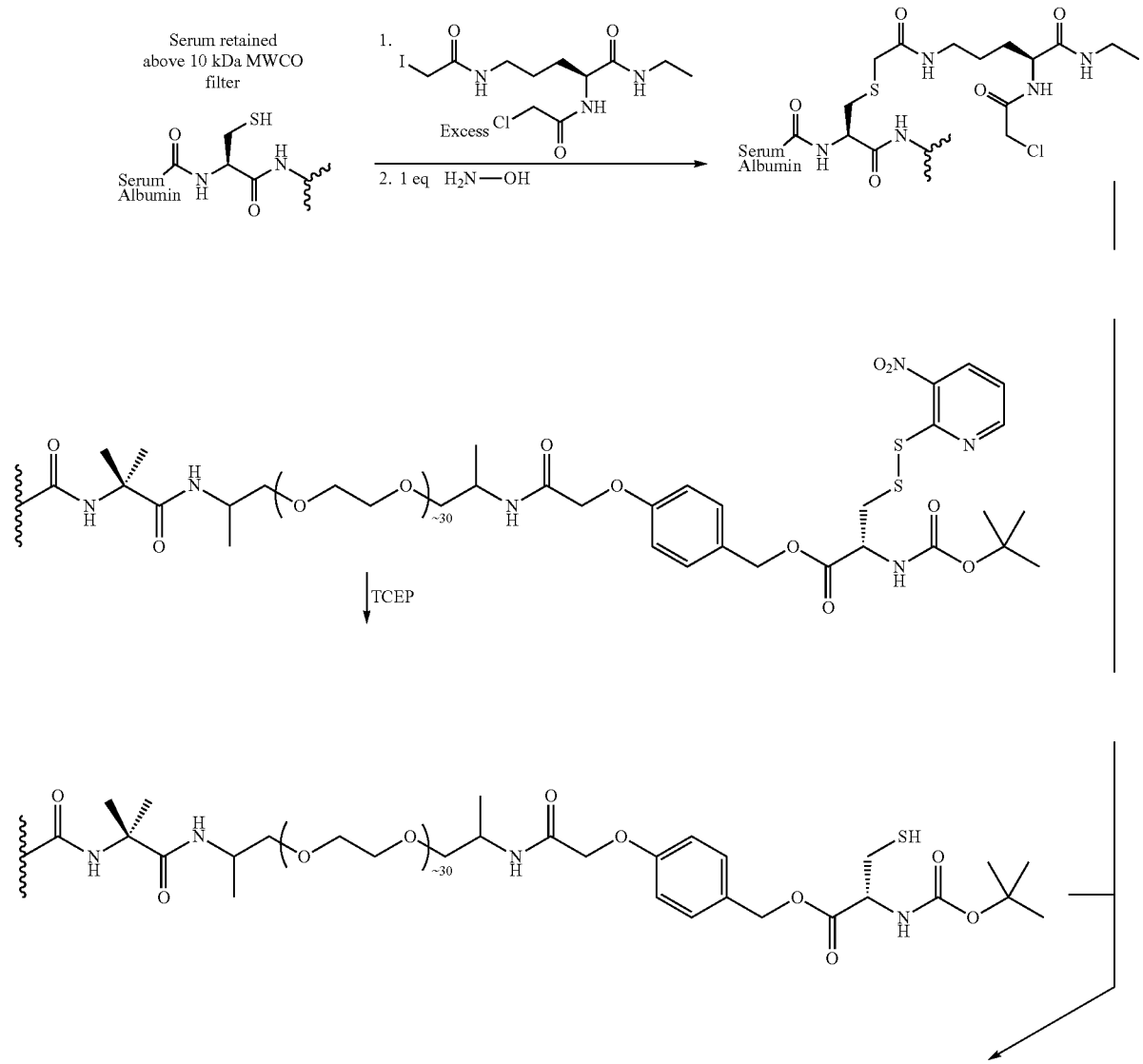

-continued

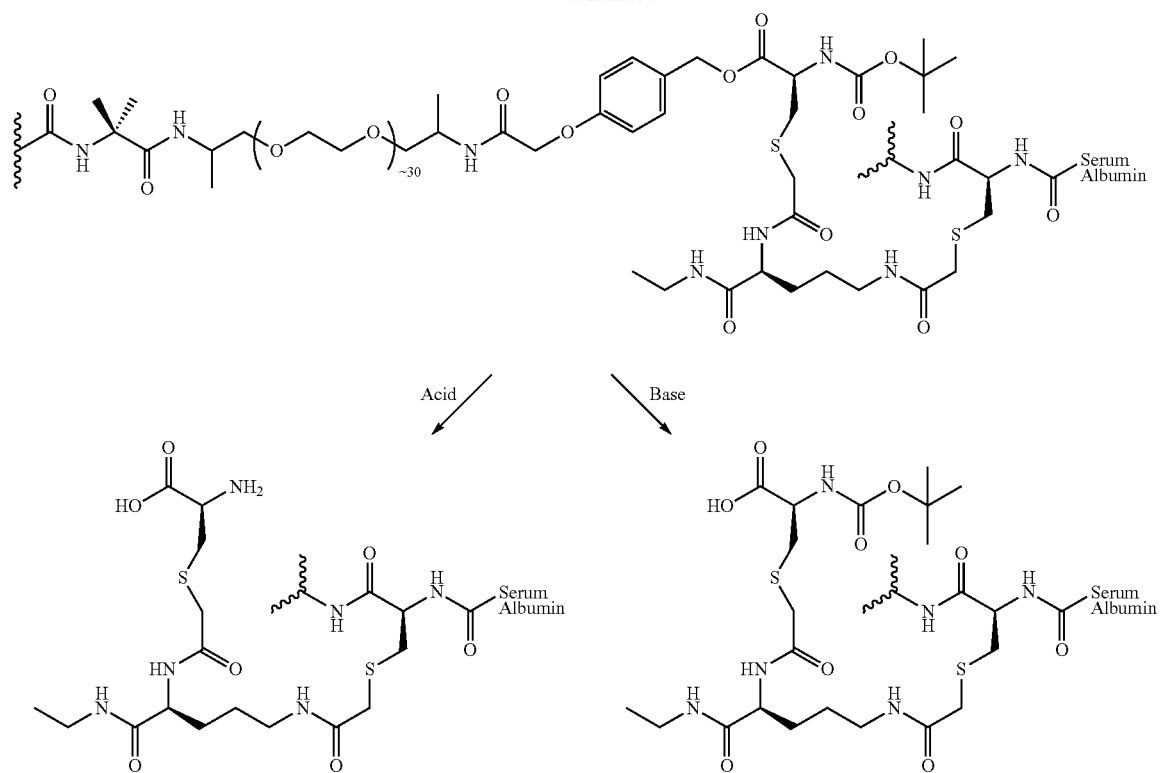

In one embodiment, the method is used for quantifying thiols in peptides obtained in different protein expression experiments (Scheme 5). In one embodiment, the method comprises the steps of: 1) contacting protein mixture comprising a protein of interest with a compound of formula (III) to cross-link protein; 2) activating the capture system of formula (I-A) by treatment with a reducing agent to obtain activated capture system; 3) contacting the cross-linked protein with the activated capture system to obtain the captured protein (e.g., resin coupled cross-linked protein conjugate); 4) contacting the captured serum albumin with acid or base to cleave from the resin, and optionally 5) analyzing the obtained cleaved cross-linked proteins using standard techniques. In another embodiment, the compound of formula (III) has $R_3$ group that is isotopically labeled.

Scheme 5

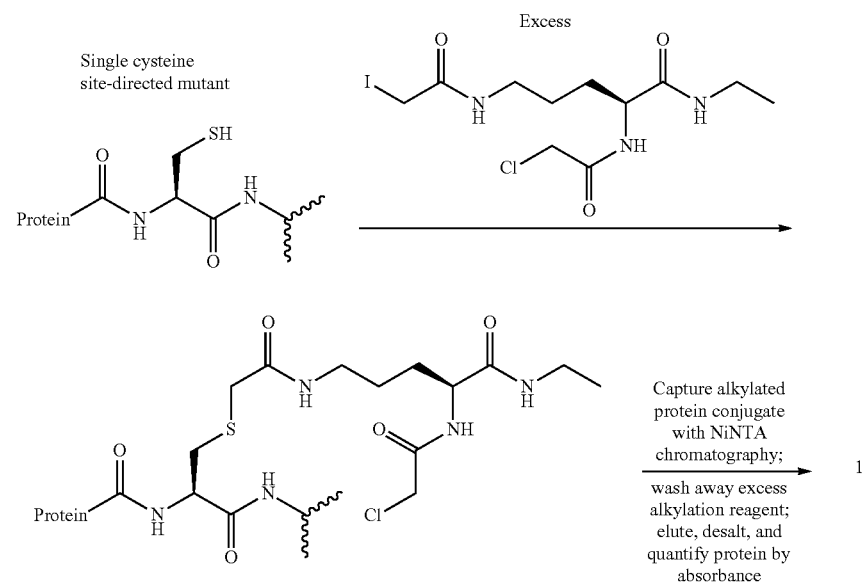

-continued
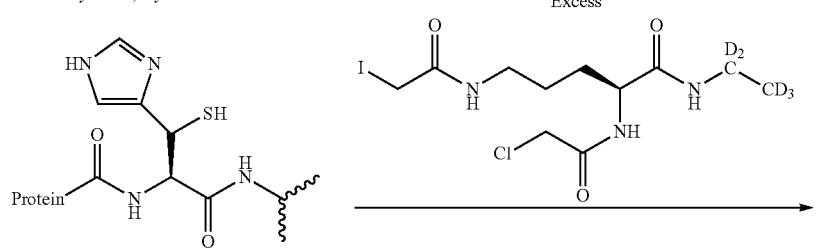
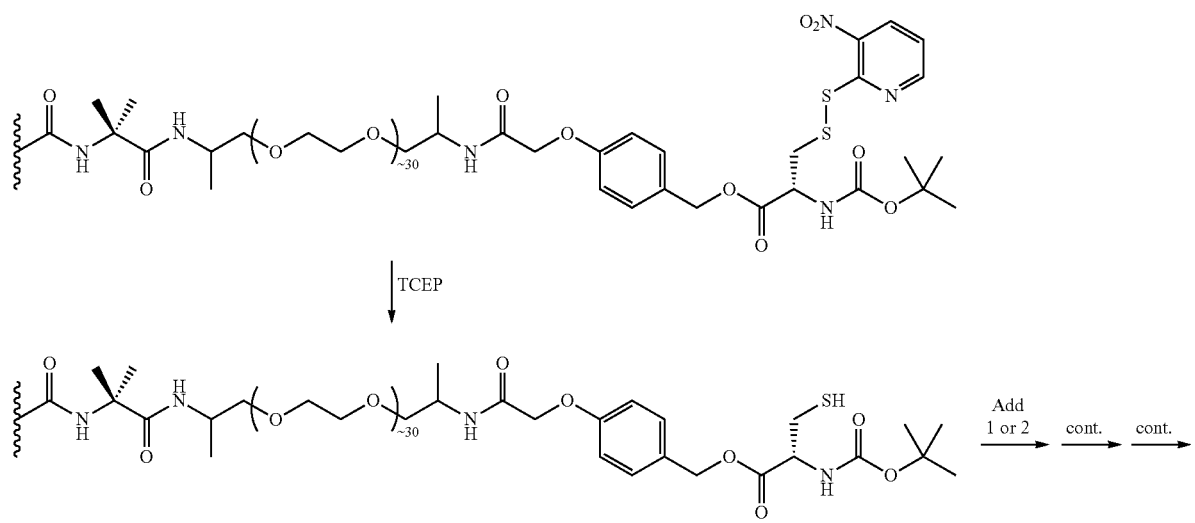
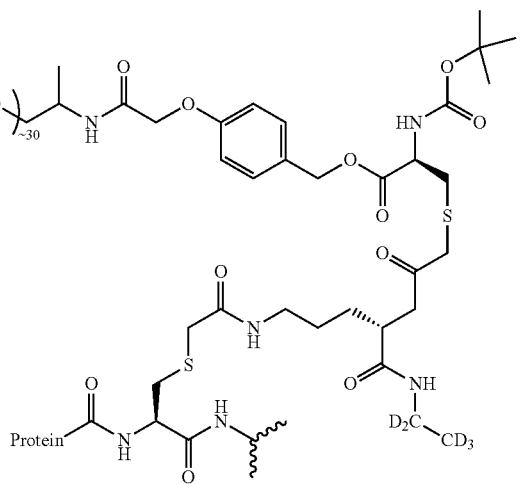

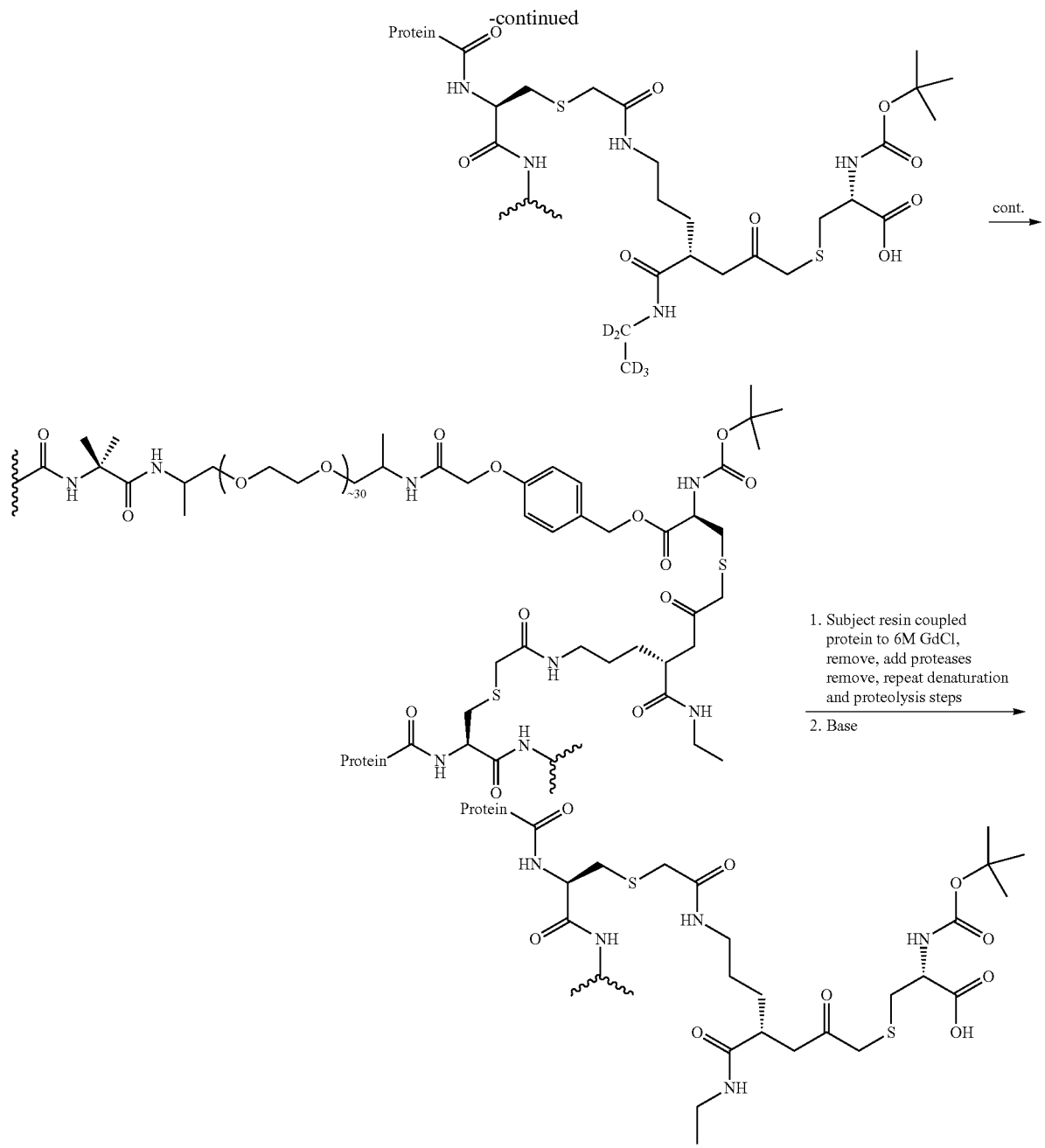

Definitions

The following terms and expressions used herein have the indicated meanings.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, means —NH$_2$. The term (C$_1$-C$_6$ alkyl)amino as used herein means —NH(C$_1$-C$_6$ alkyl), and di(C$_1$-C$_6$ alkyl)amino means —N(C$_1$-C$_6$ alkyl)$_2$.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3 (4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (I-A) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means —OH.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

The term "protein" or "protein moiety" as used herein, means a plurality of amino acid residues (generally greater than 10) joined together by peptide bonds, and has a molecular weight greater than 0.5 kDa, preferably greater than 5 kDa. This term is also intended to include peptides, and fragments, analogues and derivatives of a protein wherein the fragment, analogue or derivative retains essentially the same biological activity or function as a reference protein. The protein may be a linear structure or a non-linear structure having a folded, for example tertiary or quaternary, conformation. The protein may have one or more prosthetic groups conjugated to it, for example the protein may be a glycoprotein, lipoprotein or chromoprotein. Preferably, the protein is a biologically active protein. For example, the protein may be selected from the group consisting of glycoproteins, serum albumins and other blood proteins, hormones, enzymes, receptors, antibodies, interleukins and interferons.

The term "differential alkylation" is alkylation based on the different intrinsic rates of reaction on a different sites of a protein. One of skill in the art would recognize that differential modification is differential chemical modification of proteins is used to probe protein structure. Differences in the intrinsic rate of modification (here alkylation) of a functional group are measured and are used to infer things about functional group's environment in the protein structure (i.e., slow modifying groups are inferred to be buried, fast solvent exposed).

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Representative synthetic procedures for the preparation of compounds of the invention are outlined below in following schemes.

Scheme 6

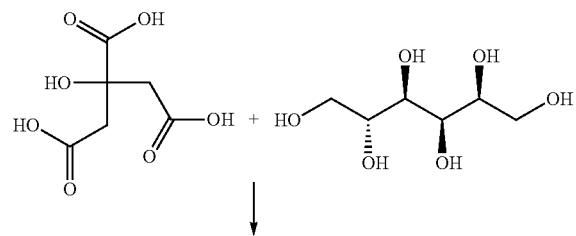

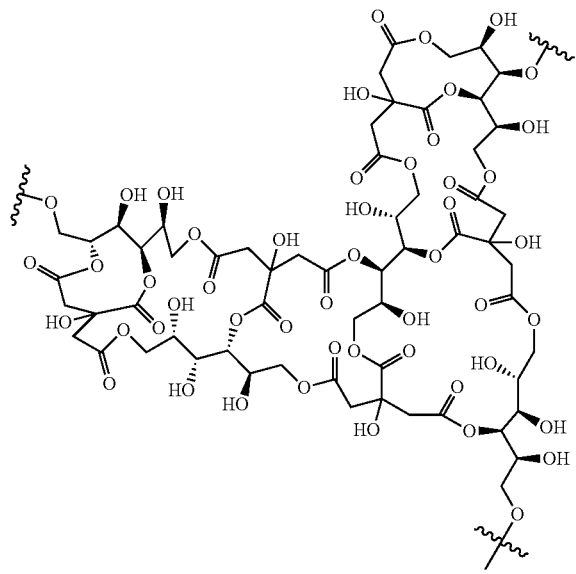

Highly crosslinked, very high molecular weight clear colorless thermoset polymer with representative structure:

-continued
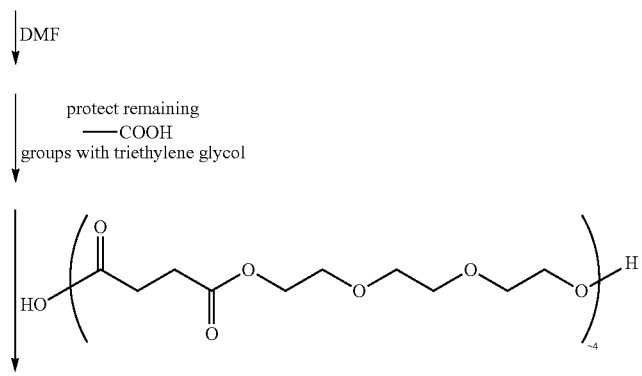
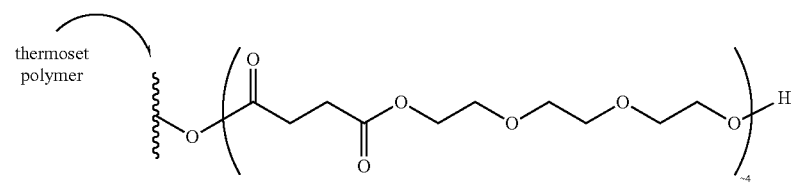
Scheme 7
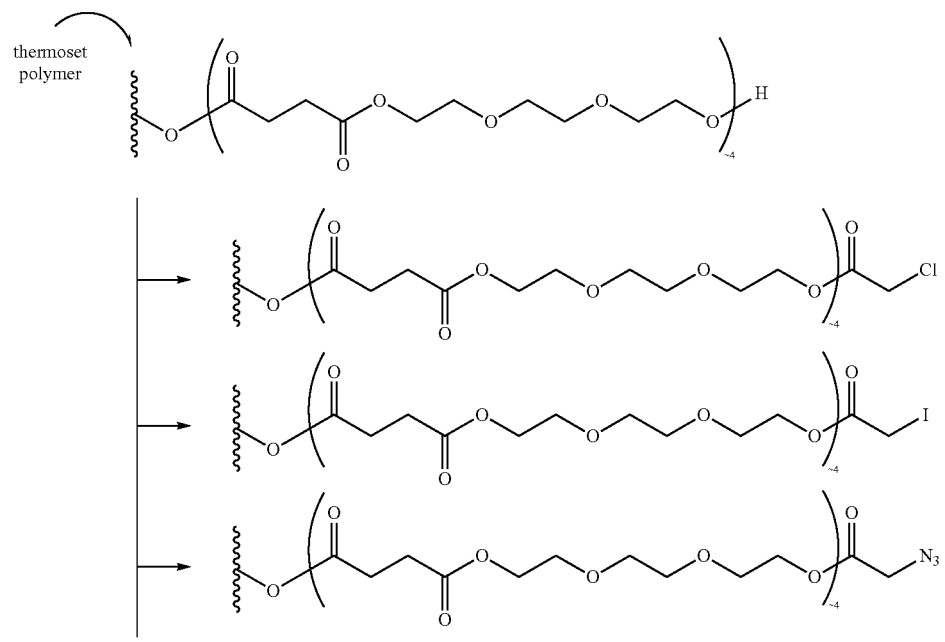

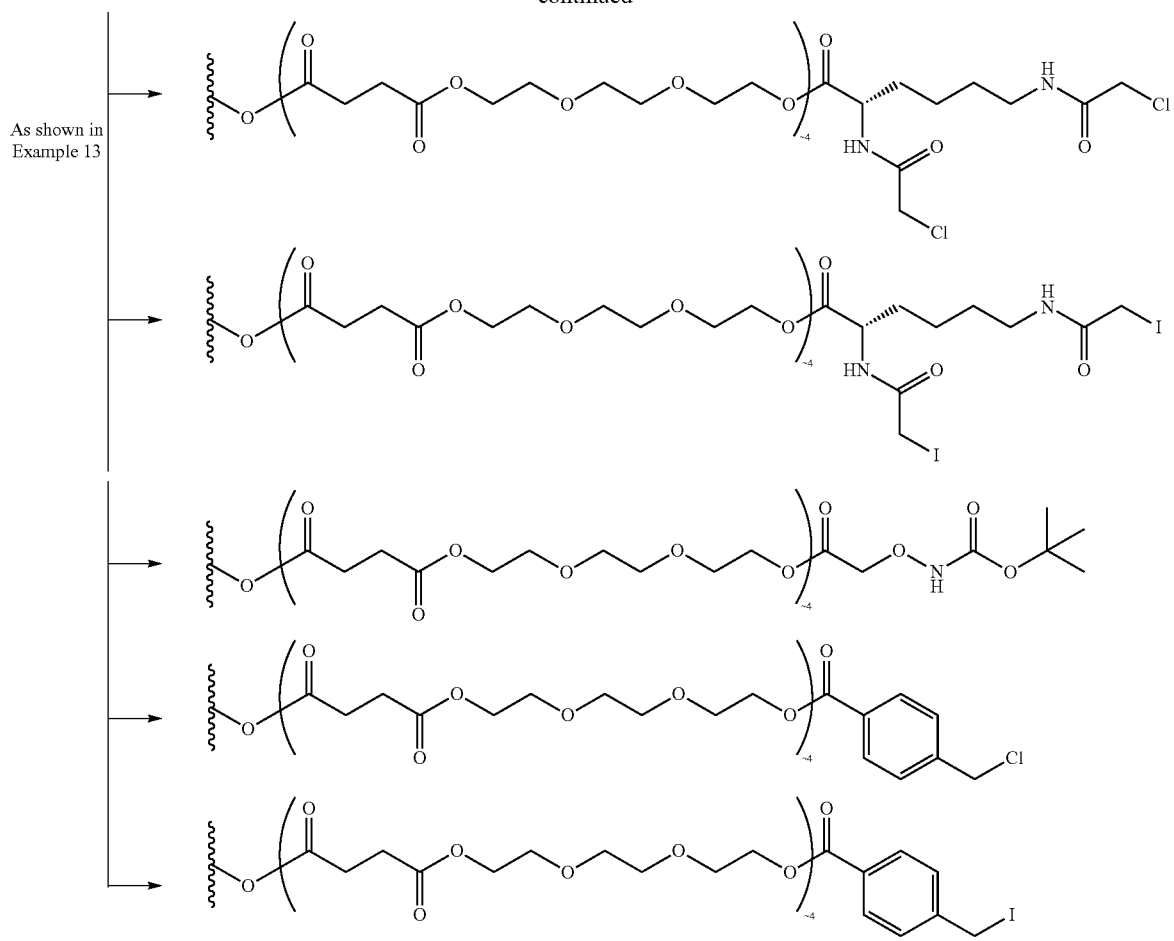
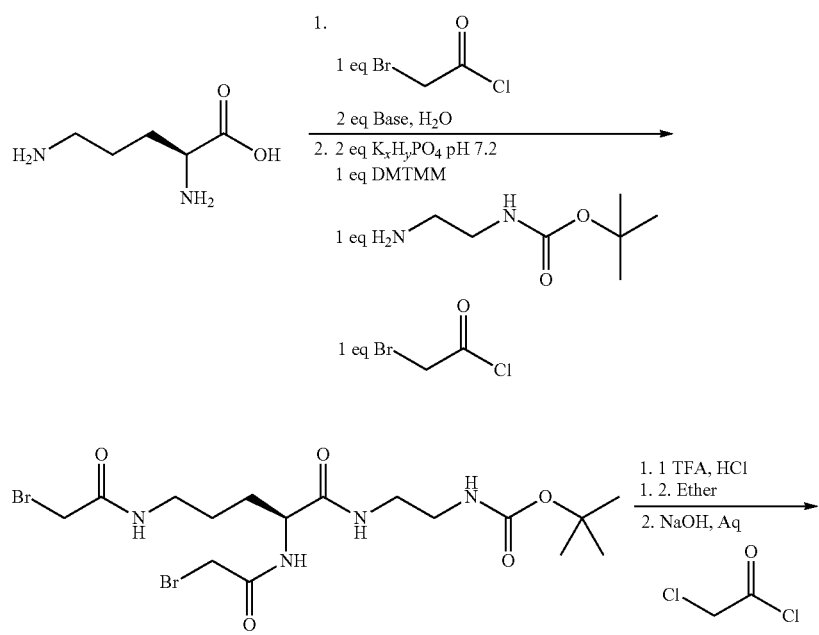
Scheme 8

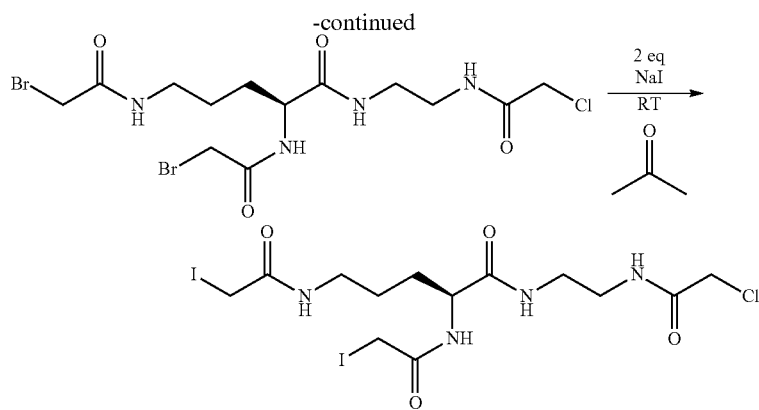
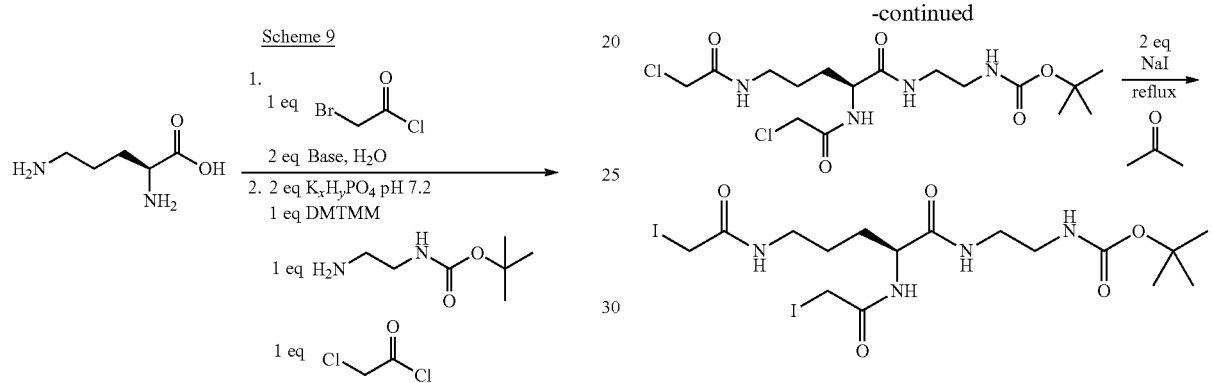
Scheme 9
Scheme 10
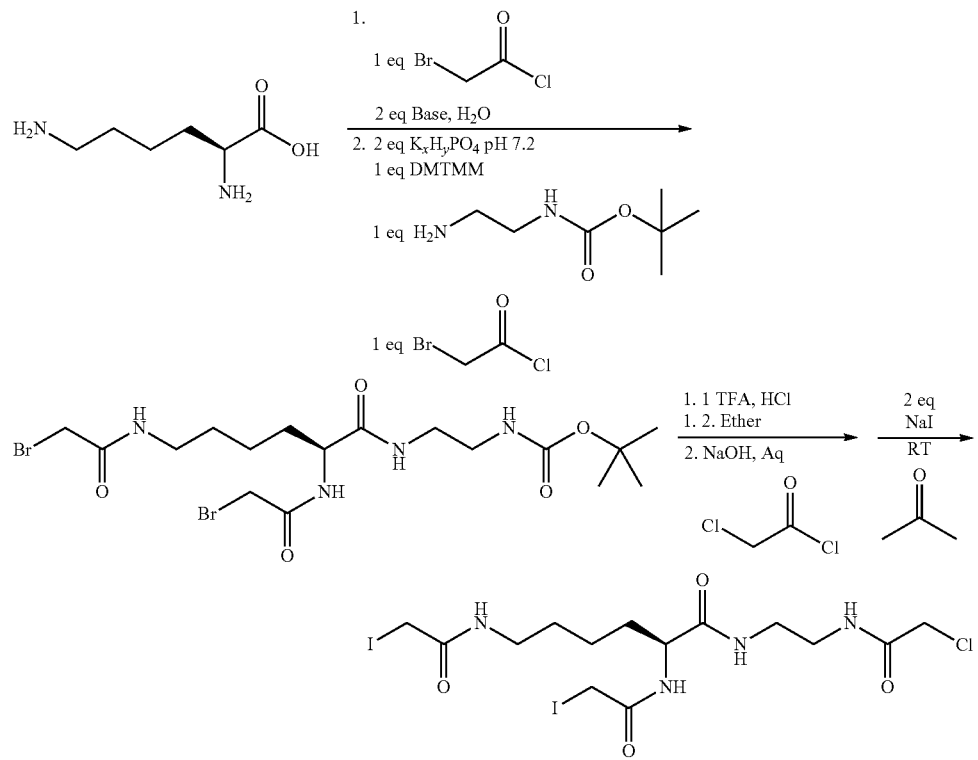

Scheme 11
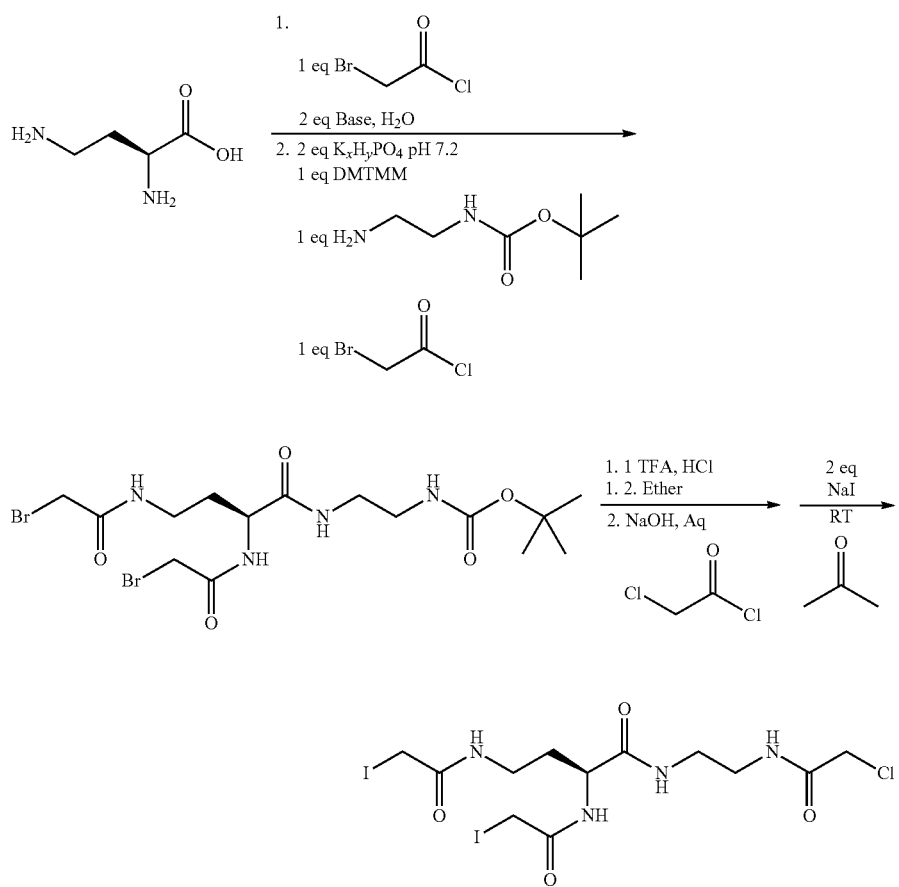
Scheme 12
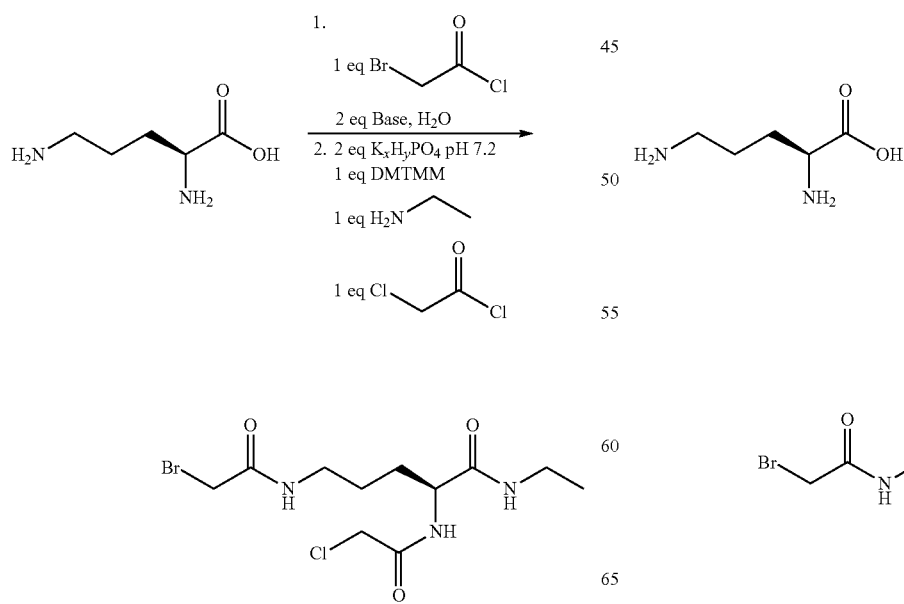
Scheme 13
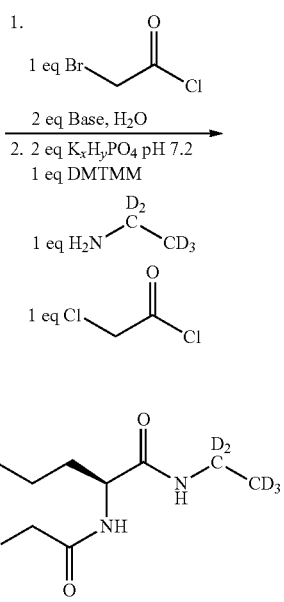

Scheme 14
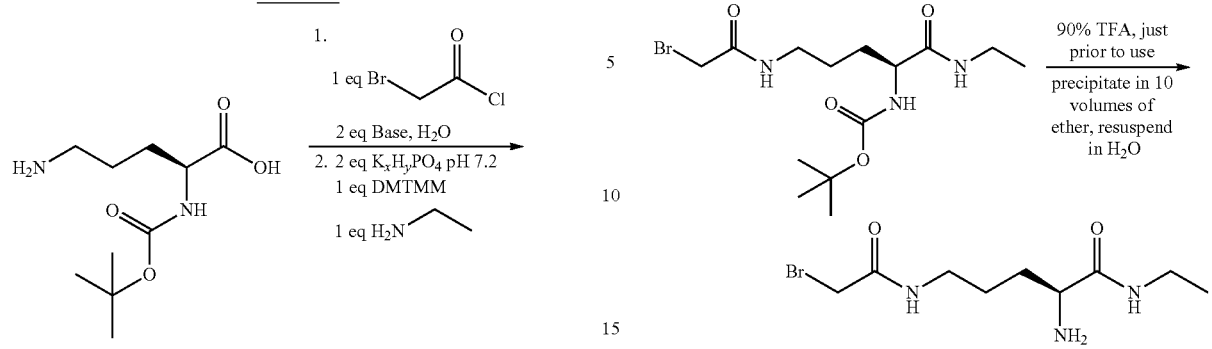
Scheme 15
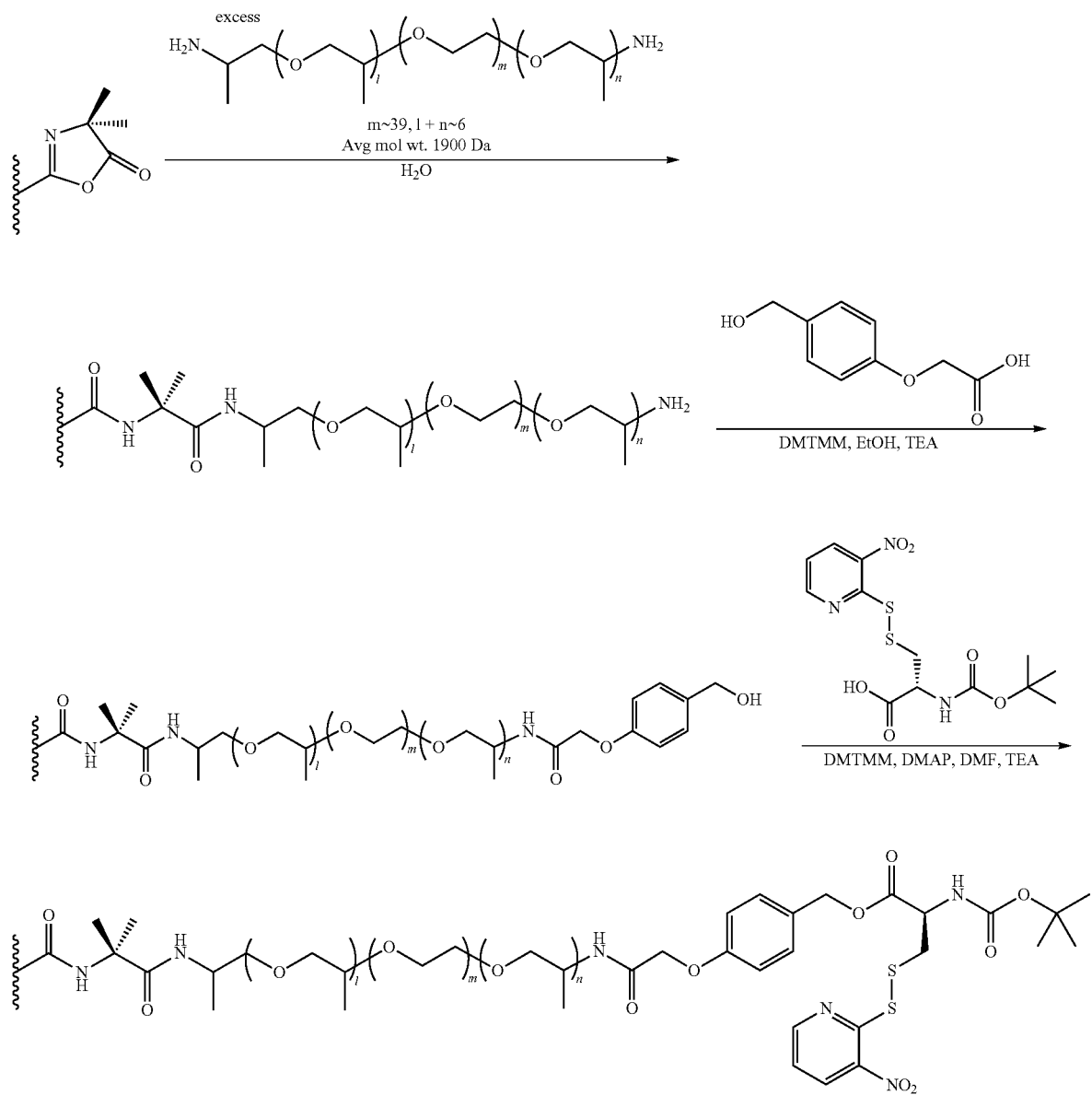

EXAMPLES

The compounds and methods of the disclosure are illustrated further by the following examples, which are provided for illustrative purposes and are not intended to be construed as limiting the disclosure in scope or spirit to the specific compounds and methods described in them.

Example 1

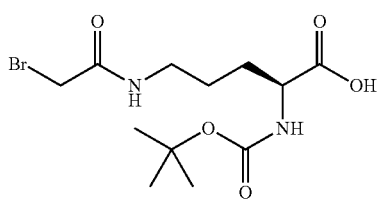 [SMILES: CC(C)(C)OC(=O)N[C@@H](CCCNC(=O)CBr)C(=O)O]

A solution of sodium bicarbonate (10 mmols), sodium carbonate (10 mmols), sodium hydroxide (46 mmols) and Na-Boc ornithine (10 mmols) is cooled in water (40 mL) to 0° C. and stirred at high speed. A solution of bromoacetyl chloride (24 mmols) in dioxane (20 mL) is quickly added to the aqueous solution, in less than 2 minutes and stirred at 0° C. for 3 hours and at room temperature for 20 minutes. The reaction is diluted with 1 M citric acid (50 mL) and extracted with ethyl acetate (4×100 mL). The organic phases were pooled and washed with brine (20 mL), dried over sodium sulfate and the solvent is removed under reduced pressure. MS (MH$^+$) 353, 355.

Example 2

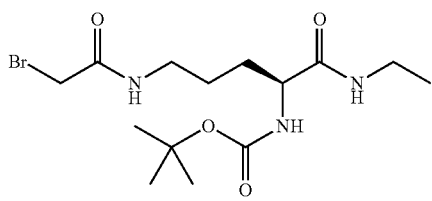 [SMILES: CCNC(=O)[C@H](CCCNC(=O)CBr)NC(=O)OC(C)(C)C]

A solution of Nδ-bromoacetamido-Na-Boc ornithine (3.7 mmol) in ethanol (10 mL) is cooled to 0° C. and stirred at high speed. Ethylamine (3.7 mmol, in aqueous solution) and 4-(4,6-Dimethoxy-1,3,5-triazin-2-yl)-4-methylmorpholinium chloride (4.0 mmols) is added in rapid succession. The solution is stirred for one hour at 0° C. and an aqueous solution of sodium carbonate (1 M, 2 mL) is added and stirred for another hour at 0° C. The reaction is diluted with 1 M citric acid (10 mL) and brine (4 mL) and extracted with ethyl acetate (4×10 mL). The organic phases are pooled and washed with brine (4 mL), and dried over sodium sulfate. Silica (12.1 g) is added and the solvent is removed under reduced pressure. The residue is purified by flash chromatography (20 mL/min, 100% Hexanes to 100% ethylacetate). MS (MH$^+$) 380, 382.

Example 3

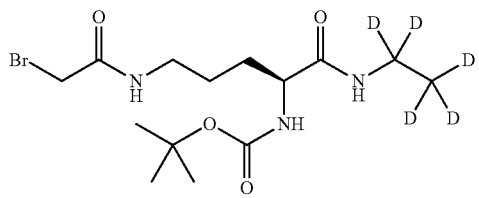 [SMILES: [2H]C([2H])([2H])C([2H])([2H])NC(=O)[C@H](CCCNC(=O)CBr)NC(=O)OC(C)(C)C]

A solution of Nδ-bromoacetamido-Na-Boc ornithine (3.7 mmol) in ethanol (20 mL) is cooled to 0° C. and stirred at high speed. Add deuterated ethylamine (3.7 mmol, HCl salt) and 4-(4,6-Dimethoxy-1,3,5-triazin-2-yl)-4-methylmorpholinium chloride (4.0 mmols) in rapid succession. The reaction proceeds for 10 minutes at 0° C. and an aqueous solution of sodium carbonate (1M, 3.5 mL) is added and proceeds for another hour at 0° C. Dilute the reaction with 1 M citric acid (10 mL) and brine (4 mL) and extract with ethyl acetate (4×10 mL). Pool the organic phases and wash with brine (4 mL), dry over sodium sulfate. Purify by flash chromatography. MS (MH$^+$) 385, 387.

Example 4

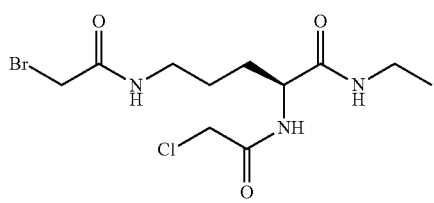 [SMILES: CCNC(=O)[C@H](CCCNC(=O)CBr)NC(=O)CCl]

A solution of Nδ-bromoacetamido-Na-Boc ornithine ethyl amide (24 μmol) is incubated in 95% trifluoroacetic acid (90 μL) at room temperature for 20 minutes. The reaction is diluted with ether (900 μL) and the precipitate is isolated by centrifugation. The precipitate is re-suspended in water (50 μL), and sodium carbonate (1 M, 200 μL) and chloroacetyl chloride (48 μmol) is added in rapid succession. The mixture is stirred vigorously for 5 minutes and incubated at room temperature for 2 hours. The reaction is quenched with acetic acid and frozen. The mixture is purified by HPLC chromatography. MS (MH$^+$) 356, 358.

Example 5

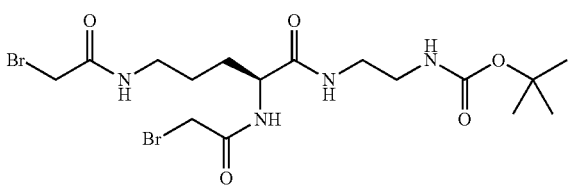 [SMILES: CC(C)(C)OC(=O)NCCNC(=O)[C@H](CCCNC(=O)CBr)NC(=O)CBr]

A solution of sodium hydroxide (45 mmols) and ornithine (10 mmols) in water (20 mL) is cooled to 0° C. and stirred at high speed. Bromoacetyl chloride (24 mmols) is added and stirred for 4 hours at 0° C. Hydrochloric acid (37% aqueous solution, 400 μL), mono Boc-diaminoethane (15 mmols), 4-(4,6-Dimethoxy-1,3,5-triazin-2-yl)-4-methylmorpholinium chloride (15 mmols) and sodium bicarbonate (1 M, 10 mL) are added in rapid succession. The mixture is stirred overnight and allowed to reach room temperature. Then, 4-(4,6-dimethoxy-1,3,5-triazin-2-yl)-4-methylmorpholinium chloride (7.5 mmols), hydrochloric acid (37% aqueous solution, 400 μL), ethanol (10 ml) and ethyl acetate (10 mL) are added, and the mixture is stirred for an additional hour at room temperature. The reaction is extracted with ethyl acetate/ethanol (4:1, 4×50 mL). The organic fractions are pooled, washed with brine (10 mL) and dried over sodium sulfate. Silica (12 g) is added and the solvent is removed under reduced pressure. The residue is purified by flash chromatography (20 mL/min, 100% Hexanes to 100% ethyl acetate to 100% ethanol). MS (MH$^+$) 515, 517, 519.

Example 6

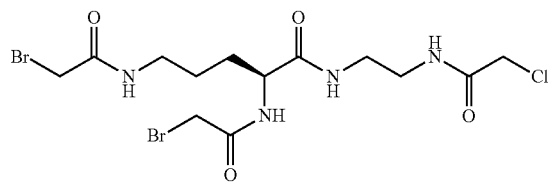 [SMILES: O=C(CCl)NCCNC(=O)[C@H](CCCNC(=O)CBr)NC(=O)CBr]

Mono-boc-ethyldiamino mono-dibromoacetamido ornithine (2 mmol) is stirred in 95% trifluoroacetic acid for 20 minutes at room temperature. The mixture is precipitated in ether (100 mL) and the precipitate collected by centrifugation. The precipitate is re-suspended in water (10 mL) and cooled to 0° C. Sodium hydroxide (10 N, 2 mL) and chloroacetyl chloride (4.8 mmol) is added in rapid succession and stirred for one hour. The reaction is extracted with ethyl acetate/ethanol (4:1, 4×50 mL). The organic fractions are pooled, washed with brine (10 mL) and dried over sodium sulfate. Silica (12 g) is added and the solvent is removed under reduced pressure. The residue is purified by flash chromatography (20 mL/min, 100% Hexanes to 100% ethyl acetate to 100% ethanol). MS (MH$^+$) 491, 493, 495.

Example 7

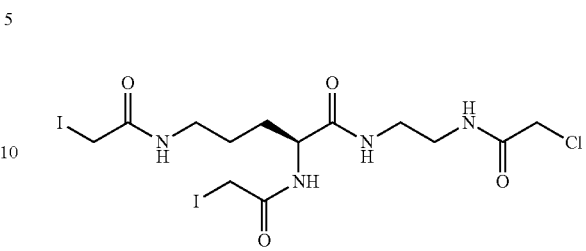

Mono-chloroacetamido ethyldiamino mono-dibromoacetamido ornithine (10 μmol) and sodium iodide (20 μmol) are incubated in acetone for 2 hours at room temperature. The mixture is purified by HPLC. MS (MH$^+$) 587.

Example 8

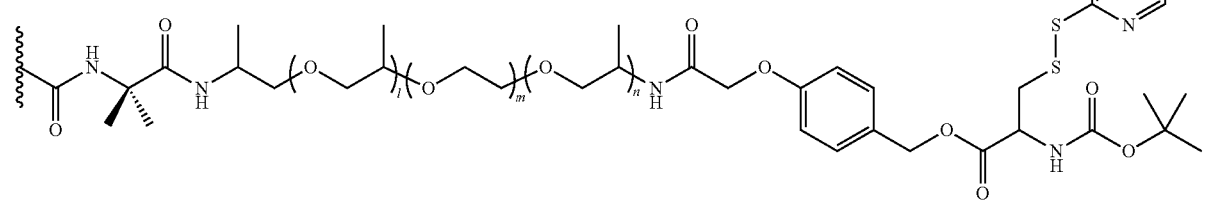

Ultralink biosupport media (0.67 g, Pierce) is added to a solution of Jeffamine® PEG MW 1900 (6.46 g, Fluka) in water (34 mL) and allowed to rock overnight. Resin is decanted into a peptide synthesis vessel and the resin bed is drained of reaction. The resin is washed with 18 MOhm resistance water (10×10 mL), 95% ethanol (10×10 mL), and 100% ethanol (1×10 mL). Hydroxymethyl phenyloxyacetic acid (462 μmol) is dissolved in ethanol (10 mL) and added to resin. 4-(4,6-Dimethoxy-1,3,5-triazin-2-yl)-4-methylmorpholinium chloride (554 umols) and triethylamine (462 umols) is added, and the resin bed is agitated by pipetting. The reaction is allowed to proceed for 30 minutes at room temperature with pipette mixing periodically. The resin is washed with 95% ethanol (5×10 mL), and the coupling reaction is repeated. The resin is again washed with 95% ethanol (5×10 mL), 18 MOhm resistance water (10×10 mL), dimethylformamide (7×10 mL), and anhydrous dimethylformamide (3×10 mL).

Anhydrous dimethylformamide (5 mL) is added to the resin bed. Acetic anhydride (462 μmol) and dimethylaminopyridine (15.4 μmol) is added and the resin bed is agitated by pipetting. The reaction is allowed to proceed for 30 minutes at room temperature with pipette mixing periodically. The resin is washed with dimethylformamide (3×10 mL) and water (3×10 mL), then treated with 50 mM tetramethyl ammonium hydroxide (10 mL) for 1 minute at room temperature. The resin is washed with water (5×10 mL), 95% TFA (1×5 mL) for 20 minutes at room temperature, water (10×10 mL), dimethylformamide (7×10 mL) and anhydrous dimethylformamide (3×5 mL).

Then, to half of the resin bed anhydrous dimethylformamide (5 mL) is added, followed by Boc-Cys-Npys (231 µmol), and the resin bed is agitated by pipetting. 4-(4,6-Dimethoxy-1,3,5-triazin-2-yl)-4-methylmorpholinium chloride (276 µmol), triethylamine (231 µmol), and dimethylaminopyridine (15.4 µmol) are added, the resin bed is agitated by pipetting. The reaction is allowed to proceed for 30 minutes at room temperature with pipette mixing periodically.

The resin bed is drained of reaction mixture, and washed with dimethylformamide (5×10 mL) and anhydrous dimethylformamide (2×10 mL). Boc-Cys-Npys acetylation reaction is repeated and the resin bed is drained. The resin is washed with dimethylformamide (5×10 mL), 1M Hepes pH 6.0 (1×10 mL), and 18 MOhm resistant water (5×10 mL). The resin is stored at 4° C.

Example 9

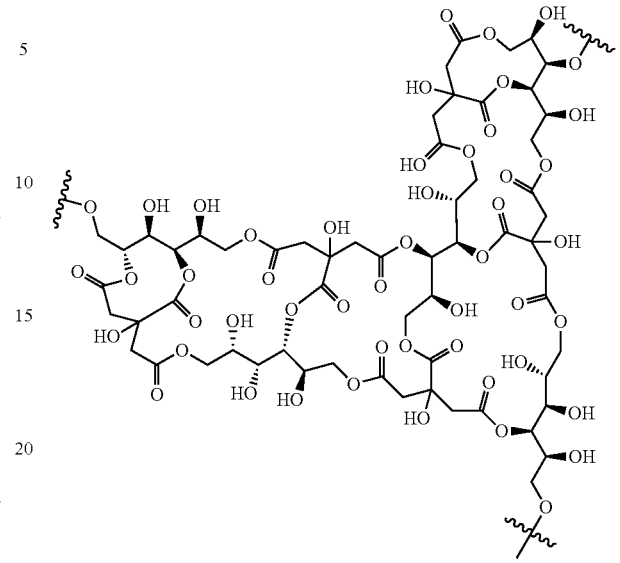

A 500 mL round bottom flask was dried with Teflon covered stir bar overnight at 150° C. The flask is charged while warm with 18.2 g sorbitol and 19.2 g citric acid (Acros Organics). The mixture is heated to 120° C. with stirring under reduced pressure until the mass reflects the 300 mmol theoretical water loss expected from complete polyester formation. The polymer is a clear-white foam.

Example 10

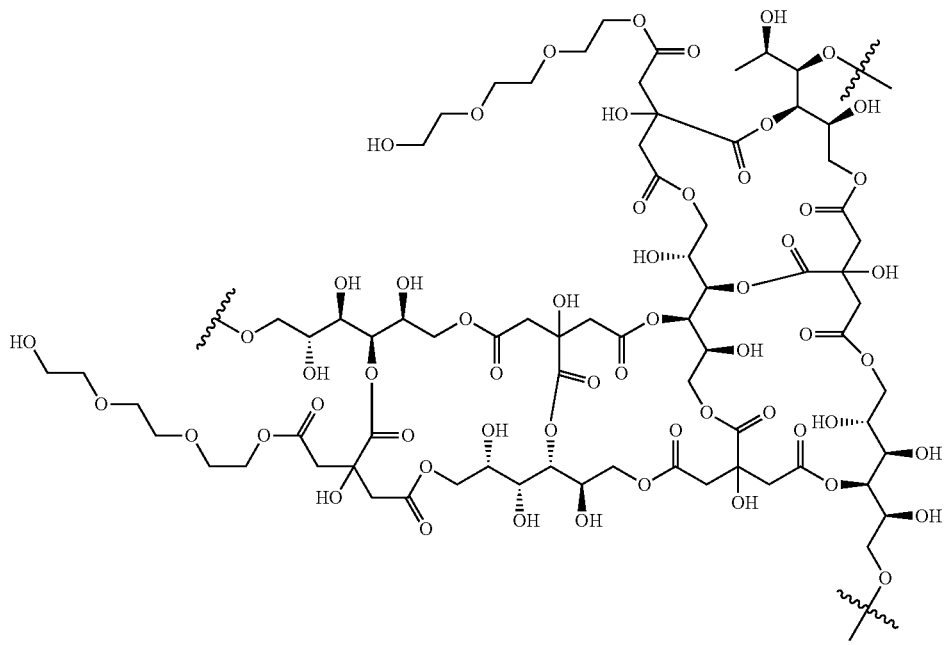 [SMILES: *OC[C@@H](O)[C@@H](O)[C@@H]1OC(=O)C(O)(CC(=O)OCCOCCOCCO)CC(=O)OC[C@H](O)[C@@H](O)[C@@H]2OC(=O)C(O)(CC(=O)OC[C@@H]1O)CC(=O)O[C@H]1[C@@H]3OC(=O)C(O)(CC(=O)OC[C@@H](O)[C@@H](O)[C@@H]([C@@H](O)CO*)OC(=O)CC(O)(CC(=O)OC[C@H]2O)C(=O)OC[C@@H]1O)CC(=O)OC[C@H](O)[C@H]([C@H](O*)[C@@H](C)O)OC(=O)C(O)(CC(=O)OCCOCCOCCO)CC(=O)OC[C@H]3O]

The reaction is cooled to room temperature and brought to room pressure. Dimethyl formamide (DMF, 100 g) and 5 mm glass beads (100 g) are added and the material is ground on a Buchi Rotary Evaporator at room temperature and pressure for 48 hours. The glass beads are removed with a sieve and the ground thermoset is collected and washed with DMF (5×100 g) by centrifugation (3 minutes at 3000 rpm GH 3.8 rotor, Allegra 6KR centrifuge).

The vessel containing the washed ground thermoset/DMF slurry was charged with 4.5 g triethylene glycol, 37 mg dimethylamino pyridine (DMAP) and 831 mg 4-(4,6-Dimethoxy-1,3,5-triazin-2-yl)-4-methylmorpholinium chloride (DMTMM) and rocked for one hour at room temperature. The modified ground thermoset polymer was washed as above.

Example 11

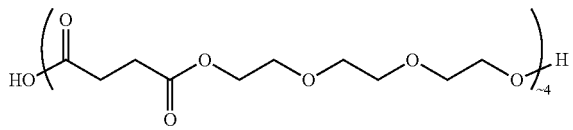

A 500 mL round bottom flask was dried with Teflon covered stir bar overnight at 150° C. The flask is charged while warm with 60 g triethylene glycol and 40 g succinic anhydride (Acros Organics). The mixture is heated to 120° C. with stirring and catalyzed with the addition of 3.84 g citric acid. After the initial mass-neutral ring-opening formation of triethylene glycol succinate the formation of additional ester bonds is monitored until the mass reflects 300 mmol theoretical water loss expected for 75% of potential polyester formation. The polymer is a clear liquid.

Example 12

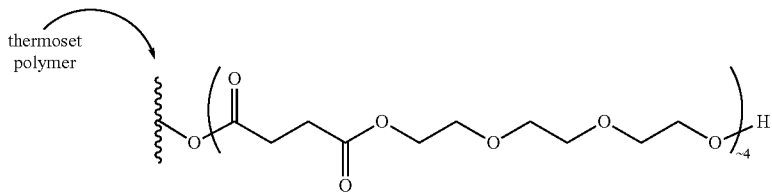

The vessel containing the washed modified ground thermoset polymer is charged with the entire linear copolymer reaction mixture, 244 mg dimethylamino pyridine (DMAP) and 5.76 g 4-(4,6-dimethoxy-1,3,5-triazin-2-yl)-4-methylmorpholinium chloride (DMTMM), 10.3 g diisopropylethylamine (DIEA) and rocked for one hour at room temperature. The linear copolymer grafted to the modified ground thermoset was washed as above. The polymer graph weighed 90 g wet (DMF) and was stored under an additional 90 g DMF at 4° C.

Example 13

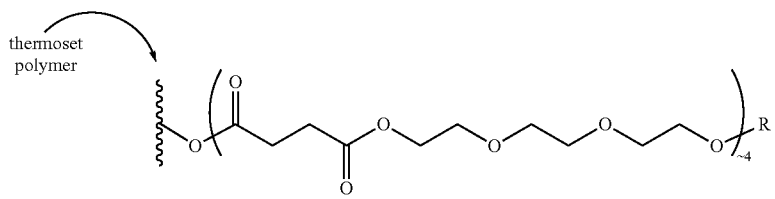

Portions of the washed grafted copolymer were further modified with different pendant functionalities as follows:

1) R = 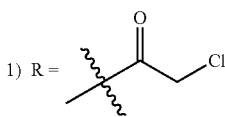 [SMILES: *C(=O)CCl]

chloroacetic anhydride (85 mg) and dimethylaminopyridine (DMAP, 2 mg);

2) R = 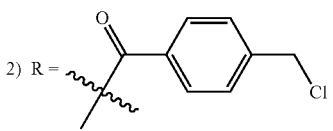

4-(chloromethyl)benzoic acid (85 mg), dimethylaminopyridine (DMAP, 2 mg) 4-(4,6-dimethoxy-1,3,5-triazin-2-yl)-4-methylmorpholinium chloride (DMTMM, 138 mg), diisopropylethylamine (DIEA, 64.5 mg);

3) 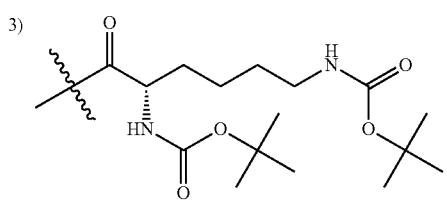 [SMILES: *C(=O)[C@H](CCCCNC(=O)OC(C)(C)C)NC(=O)OC(C)(C)C]

N,N'-Di-Boc-L-lysine (173 mg), dimethylaminopyridine (DMAP, 2 mg) 4-(4,6-Dimethoxy-1,3,5-triazin-2-yl)-4-methylmorpholinium chloride (DMTMM, 138 mg), diisopropylethylamine (DIEA, 64.5 mg).

For all reactions reagents were added to 5 mL of grafted polymer slurry and rolled at room temperature for an hour. The resins were washed with 3×10 mL of DMF, 3×10 mL of H$_2$O and 4×10 mL of DMF.

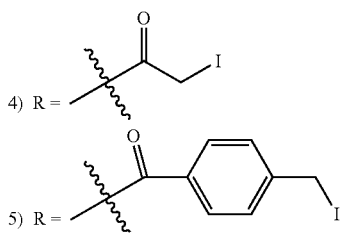

After washing, the α-chloro resins were further derivatized as follows: 500 μL each of the chloroacetylated and 4-(chloromethyl) benzoic acid-acetylated resin slurries were each incubated overnight at room temperature with NaI (150 mg) in 500 μL acetone. The 500 μL scale reactions were washed with 3×1 mL of DMF, 3×1 mL of H$_2$O and 4×1 mL of DMF. The 5 mL reaction mixture was washed with ten-fold higher volumes. The derivatized resin slurries were stored at 4° C. under anhydrous DMF.

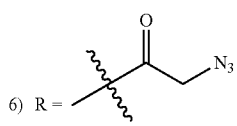 [SMILES: *C(=O)CN=[N+]=[N-]]

After washing, 5 mL of chloroacetylated resin slurry was incubated overnight at room temperature with NaI (10 mg) and NaN$_3$ in 3 mL of H$_2$O. The 500 μL scale reactions were washed with 3×1 mL of DMF, 3×1 mL of H$_2$O and 4×1 mL of DMF. The 5 mL reaction mixture was washed with ten-fold higher volumes. The derivatized resin slurries were stored at 4° C. under anhydrous DMF.

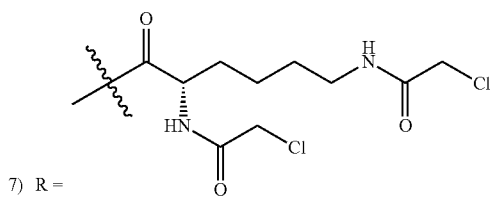 [SMILES: *C(=O)[C@H](CCCCNC(=O)CCl)NC(=O)CCl]

The N,N'-Di-Boc-L-lysine resin was deprotected (2.5 mL resin, 12.5 mL 95% trifluoroacetic acid, 30 minutes room temperature. The resin was washed with 3×10 mL of DMF, 3×10 mL of H$_2$O and 4×10 mL of DMF. The de-protected amines in the slurry were chloroacetylated for 30 minutes at room temperature (chloroacetic anhydride (170 mg), DIEA (129 mg), 10 mL H$_2$O). 500 μL of this reaction was iodinated overnight at room temperature with NaI (300 mg) in 1 mL acetone. The resin was washed with 3×1 mL of DMF, 3×1 mL of H$_2$O and 4×1 mL of DMF and stored at 4° C. under anhydrous DMF.

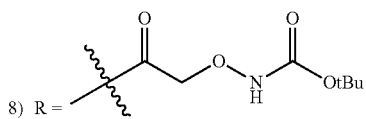 [SMILES: *C(=O)CONC(=O)OC(C)(C)C]

N-Boc-(aminooxyacetic) acid (95 mg), dimethylaminopyridine (DMAP, 2 mg) 4-(4,6-Dimethoxy-1,3,5-triazin-2-yl)-4-methylmorpholinium chloride (DMTMM, 138 mg), diisopropylethylamine (DIEA, 64.5 mg).

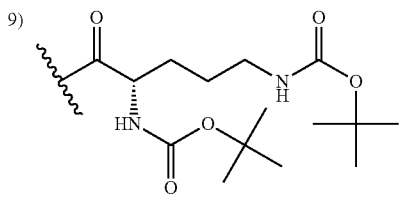 [SMILES: *C(=O)[C@H](CCCNC(=O)OC(C)(C)C)NC(=O)OC(C)(C)C]

N,N'-Di-Boc-L-ornithine (166 mg), dimethylaminopyridine (DMAP, 2 mg) 4-(4,6-Dimethoxy-1,3,5-triazin-2-yl)-4-methylmorpholinium chloride (DMTMM, 138 mg), diisopropylethylamine (DIEA, 64.5 mg).

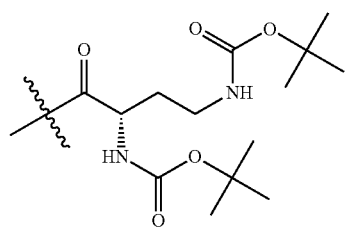

N,N'-Di-Boc-L-diaminobutyric acid (159 mg), dimethylaminopyridine (DMAP, 2 mg) 4-(4,6-Dimethoxy-1,3,5-triazin-2-yl)-4-methylmorpholinium chloride (DMTMM, 138 mg), diisopropylethylamine (DIEA, 64.5 mg).

Example 14

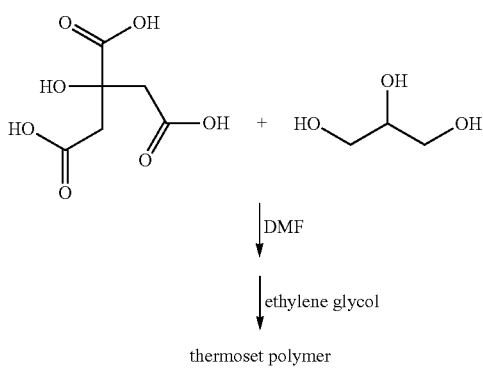

A 500 mL round bottom flask was dried overnight at 150° C. The flask is charged while warm with 14 g glycerol and 19.2 g citric acid (Acros Organics), and 5.5 g triethyl citrate (as a plasticizer, Acros Organics). The mixture is heated to 150° C. with stirring by hand every 10 minutes until the mass reflects the 300 mmol theoretical water loss expected from complete polyester formation. The polymer is a clear-white foam.

The reaction is cooled to room temperature and brought to room pressure. Dimethyl formamide (DMF, 100 g) and 5 mm glass beads (100 g) are added and the material is ground on a Buchi Rotary Evaporator at room temperature and pressure for 48 hours. The glass beads are removed with a sieve and the ground thermoset is collected and washed with DMF (5×100 g) by centrifugation (3 minutes at 3000 rpm GH 3.8 rotor, Allegra 6KR centrifuge).

The vessel containing the washed ground thermoset/DMF slurry was charged with 1.86 g ethylene glycol, 37 mg dimethylamino pyridine (DMAP) and 831 mg 4-(4,6-Dimethoxy-1,3,5-triazin-2-yl)-4-methylmorpholinium chloride (DMTMM) and rocked for one hour at room temperature. The modified ground thermoset polymer was washed as above.

Example 15

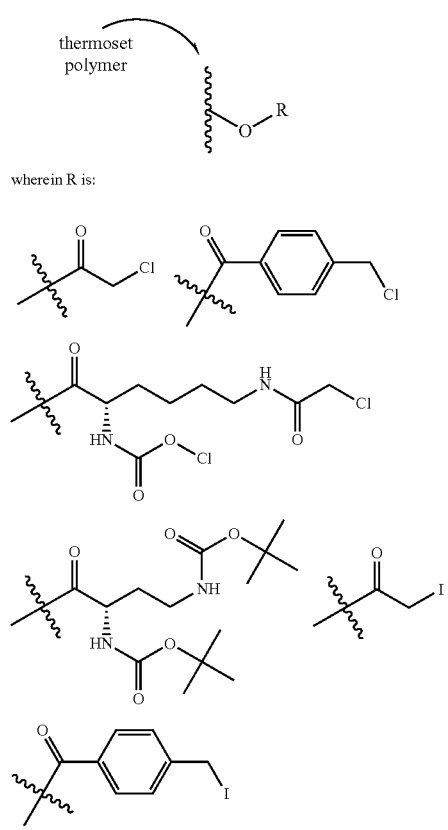

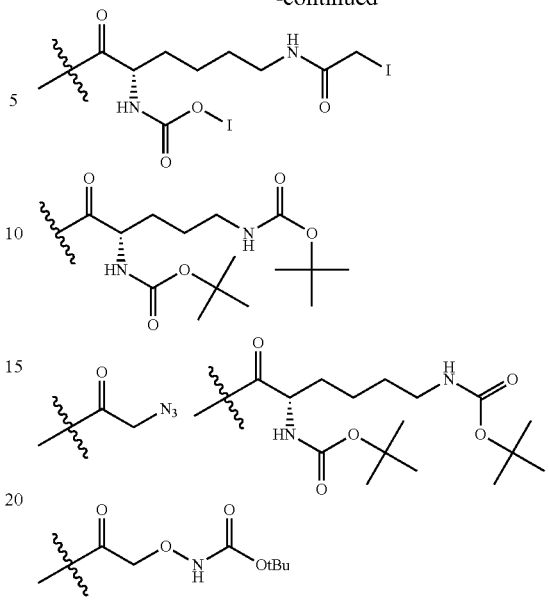

Portions of the washed grafted thermoset polymer of Example 14 were further modified with the same 15 pendant functionalities, under the same reaction conditions as described in Example 13.

Example 16

Proteolysis for Mass Spectrometry Analysis:

Proteolysis mixture (50 µL; 100 mM Hepes pH 7.1; 5 mM CaCl$_2$, chymotrypsin and trypsin to 0.1 mg/mL) is added to each resin and incubated for 30 minutes at room temperature. The solution is removed, the resin is washed with 200 µL 0.1% SDS and 1 mL of water twice. Peptides were eluted using the elution procedure below.

Elution:

The resin is swelled with 10 µL dimethylformamide and hydrolyzed with 15 µL of 10N NaOH and 15 µL of water. After 5 minutes, the solution is neutralized with 12 µL glacial acetic acid. Eluted peptides are injected directly onto a LCMS system with a trapping column and a diverter valve as known in the art. For gel analysis, it is necessary to skip the proteolysis step. TCA may be used to precipitate the resin eluted proteins.

Results:

Aminooxyacetic acid-containing resin

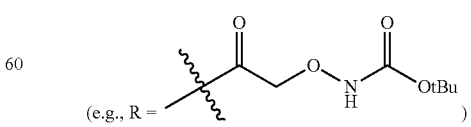

of Example 15 is reacted with benzaldehyde. The benzaldehyde capture is shown in FIG. 2, where the LCMS presents expected 180 m/z.

4-Iodomethyl benzoic acid-containing resin

Figure 3:
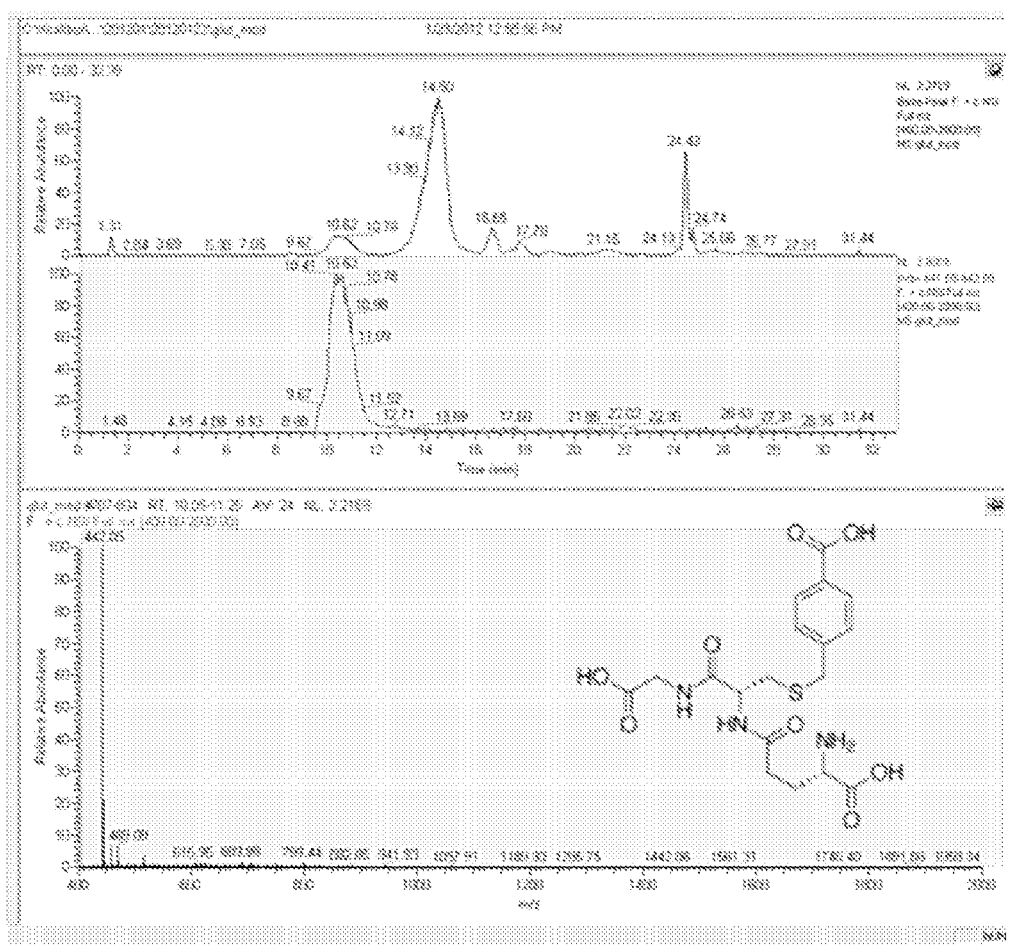
FIG. 3 shows LCMS spectra of the glutathione capture with 4-iodomethyl benzoic acid-containing capture system.

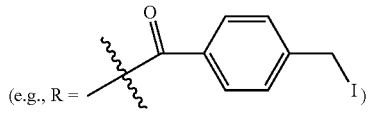 [SMILES: *C(=O)c1ccc(CI)cc1]

of Example 15 is reacted with glutathione. The glutathione capture is shown in FIG. 3, where the LCMS presents expected 442 m/z.

α-N₃-aceto-containing resin

Figure 4:
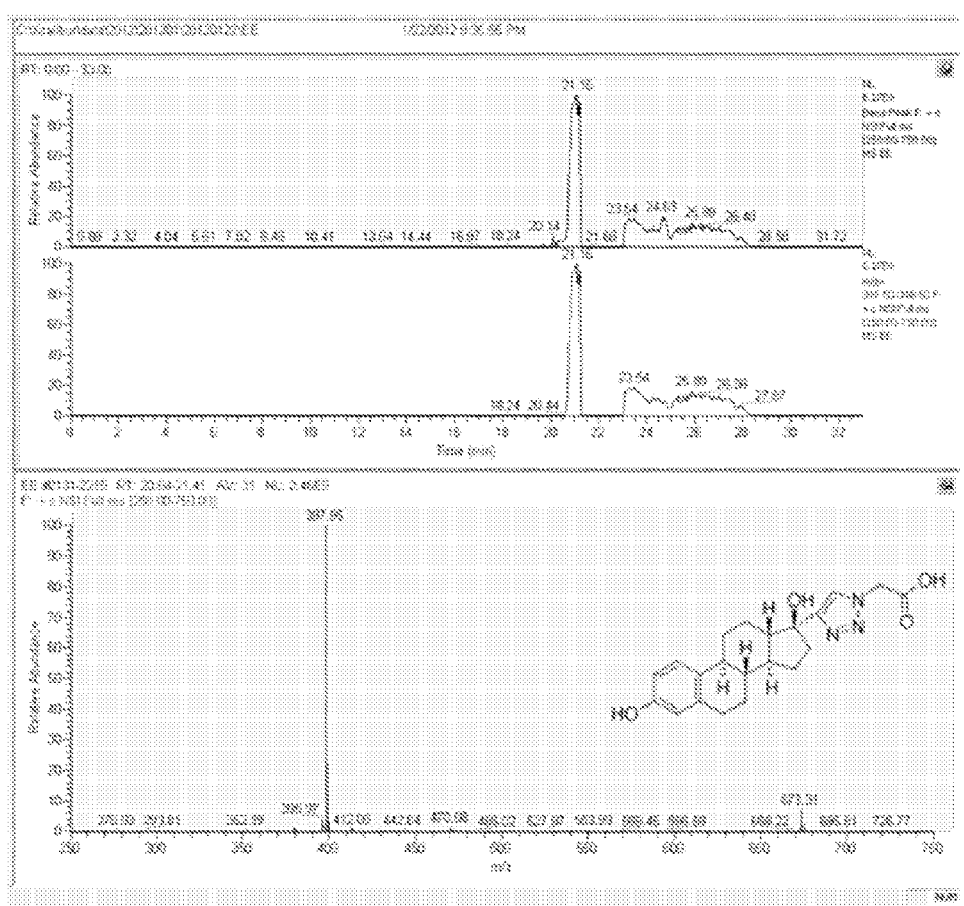
FIG. 4 shows LCMS spectra of the ethynylestradiol capture with α-N$_3$-aceto-containing capture system.

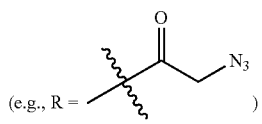 [SMILES: *C(=O)CN=[N+]=[N-]]

of Example 15 is reacted with ethynylestradiol (birth control pill). The ethynylestradiol capture is shown in FIG. 4, where the LCMS presents expected 398 m/z.

α-iodo-aceto-containing resin

Figure 5:
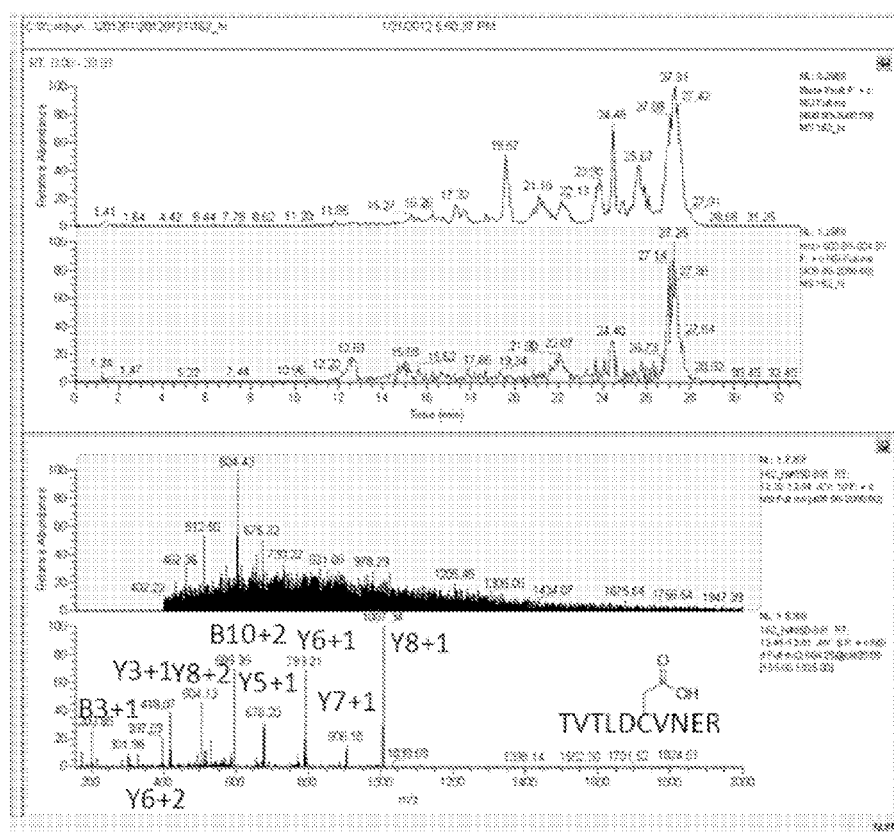
FIG. 5 shows LCMS spectra of the cysteine containing peptide capture with α-iodo-aceto-containing capture system.

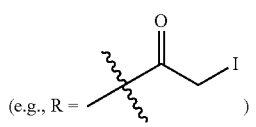 [SMILES: *C(=O)CI]

of Example 15 is reacted with E162C mutant of the N-terminal domain of 90 kDa heat shock protein. The protein proteolyzed on resin peptide [SEQ ID No. 1] eluted post-proteolysis capture is shown in FIG. 5, where the LCMS presents expected 604 m/z (the value reflects doubly-charged molecule).

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

I claim:
1. A method for isolating proteins, the method comprising:
   1) contacting a capture system with a biological fluid to obtain captured proteins, wherein the capture system is of the formula:

R'—X'—Z' wherein
   R' is a polymer resin, wherein the polymer resin comprises a copolymer of polyalcohol and carboxylic acid monomers;
   X' is absent or a polymer linker; and
   Z' is a capture group, wherein the capture group is capable of reacting with a disulfide or a thiol group; and
   2) cleaving the captured proteins.

2. A method according to claim 1, wherein contacting results in reacting cysteine groups on the biological fluid with Z' group of formula (I) to obtain the captured proteins.

3. A method according to claim 1, wherein cleaving the captured proteins comprises cleaving by an acid or a base.

4. A method according to claim 3, wherein cleaving by an acid or a base hydrolyzes the capture system.

* * * * *